US011685936B2

United States Patent
Õunap et al.

(10) Patent No.: US 11,685,936 B2
(45) Date of Patent: Jun. 27, 2023

(54) PLATFORM FOR DEVELOPING STABLE MAMMALIAN CELL LINES

(71) Applicant: Icosagen Cell Factory OÜ, Tartumaa (EE)

(72) Inventors: Kadri Õunap, Õssu (EE); Eva-Maria Tombak, Õssu (EE); Mart Toots, Õssu (EE); Madis Jakobson, Õssu (EE); Mart Ustav, Jr., Õssu (EE); Kerttu Murumets, Õssu (EE); Urve Toots, Õssu (EE); Andres Männik, Õssu (EE); Mart Ustav, Sr., Õssu (EE)

(73) Assignee: Icosagen Cell Factory OÜ, Õssu (EE)

( * ) Notice: Subject to any disclaimer, the term of this patent is extended or adjusted under 35 U.S.C. 154(b) by 769 days.

(21) Appl. No.: 16/655,717

(22) Filed: Oct. 17, 2019

(65) Prior Publication Data

US 2020/0123576 A1 Apr. 23, 2020

Related U.S. Application Data

(60) Provisional application No. 62/747,158, filed on Oct. 18, 2018.

(51) Int. Cl.
 C12N 15/90 (2006.01)
 C12N 15/85 (2006.01)
 C12N 15/10 (2006.01)

(52) U.S. Cl.
 CPC ....... *C12N 15/907* (2013.01); *C12N 15/1024* (2013.01); *C12N 15/85* (2013.01); *C12N 2310/20* (2017.05); *C12N 2800/80* (2013.01)

(58) Field of Classification Search
 None
 See application file for complete search history.

(56) References Cited

U.S. PATENT DOCUMENTS

2003/0013157 A1* 1/2003 Jakobovits ............ C07K 16/00
  536/23.53
2003/0129169 A1* 7/2003 Krohn ..................... A61P 43/00
  435/456

OTHER PUBLICATIONS

O'Brien et al., Biotechnol. J. 13:e1800226, Jul. 2018, 10 pages (Year: 2018).*
Sultana et al., Nat. Rev. Genet. 18:292-308, 2017 (Year: 2017).*
Jang et al., J. Virol. 83:2592-2600, 2009 (Year: 2009).*
Kurg, R., "DNA Replication—Current Advances", pp. 613-638, 2011 (Year: 2011).*
Kim et al., Biotechnol. Bioprocess Engineer. 13:418-423, 2008 (Year: 2008).*
Bebbington, C.R. et al., High-lever expression of a recombinant antibody from myeloma cells using a glutamine synthetase gene as an amplifiable selectable marker, Biotechnol. Nature Publishing Group, Feb. 1992, pp. 169-175, vol. 10.
Frye, Christopher et al., Industry view on the relative importance of "clonality" of biopharmaceutical-producing cell lines, Biologicals, 2016, pp. 117-122, vol. 4 Issue 2.
Inniss, Mara C. et al., A novel Bxb1 integrase RMCE system for high fidelity site-specific integration of mAb expression cassette in CHO cells, Biotechnology and Bioengineering, 2017, pp. 1837-1846, vol. 114.
Kaufman, Randal J. et al., Amplification and expression of sequences cotransfected with a modular dihydrofolate reductase complementary DNA gene, J. Mol. Biol., 1982, pp. 601-621, vol. 159.
Kim, Min Soo et al., Use of Flp-Mediated Cassette Exchange in the Development of a CHO Cell Line Stably Producing Erythropoietin, Journal of Microbiology and Biotechnology, Mar. 2008, pp. 1342-1351, vol. 18 Issue 7.
Liu, Pei-Qi et al., Generation of a Triple-Gene Knockout Mammalian Cell Line Using Engineered Zinc-Finger Nucleases, Biotechnology and Bioengineering, Dec. 2009, pp. 97-105, vol. 106, Issue 1.
Urlaub, Gail et al., Isolation of Chinese hamster cell mutants deficient in dihydrofolate reductase activity, Proceedings of the National Academy of Sciences of the United States of America, Jul. 1980, pp. 4216-4220, vol. 77 Issue 7.
Wigler, M. et al., Transformation of mammalian cells with an amplifiable dominant-acting gene, Proceedings of the National Academy of Sciences of the United States of America, Jun. 1980, pp. 3567-3570, vol. 77 Issue 6.
Zhang, Lin et al., Recombinase-Mediated Cassette Exchange (RMCE) for Monoclonal Antibody Expression in the Commercially Relevant CHOK1SV Cell Line, Biotechnology Progress, Sep. 2015, pp. 1-12, vol. 00 Issue 00.
Zhu, Jianwei, Mammalian cell protein expression for biopharmaceutical production, Biotechnology Advances, 2012, pp. 1158-1170, vol. 30 Issue 5.

* cited by examiner

Primary Examiner — David Steadman
(74) Attorney, Agent, or Firm — Meunier Carlin & Curfman LLC

(57) ABSTRACT

This disclosure provides methods and landing pad constructs for generation of parental cell lines suitable for targeted integration. A method is provided by the parental cell line development; this is, the introduction of binding sites of BPV1 E2 protein to landing pad vectors so that expressed BPV1 E2 protein could locate the vector to transcriptionally active region in the genome. Cells with high expression level of reporter genes are selected for the next stage and will be used in the development of cell lines expressing another recombinant protein by recombination mediated cassette exchange (RMCE). Landing pad constructs include recombination target sites for site-specific recombinases, and therefore, it could be replaced with gene-of-interest expression construct containing the same set of recombination target sites. This yields the generation of producer cell lines with less effort compared to traditional cell line development by random integration.

15 Claims, 11 Drawing Sheets

Figure 1:
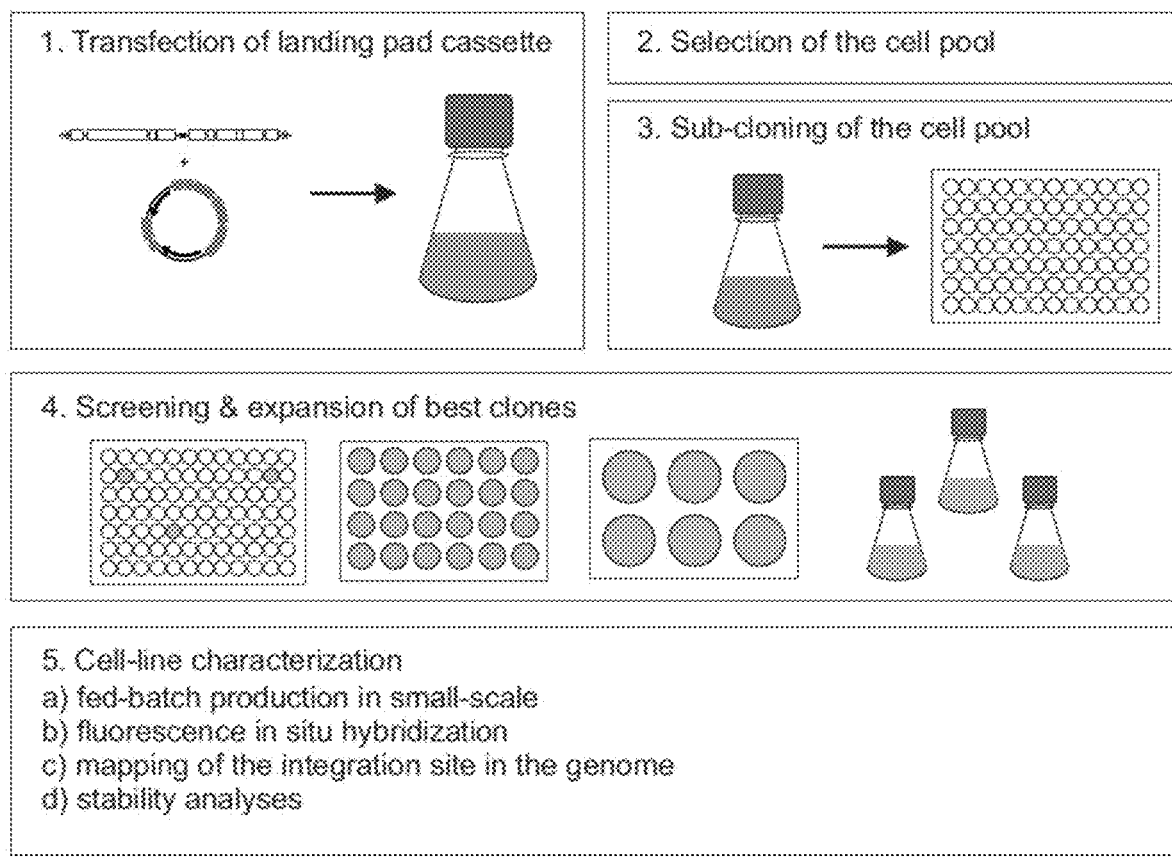

Specification includes a Sequence Listing.

A

| pool no | Recombination plasmid (ng) | recombinase mRNA (mg) |
|---|---|---|
| 1 | 100 | 1 |
| 2 | 300 | 1 |
| 3 | 1000 | 1 |
| 4 | 100 | 3 |
| 5 | 300 | 3 |
| 6 | 1000 | 3 |

B

| Pool no | Recombination plasmid (ng) | recombinase mRNA (µg) | targeted integration (%) | targeted + random integration (%) | random integration, 1-2 integration sites (%) | random integration, <2 integration sites (%) |
|---|---|---|---|---|---|---|
| 1 | 100 | 1 | 21 | 15 | 54 | 10 |
| 2 | 300 | 1 | 26 | 15 | 32 | 27 |
| 3 | 1000 | 1 | 25 | 16 | 21 | 38 |
| 4 | 100 | 3 | 22 | 11 | 55 | 12 |
| 5 | 300 | 3 | 42 | 19 | 21 | 18 |
| 6 | 1000 | 3 | 31 | 24 | 24 | 21 |

SEQUENCE LISTING

```
<160> NUMBER OF SEQ ID NOS: 26

<210> SEQ ID NO 1
<211> LENGTH: 13279
<212> TYPE: DNA
<213> ORGANISM: artificial sequence
<220> FEATURE:
<223> OTHER INFORMATION: chemically synthesized

<400> SEQUENCE: 1
ctaggctttt gcaaaaagct taagcgtacg gtaagtggcg tttctcgggg agccagctgc      60
gtccgctgtc gtgctgtcgg tgtagtacta gcaagcgtta agtccccatc tggctgcggc     120
ctaccgaaga gtggtcttca cgtcacacgc tgtcccacgc agtggttggt ttggtcgctt     180
ctggttactg actactaagc agccttttct tttttccttt cagccaccat gggcgtgaag     240
gtgctgttcg ccctgatctg tatcgccgtg gccgaggcca gcccaccga gaacaatgag     300 gacttcaaca tcgtggccgt ggccagcaac ttcgccacca cagacctgga tgccgacaga     360
```

-continued

| | |
|---|---|
| ggcaagctgc ccggcaagaa actgcccctg gaagtgctga aagagatgga agccaatgcc | 420 |
| agaaaggccg gctgcaccag aggctgcctg atctgcctga ccacatcaa gtgcaccccc | 480 |
| aagatgaaga agttcatccc cggcagatgc cacacctatg agggcgacaa agagtctgcc | 540 |
| cagggcggca tcggcgaggc catcgtggac atccccgaga tccccggctt caaggacctg | 600 |
| gaacccatgg aacagtttat cgcccaggtg gacctgtgcg tggactgcac caccggctgt | 660 |
| ctgaagggcc tggccaacgt gcagtgcagc gacctgctga agaagtggct gccccagaga | 720 |
| tgcgccacct tcgccagcaa gatccagggc caggtggaca agatcaaggg ggctggcggc | 780 |
| gacgcaccgg tgaaacagac tttgaatttt gaccttctca agttggcggg agacgtggag | 840 |
| tccaaccctg ggcccttcga atggtgagc aagggcgagg agctgttcac cggggtggtg | 900 |
| cccatcctgg tcgagctgga cggcgacgta acggccaca agttcagcgt gtccggcgag | 960 |
| ggcgagggcg atgccaccta cggcaagctg accctgaagt tcatctgcac caccggcaag | 1020 |
| ctgcccgtgc cctggcccac cctcgtgacc accctgacct acggcgtgca gtgcttcagc | 1080 |
| cgctaccccg accacatgaa gcagcacgac ttcttcaagt ccgccatgcc cgaaggctac | 1140 |
| gtccaggagc gcaccatctt cttcaaggac gacggcaact acaagacccg cgccgaggtg | 1200 |
| aagttcgagg gcgacaccct ggtgaaccgc atcgagctga agggcatcga cttcaaggag | 1260 |
| gacggcaaca tcctggggca caagctggag tacaactaca acagccacaa cgtctatatc | 1320 |
| atggccgaca agcagaagaa cggcatcaag gtgaacttca gatccgcca caacatcgag | 1380 |
| gacggcagcg tgcagctcgc cgaccactac cagcagaaca cccccatcgg cgacggcccc | 1440 |
| gtgctgctgc ccgacaacca ctacctgagc acccagtccg ccctgagcaa agaccccaac | 1500 |
| gagaagcgcg atcacatggt cctgctggag ttcgtgaccg ccgcgggat cactctcggc | 1560 |
| atggacgagc tgtacaaggc accggtgaaa cagactttga attttgacct tctcaagttg | 1620 |
| gcgggagacg tggagtccaa ccctgggccc atggaagatg ccaaaaacat taagaaaggc | 1680 |
| ccagcgccat tctacccact cgaagacggg accgccggcg agcagctgca caaagccatg | 1740 |
| aagcgctacg ccctggtgcc cggcaccatc gcctttaccg acgcacatat cgaggtggac | 1800 |
| attacctacg ccgagtactt cgagatgagc gttcggctgg cagaagctat gaagcgctat | 1860 |
| gggctgaata caaaccatcg gatcgtggtg tgcagcgaga atagcttgca gttcttcatg | 1920 |
| cccgtgttgg gtgccctgtt catcggtgtg gctgtggccc cagctaacga catctacaac | 1980 |
| gagcgcgagc tgctgaacag catgggcatc agccagccca ccgtcgtatt cgtgagcaag | 2040 |
| aaagggctgc aaaagatcct caacgtgcaa aagaagctac cgatcataca aaagatcatc | 2100 |
| atcatggata gcaagaccga ctaccagggc ttccaaagca tgtacacctt cgtgacttcc | 2160 |
| catttgccac ccggcttcaa cgagtacgac ttcgtgcccg agagcttcga ccgggacaaa | 2220 |
| accatcgccc tgatcatgaa cagtagtggc agtaccggat tgcccaaggg cgtagcccta | 2280 |
| ccgcaccgca ccgcttgtgt ccgattcagt catgcccgcg accccatctt cggcaaccag | 2340 |
| atcatccccg acaccgctat cctcagcgtg gtgccatttc accacggctt cggcatgttc | 2400 |
| accacgctgg gctacttgat ctgcggcttt cgggtcgtgc tcatgtaccg cttcgaggag | 2460 |
| gagctattct tgcgcagctt gcaagactat aagattcaat ctgccctgct ggtgccacac | 2520 |
| ctatttggct tcttcgctaa gagcactctc atcgacaagt acgacctaag caacttgcac | 2580 |
| gagatcgcca gcggcggggc gccgctcagc aaggaggtag gtgaggccgt ggccaaacgc | 2640 |
| ttccacctac caggcatccg ccagggctac ggcctgacga aaacaaccag cgccattctg | 2700 |
| atcacccccg aaggggacga caagcctggc gcagtaggca aggtggtgcc cttcttcgag | 2760 |

```
gctaaggtgg tggacttgga caccggtaag acactgggtg tgaaccagcg cggcgagctg    2820
tgcgtccgtg gccccatgat catgagcggc tacgttaaca accccgaggc tacaaacgct    2880
ctcatcgaca aggacggctg gctgcacagc ggcgacatcg cctactggga cgaggacgag    2940
cacttcttca tcgtgaccg gctgaagagc ctgatcaaat acaagggcta ccaggtagcc     3000
ccagccgaac tggagagcat cctgctgcaa caccccaaca tcttcgacgc cggggtcgcc    3060
ggcctgcccg acgacgatgc cggcgagctg cccgccgcag tcgtcgtgct ggaacacggt    3120
aaaaccatga ccgagaagga gatcgtggac tatgtggcca gccaggttac aaccgccaag    3180
aagctgcgcg tggtgttgt gttcgtggac gaggtgccta aggactgac cggcaagttg       3240
gacgcccgca agatccgcga gattctcatt aaggccaaga agggcggcaa gatcgccgtg    3300
tgaggagatg ggggaggcta actgaaacac ggaaggagac aataccggaa ggaacccgcg    3360
ctatgacggc aataaaaaga cagaataaaa cgcacgggtg ttgggttgtt tgttcataaa     3420
cgcggggttc ggtcccaggg ctggcactct gtcgataccc caccgagacc ccattggggc    3480
caatacgccc gcgtttcttc cttttcccca ccccaccccc caagttcggg tgaaggccca    3540
gggctcgcag ccaatgtcgg ggcggcaggc cctgccatag ccactggccc cgtgggttag    3600
ggacggggtc cccatgggga atggtttatg gttcgtgggg gttattattt tgggtgttgc    3660
gtggggtctg gggcgcgcca taggtacccg atgatcctga cgacggagac cgccgtcgtc    3720
gacaagccct atatttatct aagacgcact ggtatgaaat ttgagattgc agcacattaa    3780
atcacttaga tgaacgagcc gctggtgacg cttagctcct atcattagat aacttcgtat    3840
agcatacatt atacgaagtt atcgcaggta cctataacta tctggtatga tgggactacc    3900
aaaactttac taggttacca atggcacgct ttccctcagc cgaccgaatt agctaggatg    3960
tgatagtcct tagtgaacgt atcaagaatg gaaacagctg attgatacgt ccgaatttat    4020
gttatatttg gcaagattta atttaattaa aaagaattat atttagctgg caattattag    4080
tcttggggcc actcgtcatt tctaaataac tcatgtggca tgttgtacct ttgtcagcaa    4140
tagctcaggc aaggccagtt cttaaggaat taagcctatg attaaggtgt ttcaagagtt    4200
tatatcacta ccgtttgtat ctacactacg atagtacact cttttgaatg gaaccatgg     4260
tgtgatcacc gttatctcat cctctcgata gaagaggaag aggttaatat aactctccat    4320
tggtatgggt aatggtacaa aaccatcttc tcgcgcattg taaggtctat gggcacatta    4380
tcgaacgcct ccctagtccc tagaatgaac cgaccgtaaa acagagccct ttaggatagc    4440
caatcagtag taatctaacg actagccgtc attcacctgc acctgaggca agcttcacgc    4500
tgccgcaagc actcagggcg caagggctgc taaaggaagc ggaacacgta gaaagccagt    4560
ccgcagaaac ggtgctgacc ccggatgaat gtcagctact gggctatctg acaagggaa     4620
aacgcaagcg caaagagaaa gcaggtagct tgcagtgggc ttacatggcg atagctagac    4680
tgggcggttt tatggacagc aagcgaaccg gaattgccag ctggggcgcc ctctggtaag    4740
gttgggaagc cctgcaaagt aaactggatg ctttcttgc cgccaaggat ctgatggcgc      4800
agggatcaa gatctgatca agagacagga tgaggatcgt ttcgcatgat tgaacaagat      4860
ggattgcacg caggttctcc ggccgcttgg gtggagaggc tattcggcta tgactgggca    4920
caacagacaa tcggctgctc tgatgccgcc gtgttccggc tgtcagcgca ggggcgcccg    4980
gttcttttg tcaagaccga cctgtccggt gccctgaatg aactgcagga cgaggcagcg      5040
cggctatcgt ggctggccac gacgggcgtt ccttgcgcag ctgtgctcga cgttgtcact    5100
```

```
gaagcgggaa gggactggct gctattgggc gaagtgccgg ggcaggatct cctgtcatct    5160
caccttgctc ctgccgagaa agtatccatc atggctgatg caatgcggcg gctgcatacg    5220
cttgatccgg ctacctgccc attcgaccac caagcgaaac atcgcatcga gcgagcacgt    5280
actcggatgg aagccggtct tgtcgatcag gatgatctgg acgaagagca tcaggggctc    5340
gcgccagccg aactgttcgc caggctcaag gcgcgcatgc ccgacggcga ggatctcgtc    5400
gtgacccatg gcgatgcctg cttgccgaat atcatggtgg aaaatggccg cttttctgga    5460
ttcatcgact gtggccggct gggtgtggcg gaccgctatc aggacatagc gttggctacc    5520
cgtgatattg ctgaagagct tggcggcgaa tgggctgacc gcttcctcgt gctttacggt    5580
atcgccgctc ccgattcgca gcgcatcgcc ttctatcgcc ttcttgacga gttcttctga    5640
gcgggactct ggggttcgca tcgatgcatc gatgcggcgg gtgtggtggt tacgcgtaat    5700
ctgctgcttg caaacaaaaa aaccaccgct accagcggtg gtttgtttgc cggatcaaga    5760
gctaccaact cttttccga aggtaactgg cttcagcaga gcgcagatac caaatactgt    5820
tcttctagtg tagccgtagt taggccacca cttcaagaac tctgtagcac cgcctacata    5880
cctcgctctg ctaatcctgt taccagtggc tgctgccagt ggcgataagt cgtgtcttac    5940
cgggttggac tcaagacgat agttaccgga taaggcgcag cggtcgggct gaacggggggg    6000
ttcgtgcaca cagcccagct tggagcgaac gacctacacc gaactgagat acctacagcg    6060
tgagctatga gaaagcgcca cgcttcccga agggagaaag gcggacaggt atccggtaag    6120
cggcagggtc ggaacaggag agcgcacgag ggagcttcca gggggaaacg cctggtatct    6180
ttatagtcct gtcgggtttc gccacctctg acttgagcgt cgattttgt gatgctcgtc    6240
agggggggcgg agcctatgga aaaacgccag caacgcatcg ataaaataaa agattttatt    6300
tagtctccag aaaaagggg gaatgaaaga ccccacctgt aggtttggca agctaggtgg    6360
cggccgcaaa aagcaggtgt tgcaactata tagagtcttg atgaccaacg taaacctagg    6420
cctttctaca gggattgtat aaagcctagc aatgagaaga tcacctctgg tagtaaatat    6480
ctttgaggtt atattgtcga tatcttcatc ttcgatgcgc cgtagtttag aagtcataag    6540
tcgataacac gagcgtactg ttagattcct tatacgtttc aaagagagcg ttagtacaca    6600
gaggcgcagg tcaatgctag gaagctacgg gcgacgctga ccgtctctaa ctgtcaacaa    6660
agttataatg aagcaatcat gaattttatc taagtagaga ttatgttcat agtcaccttc    6720
agaagagcta tactcagagg cacgccattt ataagcctat ctagtagaag aattgtggga    6780
ttgtacctac accgagctcc tcctgcttaa cccattctgt atttttgatt aaataactac    6840
gtattacata gtcactttgc gcaaggaaaa atagtgcttt tccgtctatg taaagactaa    6900
tcatatcatt agcgaacgcc ttcctcgttt aggcgtctac tgatagctat cgtactggtc    6960
tgcagcacgt gagcataact tcgtataatg tatgctatac gaagttatag ttcttagcat    7020
tataataagg caggcaatta cttatatcag tcaagtttca aacttagtca gccgggttga    7080
gaacggttta gatccacccc gttatgacgg cttgtcgacg acggcggtct ccgtcgtcag    7140
gatcatacca cgtggtcctg ctattgtctt cccaatcctc ccccttgctg tcctgcccca    7200
ccccaccccc cagaatagaa tgacacctac tcagacaatg cgatgcaatt tcctcatttt    7260
attaggaaag gacagtggga gtggcacctt ccagggtcaa ggaaggcacg ggggagggggc    7320
aaacaacaga tggctggcaa ctagaaggca cagtcgaggc taatcagcgt cagttagcct    7380
cccccatctc ccgatccgga cgagtgctgg ggcgtcggtt ccactatcg gcgagtactt    7440
ctacacagcc atcggtccag acggccgcgc ttctgcgggc gatttgtgta cgcccgacag    7500
```

```
tcccggctcc ggatcggacg attgcgtcgc atcgaccctg cgcccaagct gcatcatcga   7560
aattgccgtc aaccaagctc tgatagagtt ggtcaagacc aatgcggagc atatacgccc   7620
ggagccgcgg cgatcctgca agctccggat gcctccgctc gaagtagcgc gtctgctgct   7680
ccatacaagc caaccacggc ctccagaaga agatgttggc gacctcgtat tgggaatccc   7740
cgaacatcgc ctcgctccag tcaatgaccg ctgttatgcg gccattgtcc gtcaggacat   7800
tgttggagcc gaaatccgcg tgcacgaggt gccggacttc ggggcagtcc tcggcccaaa   7860
gcatcagctc atcgagagcc tgcgcgacgg acgcactgac ggtgtcgtcc atcacagttt   7920
gccagtgata cacatgggga tcagcaatcg cgcatatgaa atcacgccat gtagtgtatt   7980
gaccgattcc ttgcggtccg aatgggccga acccgctcgt ctggctaaga tcggccgcag   8040
cgatcgcatc catggcctcc gcgaccggct gcagaacagc gggcagttcg gtttcaggca   8100
ggtcttgcaa cgtgacaccc tgtgcacggc gggagatgca ataggtcagg ctctcgctga   8160
attccccaat gtcaagcact tccggaatcg ggagcgcggc cgatgcaaag tgccgataaa   8220
cataacgatc tttgtagaaa ccatcggcgc agctatttac ccgcaggaca tatccacgcc   8280
ctcctacatc gaagctgaaa gcacgagatt cttcgccctc cgagagctgc atcaggtcgg   8340
agacgctgtc gaacttttcg atcagaaact tctcgacaga cgtcgcggtg agttcaggct   8400
ttttgggccc agggttggac tccacgtctc ccgccaactt gagaaggtca aaattcaaag   8460
tctgtttcac cggtgctgtc tgctcgaagc ggccggccgc cccgactcta gagtaacccg   8520
ggtgcgcggc gtcggtggtg ccggcgggg cgccaggtc gcaggcggtg tagggctcca   8580
ggcaggcggc gaaggccatg acgtgcgcta tgaaggtctg ctcctgcacg ccgtgaacca   8640
ggtgcgcctg cgggccgcgc gcgaacaccg ccacgtcctc gcctgcgtgg gtctcttcgt   8700
ccaggggcac tgctgactgc tgccgatact cggggctccc gctctcgctc tcggtaacat   8760
ccggccgggc gccgtccttg agcacatagc ctggaccgtt tccgtatagg aggaccgtgt   8820
aggccttcct gtcccgggcc ttgccagggg ccagcccgaa gatggagctc cctcgcaggg   8880
ggtagcctcc gaaggagaag acgtgggagt ggtcggcagt gacgaggctc agcgtgtcct   8940
cctcgctggt gagctggccc gccctctcaa tggcgtcgtc gaacatgatc gtctcagtca   9000
gtgcccggta agccctgctt tcatgatgac catggtcgat gcgaccaccc tccacgaaga   9060
ggaagaagcc gcggggttc ctgctcagca ggcgcagggc agcctctgtc atctccatca   9120 gggagggtc cagtgtggag tctcggtgga tctcgtattt catgtctcca ggctcaaaga   9180
gacccatgag atgggtcaca gacgggtcca gggaagcctg catgagctca gtgcggttcc   9240
acacataccg ggcaccctgg cgcttcgcca gccattcctg caccagattc ttcccgtcca   9300
gcctggtccc accttggctg tagtcatctg ggtactcagg gtctggggtt cccatgcgaa   9360
acatgtactt tcggcctcca cctaggatca cgtcaatgtc catgttggag atgagctgcg   9420
tagcgatgtc ctggcacccc tcctggcggg ccgaggcagg cacgtcggcg tccgagtacc   9480
agttgcggtt caccgtgtgg gcgtaggtgc cggctggcga ggcgtgctgc actcgtgtgg   9540
tggttaccac tcccactgac ttccctgctt tcttggcccg attcatcacg gagatgacct   9600
cgttgccgcg tgtcgtgttg cactggttaa agcgggcggc tgcactcaag ccaatggtct   9660
ggaagttgcc cttgaccccg cacaggtagg ccgtggctgt ggctccactg tctggcacat   9720
gtttgtctac attgtatgtc ttggacagag ccacatatgg gaagcggtcc atggccaggg   9780
gtatctcagg ccccagtttg tccttcttct gcccttttag gatcctggca gctgtcaccg   9840
```

```
tagacacccc catcccatcg cccaggaaga tgatgaggtt cttggcggct gtctgtgcag    9900
gctgcagctt cttggcggca cccagggcct cggctgcctc gcggttccag aagtccgggt    9960
tctcctcctc aactgggatg atgcccaggg agagctgtag cctcaggccc agcagcagca   10020
gcagcagcag catggtggat gcggccgctc tagacacgac acctgaaatg gaagaaaaaa   10080
actttgaacc actgtctgag gcttgagaat gaaccaagat ccaaactcaa aaagggcaaa   10140
ttccaaggag aattacatca agtgccaagc tggcctaact tcagtctcca cccactcagt   10200
gtggggaaac tccatcgcat aaaaccctc cccccaacct aaagacgacg tactccaaaa    10260
gctcgagaac taatcgaggt gcctggacgg cgcccggtac tccgtggagt cacatgaagc   10320
gacggctgag gacggaaagg ccctttttcct ttgtgtgggt gactcacccg cccgctctcc   10380
cgagcgccgc gtcctccatt ttgagctccc tgcagcaggg ccgggaagcg gccatctttc   10440
cgctcacgca actggtgccg accgggccag ccttgccgcc cagggcgggg cgatacacgg   10500
cggcgcgagg ccaggcacca gagcaggccg gccagcttga gctaccccc gtccgattct    10560
cggtggccgc gctcgcaggc cccgcctcgc cgaacatgtg cgctgggacg cacgggcccc   10620
gtcgccgccc gcggcccaa aaaccgaaat accagtgtgc agatcttggc ccgcatttac    10680
aagactatct tgccagaaaa aaagcgtcgc agcaggtcat caaaaatttt aaatggctag   10740
agacttatcg aaagcagcga gacaggcgcg aaggtgccac cagattcgca cgcggcggcc   10800
ccagcgccca agccaggcct caactcaagc acgaggcgaa ggggctcctt aagcgcaagg   10860
cctcgaactc tcccacccac ttccaacccg aagctcggga tcaagaatca cgtactgcag   10920
ccaggggcgt ggaagtaatt caaggcacgc aagggccata acccgtaaag aggccaggcc   10980
cgcgggaacc acacacggca cttacctgtg ttctggcgtc tagagtcgac tagcttttaa   11040
gcgggtcgct gcagggtcgc tcggtgttcg aggccacacg cgtcaccttaa atatgcgaag   11100
tggacctggg accgcgccgc cccgactgca tctgcgtgtt cgaattcgcc aatgacaaga   11160
cgctgggcgg ggtttgtgtc atcatagaac taaagacatg caaatatatt tcttccgggg   11220
acaccgccag caaacgcgag caacgggcca cggggatgaa gcagctgcgc cactccctga   11280
agctcctgca gtccctcgcg cctccggggtg acaagatagt gtacctgtgc cccgtcctgg   11340
tgtttgtcgc ccaacggacg ctccgcgtca gccgcgtgac ccggctcgtc ccgcagaagg   11400
tctccggtaa tatcaccgca gtcgtgcgga tgctccagag cctgtccacg tatacggtcc   11460
ccatggagcc taggacccag cgagcccgtc gccgccgcgg cggcgccgcc cggggggtctg  11520
cgagcagacc gaaaaggtca cactctgggg cgcgcgaccc gcccgagtca gcggcccgcc   11580
agttaccacc cgccgaccaa accccgcct ccacggaggg cgggggggtg cttaagagga    11640
tcgcggcgct cttctgcgtg cccgtggcca ccaagaccaa accccgagcc gcctccgaat   11700
gagagtgttt cgttccttcc ccctccccc gcgtcagaca aaccctaacc accgcttaag    11760
cggcccccgc gaggtccgaa gactcattta gatctaagct attctcagct gccatggaaa   11820
atcgataccg tcttcgctag aactagtcta atgttgccat gggtagcata tactacccaa   11880
atatctggat agcatatgct atcctaatct atatctgggt agcataggct atcctaatct   11940
atatctgggt agcatatgct atcctaatct atatctgggt agtatatgct atcctaatttt  12000
atatctgggt agcataggct atcctaatct atatctgggt agcatatgct atcctaatct   12060
atatctgggt agtatatgct atcctaatct gtatccgggt agcatatgct atcctaatag   12120
agattagggt agtatatgct atcctaattt atatctgggt agcatatact acccaaatat   12180
ctggatagca tatgctatcc taatctatat ctgggtagca tatgctatcc taatctatat   12240
```

-continued

```
ctgggtagca taggctatcc taatctatat ctgggtagca tatgctatcc taatctatat      12300
ctgggtagta tatgctatcc taatttatat ctgggtagca taggctatcc taatctatat      12360
ctgggtagca tatgctatcc taatctatat ctgggtagta tatgctatcc taatctgtat      12420
ccgggtagca tatgctatcc tcatgcgtat acagtcagca tatgataccc gactagtgga      12480
tcccccgggc tgcaggaatt cgatggggat ctgtaccgtt gccggtcgga tctgtaccgt      12540
tgccggtcgg atctgtaccg ttgccggtcg gatctgtacc gttgccggtc ggatctgtac      12600
cgttgccggt cggatctgta ccgttgccgg tcggatctgt accgttgccg gtcggatctg      12660
taccgttgcc ggtcggatct gtaccgttgc cggtcggatc tgtaccgttg ccggtcggat      12720
cagcttcaga agatggcgga gggcctccaa cacagtaatt ttcctcccga cagatctcct      12780
agaatgtttc cacccaatca ttactatgac aacagctgtt ttttttagta ttaagcagag      12840
gccgggggcc cctggcctcc gcttactctg agaaaaaga agagaggcat tgtagaggct      12900
tccagaggca acttgtcaaa acaggactgg cgacctgcag gcatgcaagc tgaccctgtg      12960
gaatgtgtgt cagttagggt gtggaaagtc cccaggctcc ccagcaggca aagtatgca      13020 aagcatgcat ctcaattagt cagcaaccag gtgtggaaag tccccaggct ccccagcagg      13080
cagaagtatg caaagcatgc atctcaatta gtcagcaacc atagtcccgc ccctaactcc      13140
gcccatcccg ccctaactc cgcccagttc cgcccattct ccgccccatg gctgactaat      13200 ttttttatt tatgcagagg ccgaggccgc ctcggcctct gagctattcc agaagtagtg      13260
aggaggcttt tttggaggc                                                   13279

<210> SEQ ID NO 2
<211> LENGTH: 11795
<212> TYPE: DNA
<213> ORGANISM: artificial sequence
<220> FEATURE:
<223> OTHER INFORMATION: chemically synthetizised

<400> SEQUENCE: 2
cgcgccatag gtaccggctt gtcgacgacg gcggtctccg tcgtcaggat catctaatga        60
taggagctaa gcgtcaccag cggctcgttc atctaagtga tttgaagttc ctatactttc       120
tagagaatag gaacttcgga ataggaactt caatgtgctg caatctcaaa tttcatacca       180
gtgcgtctta gataaatata gataacttcg tataggatac tttatacgaa gttatggtac       240
ctataactat ctggtatgat gggactacca aaactttact aggttaccaa tggcacgctt       300
tccctcagcc gaccgaatta gctaggatgt gatagtcctt agtgaacgta tcaagaatgg       360
aaacagctga ttgatacgtc cgaatttatg ttatatttgg caagatttaa tttaattaaa       420
aagaattata tttagctggc aattattagt cttgggccca ctcgtcattt ctaaataact       480
catgtggcat gttgtacctt tgtcagcaat agctcaggca aggccagttc ttaaggaatt       540
aagcctatga ttaaggtgtt tcaagagttt atatcactac cgtttgtatc tacactacga       600
tagtacactc ttttgaatgg gaaccatggt gtgatcaccg ttatctcatc ctctcgatag       660
aagaggaaga ggttaatata actctccatt ggtatgggta atggtacaaa accatcttct       720
cgcgcattgt aaggtctatg ggcacattat cgaacgcctc cctagtccct agaatgaacc       780
gaccgtaaaa cagagcccctt taggatagcc aatcagtagt aatctaacga ctagccgtca       840
ttaatgcttc acgctgccgc aagcactcag ggcgcaaggg ctgctaaagg aagcggaaca       900
cgtagaaagc cagtccgcag aaacggtgct gaccccggat gaatgtcagc tactgggcta       960
```

```
tctggacaag ggaaaacgca agcgcaaaga gaaagcaggt agcttgcagt gggcttacat    1020
ggcgatagct agactgggcg gttttatgga cagcaagcga accggaattg ccagctgggg    1080
cgccctctgg taaggttggg aagccctgca aagtaaactg gatggctttc ttgccgccaa    1140
ggatctgatg gcgcagggga tcaagatctg atcaagagac aggatgagga tcgtttcgca    1200
tgattgaaca agatggattg cacgcaggtt ctccggccgc ttgggtggag aggctattcg    1260
gctatgactg ggcacaacag acaatcggct gctctgatgc cgccgtgttc cggctgtcag    1320
cgcaggggcg cccggttctt tttgtcaaga ccgacctgtc cggtgccctg aatgaactgc    1380
aggacgaggc agcgcggcta tcgtggctgg ccacgacggg cgttccttgc gcagctgtgc    1440
tcgacgttgt cactgaagcg ggaagggact ggctgctatt gggcgaagtg ccggggcagg    1500
atctcctgtc atctcacctt gctcctgccg agaaagtatc catcatggct gatgcaatgc    1560
ggcggctgca tacgcttgat ccggctacct gcccattcga ccaccaagcg aaacatcgca    1620
tcgagcgagc acgtactcgg atggaagccg gtcttgtcga tcaggatgat ctggacgaag    1680
agcatcaggg gctcgcgcca gccgaactgt tcgccaggct caaggcgcgc atgcccgacg    1740
gcgaggatct cgtcgtgacc catggcgatg cctgcttgcc gaatatcatg gtggaaaatg    1800
gccgcttttc tggattcatc gactgtggcc ggctgggtgt ggcggaccgc tatcaggaca    1860
tagcgttggc tacccgtgat attgctgaag agcttggcgg cgaatgggct gaccgcttcc    1920
tcgtgcttta cggtatcgcc gctcccgatt cgcagcgcat cgccttctat cgccttcttg    1980
acgagttctt ctgagcggga ctctggggtt cgcatcgatg catcgatgcg gcgggtgtgg    2040
tggttacgcg taatctgctg cttgcaaaca aaaaaaccac cgctaccagc ggtggtttgt    2100
ttgccggatc aagagctacc aactcttttt ccgaaggtaa ctggcttcag cagagcgcag    2160
ataccaaata ctgttcttct agtgtagccg tagttaggcc accacttcaa gaactctgta    2220
gcaccgccta catacctcgc tctgctaatc ctgttaccag tggctgctgc cagtggcgat    2280
aagtcgtgtc ttaccgggtt ggactcaaga cgatagttac cggataaggc gcagcggtcg    2340
ggctgaacgg ggggttcgtg cacacagccc agcttggagc gaacgaccta caccgaactg    2400
agatacctac agcgtgagct atgagaaagc gccacgcttc ccgaagggag aaaggcggac    2460
aggtatccgg taagcggcag ggtcggaaca ggagagcgca cgagggagct tccaggggga    2520
aacgcctggt atctttatag tcctgtcggg tttcgccacc tctgacttga gcgtcgattt    2580
ttgtgatgct cgtcaggggg gcggagccta tggaaaaacg ccagcaacgc atcgataaaa    2640
taaaagattt tatttagtct ccagaaaaag ggggaatga agacccccac ctgtaggttt    2700
ggcaagctag gtggcggccg cattaatgtt gcaactatat agagtcttga tgaccaacgt    2760
aaacctaggc ctttctacag ggattgtata aagcctagca atgagaagat cacctctggt    2820
agtaaatatc tttgaggtta tattgtcgat atcttcatct tcgatgcgcc gtagtttaga    2880
agtcataagt cgataacacg agcgtactgt tagattcctt atacgtttca aagagagcgt    2940
tagtacacag aggcgcaggt caatgctagg aagctacggg cgacgctgac cgtctctaac    3000
tgtcaacaaa gttataatga agcaatcatg aattttatct aagtagagat tatgttcata    3060
gtcaccttca gaagagctat actcagaggc acgccattta taagcctatc tagtagaaga    3120
attgtgggat tgtacctaca ccgagctcct cctgcttaac ccattctgta ttttttgatta    3180 aataactacg tattacatag tcactttgcg caaggaaaaa tagtgctttt ccgtctatgt    3240
aaagactaat catatcatta gcgaacgcct tcctcgttta ggcgtctact gatagctatc    3300
gtactggtct gcagcacgtg atgatcctga cgacggagac cgccgtcgtc gacaagccct    3360
```

```
aatgatagga gctaagcgtc accagcggct cgttcatcta agtgatttga agttcctata    3420 cttttttgaag aataggaact tcggaatagg aacttcaatg tgctgcaatc tcaaatttca    3480
taccagtgcg tcttagataa atatagataa cttcgtataa tgtatgctat acgaagttat    3540
cacgtggtcc tgctattgtc ttcccaatcc tcccccttgc tgtcctgccc caccccaccc    3600
cccagaatag aatgacacct actcagacaa tgcgatgcaa tttcctcatt ttattaggaa    3660
aggacagtgg gagtggcacc ttccagggtc aaggaaggca cggggagggg caaacaaca    3720 gatggctggc aactagaagg cacagtcgag gctaatcagc gtcagttagc ctcccccatc    3780
tcccgatccg gacgagtgct ggggcgtcgg tttccactat cggcgagtac ttctacacag    3840
ccatcggtcc agacggccgc gcttctgcgg gcgatttgtg tacgcccgac agtcccggct    3900
ccggatcgga cgattgcgtc gcatcgaccc tgcgcccaag ctgcatcatc gaaattgccg    3960
tcaaccaagc tctgatagag ttggtcaaga ccaatgcgga gcatatacgc ccggagccgc    4020
ggcgatcctg caagctccgg atgcctccgc tcgaagtagc gcgtctgctg ctccatacaa    4080
gccaaccacg gcctccagaa gaagatgttg gcgacctcgt attgggaatc cccgaacatc    4140
gcctcgctcc agtcaatgac cgctgttatg cggccattgt ccgtcaggac attgttggag    4200
ccgaaatccg cgtgcacgag gtgccggact tcggggcagt cctcggccca aagcatcagc    4260
tcatcgagag cctgcgcgac ggacgcactg acggtgtcgt ccatcacagt ttgccagtga    4320
tacacatggg gatcagcaat cgcgcatatg aaatcacgcc atgtagtgta ttgaccgatt    4380
ccttgcggtc cgaatgggcc gaacccgctc gtctggctaa gatcggccgc agcgatcgca    4440
tccatggcct ccgcgaccgg ctgcagaaca gcgggcagtt cggtttcagg caggtcttgc    4500
aacgtgacac cctgtgcacg gcgggagatg caataggtca ggctctcgct gaattcccca    4560
atgtcaagca cttccggaat cgggagcgcg gccgatgcaa agtgccgata aacataacga    4620
tctttgtaga aaccatcggc gcagctattt acccgcagga catatccacg ccctcctaca    4680
tcgaagctga aagcacgaga ttcttcgccc tccgagagct gcatcaggtc ggagacgctg    4740 tcgaacttttt cgatcagaaa cttctcgaca gacgtcgcgg tgagttcagg ctttttgggc    4800
ccagggttgg actccacgtc tcccgccaac ttgagaaggt caaaattcaa agtctgtttc    4860
accggtgctg tctgctcgaa gcggccggcc gccccgactc tagagtaacc cgggtgcgcg    4920
gcgtcggtgg tgccggcggg gggcgccagg tcgcaggcgg tgtagggctc caggcaggcg    4980
gcgaaggcca tgacgtgcgc tatgaaggtc tgctcctgca cgccgtgaac caggtgcgcc    5040
tgcgggccgc gcgcgaacac cgccacgtcc tcgcctgcgt gggtctcttc gtccaggggc    5100
actgctgact gctgccgata ctcggggctc ccgctctcgc tctcggtaac atccggccgg    5160
gcgccgtcct tgagcacata gcctggaccg tttccgtata ggaggaccgt gtaggccttc    5220
ctgtcccggg ccttgccagg ggccagcccg aagatggagc tccctcgcag ggggtagcct    5280
ccgaaggaga agacgtggga gtggtcggca gtgacgaggc tcagcgtgtc ctcctcgctg    5340
gtgagctggc ccgccctctc aatggcgtcg tcgaacatga tcgtctcagt cagtgcccgg    5400
taagccctgc tttcatgatg accatggtcg atgcgaccac cctccacgaa gaggaagaag    5460
ccgcgggggt tcctgctcag caggcgcagg gcagcctctg tcatctccat cagggagggg    5520
tccagtgtgg agtctcggtg gatctcgtat tcatgtctc caggctcaaa gagacccatg    5580
agatgggtca cagacgggtc cagggaagcc tgcatgagct cagtgcggtt ccacacatac    5640
cgggcaccct ggcgcttcgc cagccattcc tgcaccagat tcttcccgtc cagcctggtc    5700
```

```
ccaccttggc tgtagtcatc tgggtactca gggtctgggg ttcccatgcg aaacatgtac    5760
tttcggcctc cacctaggat cacgtcaatg tccatgttgg agatgagctg cgtagcgatg    5820
tcctggcacc cctcctggcg ggccgaggca ggcacgtcgg cgtccgagta ccagttgcgg    5880
ttcaccgtgt gggcgtaggt gccggctggc gaggcgtgct gcactcgtgt ggtggttacc    5940
actcccactg acttccctgc tttcttggcc cgattcatca cggagatgac ctcgttgccg    6000
cgtgtcgtgt tgcactggtt aaagcgggcg gctgcactca agccaatggt ctggaagttg    6060
cccttgaccc cgcacaggta ggccgtggct gtggctccac tgtctggcac atgtttgtct    6120
acattgtatg tcttggacag agccacatat gggaagcggt ccatggccag gggtatctca    6180
ggccccagtt tgtccttctt ctgccctttt aggatcctgg cagctgtcac cgtagacacc    6240
cccatcccat cgcccaggaa gatgatgagg ttcttggcgg ctgtctgtgc aggctgcagc    6300
ttcttggcgg cacccagggc ctcggctgcc tcgcggttcc agaagtccgg gttctcctcc    6360
tcaactggga tgatgcccag ggagagctgt agcctcaggc ccagcagcag cagcagcagc    6420
agcatggtgg atgcggccgc tctagacacg acacctgaaa tggaaggaaa aaactttgaa    6480
ccactgtctg aggcttgaga atgaaccaag atccaaactc aaaaagggca aattccaagg    6540
agaattacat caagtgccaa gctggcctaa cttcagtctc cacccactca gtgtggggaa    6600
actccatcgc ataaaacccc tcccccaac ctaaagacga cgtactccaa aagctcgaga    6660
actaatcgag gtgcctggac ggcgcccggt actccgtgga gtcacatgaa gcgacggctg    6720
aggacggaaa ggccctttc ctttgtgtgg gtgactcacc cgcccgctct cccgagcgcc    6780
gcgtcctcca ttttgagctc cctgcagcag ggccgggaag cggccatctt tccgctcacg    6840
caactggtgc cgaccgggcc agccttgccg cccagggcgg ggcgatacac ggcggcgcga    6900
ggccaggcac cagagcaggc cggccagctt gagactaccc ccgtccgatt ctcggtggcc    6960
gcgctcgcag gccccgcctc gccgaacatg tgcgctggga cgcacgggcc ccgtcgccgc    7020
ccgcggcccc aaaaaccgaa ataccagtgt gcagatcttg gcccgcattt acaagactat    7080
cttgccagaa aaaagcgtc gcagcaggtc atcaaaaatt ttaaatggct agagacttat    7140
cgaaagcagc gagacaggcg cgaaggtgcc accagattcg cacgcggcgg ccccagcgcc    7200
caagccaggc ctcaactcaa gcacgaggcg aaggggctcc ttaagcgcaa ggcctcgaac    7260
tctcccaccc acttccaacc cgaagctcgg gatcaagaat cacgtactgc agccaggggc    7320
gtggaagtaa ttcaaggcac gcaagggcca taacccgtaa agaggccagg cccgcgggaa    7380
ccacacacgg cacttacctg tgttctggcg tctagagtcg actagctttt aagcgggtcg    7440
ctgcagggtc gctcggtgtt cgaggccaca cgcgtcacct taatatgcga agtggacctg    7500
ggaccgcgcc gccccgactg catctgcgtg ttcgaattcg ccaatgacaa dacgctgggc    7560 gggtttgtg tcatcataga actaaagaca tgcaaatata tttcttccgg ggacaccgcc    7620
agcaaacgcg agcaacgggc cacggggatg aagcagctgc gccactccct gaagctcctg    7680
cagtccctcg cgcctccggg tgacaagata tgtgtacctgt gccccgtcct ggtgtttgtc    7740
gcccaacgga cgctccgcgt cagccgcgtg accggctcg tcccgcagaa ggtctccggt    7800
aatatcaccg cagtcgtgcg gatgctccag agcctgtcca cgtatacggt ccccatggag    7860
cctaggaccc agcgagcccg tcgccgccgc ggcggcgccc ccgggggtc tgcgagcaga    7920 ccgaaaaggt cacactctgg ggcgcgcgac ccgcccgagt cagcggcccg ccagttacca    7980
cccgccgacc aaaccccgc ctccacgag ggcgggggg tgcttaagag gatcgcggcg    8040
ctcttctgcg tgcccgtggc caccaagacc aaaccccgag ccgcctccga atgagagtgt    8100
```

```
ttcgttcctt cccctccc ccgcgtcaga caaaccctaa ccaccgctta agcggcccc     8160
gcgaggtccg aagactcatt tagatctaag ctattctcag ctgccatgga aaatcgatac   8220
cgtcttcgct agaactagtc taatgttgcc atgggtagca tatactaccc aaatatctgg   8280
atagcatatg ctatcctaat ctatatctgg gtagcatagg ctatcctaat ctatatctgg   8340
gtagcatatg ctatcctaat ctatatctgg gtagtatatg ctatcctaat ttatatctgg   8400
gtagcatagg ctatcctaat ctatatctgg gtagcatatg ctatcctaat ctatatctgg   8460
gtagtatatg ctatcctaat ctgtatccgg gtagcatatg ctatcctaat agagattagg   8520
gtagtatatg ctatcctaat ttatatctgg gtagcatata ctacccaaat atctggatag   8580
catatgctat cctaatctat atctgggtag catatgctat cctaatctat atctgggtag   8640
cataggctat cctaatctat atctgggtag catatgctat cctaatctat atctgggtag   8700
tatatgctat cctaatttat atctgggtag cataggctat cctaatctat atctgggtag   8760
catatgctat cctaatctat atctgggtag tatatgctat cctaatctgt atccgggtag   8820
catatgctat cctcatgcgt atacagtcag catatgatac ccgactagtg gatcctgctg   8880
taccgttgcc ggtcggatct gtaccgttgc cggtcggatc tgtaccgttg ccggtcggat   8940
ctgtaccgtt gccggtcgga tctgtaccgt tgccggtcgg atctgtaccg ttgccggtcg   9000
gatctgtacc gttgccggtc ggatctgtac cgttgccggt cggatctgta ccgttgccgg   9060
tcatcctgca ggtcgatcga ctctagtatg gtgcactctc agtacaatct gctctgatgc   9120
cgcatagtta agccagtatc tgctccctgc ttgtgtgttg gaggtcgctg agtagtgcgc   9180
gagcaaaatt taagctacaa caaggcaagg cttgaccgac aattgcatga agaatctgct   9240
tagggttagg cgttttgcgc tgcttcgcga tgtacgggcc agatatacgc gtatctgagg   9300
ggactagggt gtgtttaggc gaaaagcggg gcttcggttg tacgcggtta ggagtcccct   9360
caggatatag tagtttcgct tttgcatagg gagggggaaa tgtagtctta tgcaatactc   9420
ttgtagtctt gcaacatggt aacgatgagt tagcaacatg ccttacaagg agagaaaaag   9480
caccgtgcat gccgattggt ggaagtaagg tggtacgatc gtgccttatt aggaaggcaa   9540
cagacgggtc tgacatggat tggacgaacc actgaattcc gcattgcaga gatattgtat   9600
ttaagtgcct agctcgatac aataaacgcc atttgaccat tcaccacatt ggtgtgcacc   9660
tccaagctgg tagaggatcg gtcgatcgac tctagacagg taagtggcgt ttctcgggga   9720
gccagctgcg tccgctgtcg tgctgtcggt gtagtactag caagcgttaa gtccccatct   9780
ggctgcggcc taccgaagag tggtcttcac gtcacacgct gtcccacgca cgtggttggt   9840
ttggtcgctt ctggttactg actactaagc agccttttct tttttccttt caggttctag   9900
agcggccgcc accgaaacgc cgtacgccac catgagtggg tcttgggtgt tcctgttctt   9960
tctgtccgtg accacaggcg tccacagcca gtcggtggag gagtccgggg gaggcctggt  10020
caagcctgag ggatccctga cactcacctg cacagcctct ggattctcct tcagttccaa  10080
ctactggata tgctgggtcc gccaggctcc ggggaagggg ctggagtgga tcgcatgcat  10140
ttatgctggt agtgatagta ccactgacta cgcgagctgg gcgaaaggcc gattcaccat  10200
ctccaaaacc tcgtcgacca cggtgactct gcaaatgacc agtctgacag ccgcggacac  10260
ggccacctat ttctgtgcga gaggtactga tcgtagtgct gactacttta acttgtgggg  10320
cccaggcacc ctggtcacca tctcttcagc tggaggaggc ggtagtggtg gtggtggatc  10380
tggtggtggt ggatccgccg atctgaccca gactccagcc tcgatgtctg cagctgtggg  10440
```

```
aggcacagtc accatcaact gccaggccag tcagagtgtt agtagtaaca accgcttagc   10500
ctggtatcag cagaaaccag ggcagcctcc caagctcctt atctacaggg catccactct   10560
ggcatctggg gtcccatcgc ggttcaaagg cagtggatct gggacacagt tcactctcac   10620
catcagcgac ctggagtgtg ccgatgctgc cacttactac tgtcagagct attattgggg   10680
tagtagtaat agttataatt cctgggcttt cggcggaggg accgaggtgg tcgtcaaagg   10740
tgctgacaag acccacacct gtcccccttg ccctgctcct gagctgctgg gaggccctag   10800
cgtgttcctg tttcccccta gcccaaggac accctgatga tctccagga ccccgaagt    10860 gacctgcgtg gtggtggatg tgagccacga ggacctgag gtgaagttca actggtacgt    10920
ggacggcgtg gaggtccaca cgccaagac aaaacccagg gaggagcagt acaacagcac    10980
atatcgggtg gtgagcgtgc tgaccgtgct gcaccaggac tggctgaacg gcaaggagta   11040
caagtgcaag gtgtccaaca aggccctccc cgcccccatt gagaagacca tctccaaggc   11100
caagggccag cctagggagc cccaggtgta cacactgcct cccagcaggg acgagctgac   11160
caagaaccag gtgagcctga cctgcctggt gaagggcttc taccctccg atatcgccgt    11220 ggagtgggag tccaatggcc agcccgaaaa caactacaag accaccccc ctgtgctgga    11280 ctccgatggc agcttcttcc tctactccaa gctgaccgtg gacaagtccc ggtggcagca   11340
gggcaacgtg ttcagctgtt ccgtgatgca cgaggccctg cacaaccatt acacccagaa   11400
gtccctgagc ctgtcccccg gaaatgatg gggcgcgccg cttcgaagcg acttttgtcc    11460
cgaattcctg cagcccctag ctagtctttc cgatcgatgg aaggatccgt cggagctcta   11520
ccttgcggcc gcgacatgat aagatacatt gatgagtttg gacaaaccac aactagaatg   11580
cagtgaaaaa aatgctttat ttgtgaaatt tgtgatgcta ttgctttatt tgtgaaattt   11640
gtgatgctat tgctttattt gtaaccatta taagctgcaa taaacaagtt aacaacaaca   11700
attgcattca ttttatgttt caggttcagg gggaggtgtg ggaggttttt taaagcaagt   11760
aaaacctcta caaatgtggt agatcatttg acccg                             11795

<210> SEQ ID NO 3
<211> LENGTH: 10963
<212> TYPE: DNA
<213> ORGANISM: artificial sequence
<220> FEATURE:
<223> OTHER INFORMATION: chemically synthesized

<400> SEQUENCE: 3
cgcgccatag gtaccggctt gtcgacgacg gcggtctccg tcgtcaggat catctaatga     60
taggagctaa gcgtcaccag cggctcgttc atctaagtga tttgaagttc ctatactttc    120 tagagaaatag gaacttcgga ataggaactt caatgtgctg caatctcaaa tttcatacca   180
gtgcgtctta gataaatata gataacttcg tataggatac tttatacgaa gttatggtac    240
ctataactat ctggtatgat gggactacca aaactttact aggttaccaa tggcacgctt    300
tccctcagcc gaccgaatta gctaggatgt gatagtcctt agtgaacgta tcaagaatgg    360
aaacagctga ttgatacgtc cgaatttatg ttatatttgg caagatttaa tttaattaaa    420
aagaattata tttagctggc aattattagt cttggggcca ctcgtcattt ctaaataact    480
catgtggcat gttgtacctt tgtcagcaat agctcaggca aggccagttc ttaaggaatt    540
aagcctatga ttaaggtgtt tcaagagttt atatcactac cgtttgtatc tacactacga    600
tagtacactc ttttgaatgg gaaccatggt gtgatcaccg ttatctcatc ctctcgatag    660
aagaggaaga ggttaatata actctccatt ggtatgggta atggtacaaa accatcttct    720
```

```
cgcgcattgt aaggtctatg ggcacattat cgaacgcctc cctagtccct agaatgaacc    780
gaccgtaaaa cagagccctt taggatagcc aatcagtagt aatctaacga ctagccgtca    840
ttaatgcttc acgctgccgc aagcactcag ggcgcaaggg ctgctaaagg aagcggaaca    900
cgtagaaagc cagtccgcag aaacggtgct gaccccggat gaatgtcagc tactgggcta    960
tctggacaag ggaaaacgca agcgcaaaga gaaagcaggt agcttgcagt gggcttacat   1020
ggcgatagct agactgggcg gttttatgga cagcaagcga accggaattg ccagctgggg   1080
cgccctctgg taaggttggg aagccctgca agtaaactg gatggctttc ttgccgccaa   1140
ggatctgatg gcgcagggga tcaagatctg atcaagagac aggatgagga tcgtttcgca   1200
tgattgaaca agatggattg cacgcaggtt ctccggccgc ttgggtggag aggctattcg   1260
gctatgactg ggcacaacag acaatcggct gctctgatgc cgccgtgttc cggctgtcag   1320
cgcaggggcg cccggttctt tttgtcaaga ccgacctgtc cggtgccctg aatgaactgc   1380
aggacgaggc agcgcggcta tcgtggctgg ccacgacggg cgttccttgc gcagctgtgc   1440
tcgacgttgt cactgaagcg ggaagggact ggctgctatt gggcgaagtg ccggggcagg   1500
atctcctgtc atctcacctt gctcctgccg agaaagtatc catcatggct gatgcaatgc   1560
ggcggctgca tacgcttgat ccggctacct gcccattcga ccaccaagcg aaacatcgca   1620
tcgagcgagc acgtactcgg atggaagccg gtcttgtcga tcaggatgat ctggacgaag   1680
agcatcaggg gctcgcgcca gccgaactgt tcgccaggct caaggcgcgc atgcccgacg   1740
gcgaggatct cgtcgtgacc catggcgatg cctgcttgcc gaatatcatg gtggaaaatg   1800
gccgcttttc tggattcatc gactgtggcc ggctgggtgt ggcggaccgc tatcaggaca   1860
tagcgttggc tacccgtgat attgctgaag agcttggcgg cgaatgggct gaccgcttcc   1920
tcgtgcttta cggtatcgcc gctcccgatt cgcagcgcat cgccttctat cgccttcttg   1980
acgagttctt ctgagcggga ctctgggtt cgcatcgatg catcgatgcg gcgggtgtgg   2040
tggttacgcg taatctgctg cttgcaaaca aaaaaaccac cgctaccagc ggtggtttgt   2100
ttgccggatc aagagctacc aactcttttt ccgaaggtaa ctggcttcag cagagcgcag   2160
ataccaaata ctgttcttct agtgtagccg tagttaggcc accacttcaa gaactctgta   2220
gcaccgccta catacctcgc tctgctaatc ctgttaccag tggctgctgc cagtggcgat   2280
aagtcgtgtc ttaccgggtt ggactcaaga cgatagttac cggataaggc gcagcggtcg   2340
ggctgaacgg ggggttcgtg cacacagccc agcttggagc gaacgaccta caccgaactg   2400
agatacctac agcgtgagct atgagaaagc gccacgcttc ccgaagggag aaaggcggac   2460
aggtatccgg taagcggcag ggtcggaaca ggagagcgca cgagggagct tccaggggga   2520
aacgcctggt atctttatag tcctgtcggg tttcgccacc tctgacttga gcgtcgattt   2580
ttgtgatgct cgtcaggggg gcggagccta tggaaaaacg ccagcaacgc atcgataaaa   2640
taaaagattt tatttagtct ccagaaaaag ggggaatga aagacccccac ctgtaggttt   2700
ggcaagctag gtggcggccg cattaatgtt gcaactatat agagtcttga tgaccaacgt   2760
aaacctaggc cttctacag ggattgtata aagcctagca atgagaagat cacctctggt   2820
agtaaatatc tttgaggtta tattgtcgat atcttcatct tcgatgcgcc gtagtttaga   2880
agtcataagt cgataacacg agcgtactgt tagattcctt atacgtttca aagagagcgt   2940
tagtacacag aggcgcaggt caatgctagg aagctacggg cgacgctgac cgtctctaac   3000
tgtcaacaaa gttataatga agcaatcatg aattttatct aagtagagat tatgttcata   3060
```

```
gtcaccttca gaagagctat actcagaggc acgccattta taagcctatc tagtagaaga    3120
attgtgggat tgtacctaca ccgagctcct cctgcttaac ccattctgta tttttgatta    3180
aataactacg tattacatag tcactttgcg caaggaaaaa tagtgctttt ccgtctatgt    3240
aaagactaat catatcatta gcgaacgcct tcctcgttta ggcgtctact gatagctatc    3300
gtactggtct gcagcacgtg atgatcctga cgacggagac cgccgtcgtc gacaagccct    3360
aatgatagga gctaagcgtc accagcggct cgttcatcta agtgatttga agttcctata    3420 cttttttgaag aataggaact tcggaatagg aacttcaatg tgctgcaatc tcaaatttca   3480
taccagtgcg tcttagataa atatagataa cttcgtataa tgtatgctat acgaagttat    3540
cacgtggtcc tgctattgtc ttcccaatcc tccccttgc tgtcctgccc caccccaccc     3600
cccagaatag aatgacacct actcagacaa tgcgatgcaa tttcctcatt ttattaggaa    3660
aggacagtgg gagtggcacc ttccagggtc aaggaaggca cggggagggg gcaaacaaca    3720
gatggctggc aactagaagg cacagtcgag gctaatcagc gtcagttagc ctcccccatc    3780
tcccgatccg gacgagtgct ggggcgtcgg tttccactat cggcgagtac ttctacacag    3840
ccatcggtcc agacggccgc gcttctgcgg gcgatttgtg tacgcccgac agtcccggct    3900
ccggatcgga cgattgcgtc gcatcgaccc tgcgcccaag ctgcatcatc gaaattgccg    3960
tcaaccaagc tctgatagag ttggtcaaga ccaatgcgga gcatatacgc ccggagccgc    4020
ggcgatcctg caagctccgg atgcctccgc tcgaagtagc gcgtctgctg ctccatacaa    4080
gccaaccacg gcctccagaa gaagatgttg gcgacctcgt attgggaatc cccgaacatc    4140
gcctcgctcc agtcaatgac cgctgttatg cggccattgt ccgtcaggac attgttggag    4200
ccgaaatccg cgtgcacgag gtgccggact tcggggcagt cctcggccca agcatcagc     4260 tcatcgagag cctgcgcgac ggacgcactg acggtgtcgt ccatcacagt ttgccagtga    4320
tacacatggg gatcagcaat cgcgcatatg aaatcacgcc atgtagtgta ttgaccgatt    4380
ccttgcggtc cgaatgggcc gaacccgctc gtctggctaa gatcggccgc agcgatcgca    4440
tccatggcct ccgcgaccgg ctgcagaaca gcggcagtt cggtttcagg caggtcttgc     4500
aacgtgacac cctgtgcacg gcgggagatg caataggtca ggctctcgct gaattcccca    4560
atgtcaagca cttccggaat cgggagcgcg gccgatgcaa agtgccgata aacataacga    4620
tctttgtaga aaccatcggc gcagctattt acccgcagga catatccacg ccctcctaca    4680
tcgaagctga aagcacgaga ttcttcgccc tccgagagct gcatcaggtc ggagacgctg    4740
tcgaactttt cgatcagaaa cttctcgaca gacgtcgcgg tgagttcagg cttttttgggc   4800 ccagggttgg actccacgtc tcccgccaac ttgagaaggt caaaattcaa agtctgtttc    4860
accggtgctg tctgctcgaa gcggccgcc gccccgactc tagagtaacc cgggtgcgcg     4920
gcgtcggtgg tgccggcggg gggcgccagg tcgcaggcgg tgtagggctc caggcaggcg    4980
gcgaaggcca tgacgtgcgc tatgaaggtc tgctcctgca cgccgtgaac caggtgcgcc    5040
tgcgggccgc gcgcgaacac cgccacgtcc tcgcctgcgt gggtctcttc gtccaggggc    5100
actgctgact gctgccgata tcgggctc ccgctctcgc tctcggtaac atccggccgg      5160
gcgccgtcct tgagcacata gcctggaccg ttttccgtata ggaggaccgt gtaggccttc   5220
ctgtcccggg ccttgccagg ggccagcccg aagatggagc tccctcgcag ggggtagcct    5280
ccgaaggaga agacgtggga gtggtcggca gtgacgaggc tcagcgtgtc ctcctcgctg    5340
gtgagctggc ccgccctctc aatggcgtcg tcgaacatga tcgtctcagt cagtgcccgg    5400
taagccctgc tttcatgatg accatggtcg atgcgaccac cctccacgaa gaggaagaag    5460
```

```
ccgcggggt tcctgctcag caggcgcagg gcagcctctg tcatctccat cagggagggg    5520
tccagtgtgg agtctcggtg gatctcgtat ttcatgtctc caggctcaaa gagacccatg    5580
agatgggtca cagacgggtc cagggaagcc tgcatgagct cagtgcggtt ccacacatac    5640
cgggcaccct ggcgcttcgc cagccattcc tgcaccagat tcttcccgtc cagcctggtc    5700
ccaccttggc tgtagtcatc tgggtactca gggtctgggg ttcccatgcg aaacatgtac    5760
tttcggcctc cacctaggat cacgtcaatg tccatgttgg agatgagctg cgtagcgatg    5820
tcctggcacc cctcctggcg ggccgaggca ggcacgtcgg cgtccgagta ccagttgcgg    5880
ttcaccgtgt gggcgtaggt gccggctggc gaggcgtgct gcactcgtgt ggtggttacc    5940
actcccactg acttccctgc tttcttggcc cgattcatca cggagatgac ctcgttgccg    6000
cgtgtcgtgt tgcactggtt aaagcgggcg gctgcactca agccaatggt ctggaagttg    6060
cccttgaccc cgcacaggta ggccgtggct gtggctccac tgtctggcac atgtttgtct    6120
acattgtatg tcttggacag agccacatat gggaagcggt ccatggccag gggtatctca    6180
ggccccagtt tgtccttctt ctgcccttt aggatcctgg cagctgtcac cgtagacacc    6240
cccatcccat cgcccaggaa gatgatgagg ttcttggcgg ctgtctgtgc aggctgcagc    6300
ttcttggcgg cacccagggc ctcggctgcc tcgcggttcc agaagtccgg gttctcctcc    6360
tcaactggga tgatgcccag ggagagctgt agcctcaggc ccagcagcag cagcagcagc    6420
agcatggtgg atgcggccgc tctagacacg acacctgaaa tggaaggaaa aaactttgaa    6480
ccactgtctg aggcttgaga atgaaccaag atccaaactc aaaaagggca aattccaagg    6540
agaattacat caagtgccaa gctggcctaa cttcagtctc cacccactca gtgtggggaa    6600
actccatcgc ataaaacccc tccccccaac ctaaagacga cgtactccaa aagctcgaga    6660
actaatcgag gtgcctggac ggcgcccggt actccgtgga gtcacatgaa gcgacggctg    6720
aggacggaaa ggcccttttc ctttgtgtgg gtgactcacc cgcccgctct cccgagcgcc    6780
gcgtcctcca ttttgagctc cctgcagcag ggccgggaag cggccatctt tccgctcacg    6840
caactggtgc cgaccgggcc agccttgccg cccagggcgg ggcgatacac ggcggcgcga    6900
ggccaggcac cagagcaggc cggccagctt gagactaccc ccgtccgatt ctcggtggcc    6960
gcgctcgcag gccccgcctc gccgaacatg tgcgctggga cgcacgggcc ccgtcgccgc    7020
ccgcggcccc aaaaaccgaa ataccagtgt gcagatcttg gcccgcattt acaagactat    7080
cttgccagaa aaaagcgtc gcagcaggtc atcaaaaatt ttaaatggct agagacttat    7140
cgaaagcagc gagacaggcg cgaaggtgcc accagattcg cacgcggcgg ccccagcgcc    7200
caagccaggc ctcaactcaa gcacgaggcg aaggggctcc ttaagcgcaa ggcctcgaac    7260
tctcccaccc acttccaacc cgaagctcgg gatcaagaat cacgtactgc agccaggggc    7320
gtggaagtaa ttcaaggcac gcaagggcca taacccgtaa agaggccagg cccgcgggaa    7380
ccacacacgc cacttacctg tgttctggcg tctagagtcg actagctttt aagcgggtcg    7440
ctgcagggtc gctcggtgtt cgaggccaca cgcgtcacct aatatgcga agtggacctg    7500 ggaccgcgcc gccccgactg catctgcgtg ttcgaattcg ccaatgacaa dacgctgggc    7560
ggggtttgtg tcatcataga actaaagaca tgcaaatata tttcttccgg ggacaccgcc    7620
agcaaacgcg agcaacgggc cacggggatg aagcagctgc gccactccct gaagctcctg    7680
cagtccctcg cgcctccggg tgacaagata tgtgtacctgt gccccgtcct ggtgtttgtc    7740
gcccaacgga cgctccgcgt cagccgcgtg accggctcg tcccgcagaa ggtctccggt    7800
```

-continued

```
aatatcaccg cagtcgtgcg gatgctccag agcctgtcca cgtatacggt ccccatggag    7860
cctaggaccc agcgagcccg tcgccgccgc ggcggcgccg cccggggggtc tgcgagcaga    7920 ccgaaaaggt cacactctgg ggcgcgcgac ccgcccgagt cagcggcccg ccagttacca    7980
cccgccgacc aaaccccgc ctccacgag ggcgggggg tgcttaagag gatcgcggcg       8040
ctcttctgcg tgcccgtggc caccaagacc aaaccccgag ccgcctccga atgagagtgt    8100
ttcgttcctt cccctcccc ccgcgtcaga caaaccctaa ccaccgctta agcggccccc     8160
gcgaggtccg aagactcatt tagatctaag ctattctcag ctgccatgga aaatcgatac    8220
cgtcttcgct agaactaggg tcgatcgact ctagtatggt gcactctcag tacaatctgc    8280
tctgatgccg catagttaag ccagtatctg ctccctgctt gtgtgttgga ggtcgctgag    8340
tagtgcgcga gcaaaattta agctacaaca aggcaaggct tgaccgacaa ttgcatgaag    8400
aatctgctta gggttaggcg ttttgcgctg cttcgcgatg tacgggccag atatacgcgt    8460
atctgagggg actagggtgt gtttaggcga aaagcggggc ttcggttgta cgcggttagg    8520
agtcccctca ggatatagta gtttcgcttt tgcataggga gggggaaatg tagtcttatg    8580
caatactctt gtagtcttgc aacatggtaa cgatgagtta gcaacatgcc ttacaaggag    8640
agaaaaagca ccgtgcatgc cgattggtgg aagtaaggtg gtacgatcgt gccttattag    8700
gaaggcaaca gacgggtctg acatggattg gacgaaccac tgaattccgc attgcagaga    8760
tattgtattt aagtgcctag ctcgatacaa taaacgccat ttgaccattc accacattgg    8820
tgtgcacctc caagctggta gaggatcggt cgatcgactc tagacaggta agtggcgttt    8880
ctcggggagc cagctgcgtc cgctgtcgtg ctgtcggtgt agtactagca agcgttaagt    8940
ccccatctgg ctgcggccta ccgaagagtg gtcttcacgt cacacgctgt cccacgcacg    9000
tggttggttt ggtcgcttct ggttactgac tactaagcag cctttctctt tttccttca    9060 ggttctagag cggccgccac cgaaacgccg tacgccacca tggagtggtc ttgggtgttc    9120 ctgttcttc tgtccgtgac cacaggcgtc cacagccagt cggtgtagga gtccggggga    9180
ggcctggtca agcctgaggg atccctgaca ctcacctgca cagcctctgg attctccttc    9240
agttccaact actggatatg ctgggtccgc caggctccgg ggaagggggct ggagtggatc    9300 gcatgcattt atgctggtag tgatagtacc actgactacg cgagctgggc gaaaggccga    9360
ttcaccatct ccaaaacctc gtcgaccacg gtgactctgc aaatgaccag tctgacagcc    9420
gcggacacgg ccacctattt ctgtgcgaga ggtactgatc gtagtgctga ctactttaac    9480
ttgtggggcc caggcaccct ggtcaccatc tcttcagctg gaggaggcgg tagtggtggt    9540
ggtggatctg gtggtggtgg atccgccgat ctgacccaga ctccagcctc gatgtctgca    9600
gctgtgggag gcacagtcac catcaactgc caggccagtc agagtgttag tagtaacaac    9660
cgcttagcct ggtatcagca gaaaccaggg cagcctccca agctccttat ctacagggca    9720
tccactctgg catctggggt cccatcgcgg ttcaaaggca gtggatctgg gacacagttc    9780
actctcacca tcagcgacct ggagtgtgcc gatgctgcca cttactactg tcagagctat    9840
tattggggta gtagtaatag ttataattcc tgggctttcg gcggagggac cgaggtggtc    9900
gtcaaaggtg ctgacaagac ccacacctgt ccccttgcc ctgctcctga gctgctggga    9960
ggccctagcg tgttcctgtt tccccctaag cccaaggaca cctgatgat ctccaggacc    10020 cccgaagtga cctgcgtggt ggtggatgtg agccacgagg accctgaggt gaagttcaac    10080
tggtacgtgg acggcgtgga ggtccacaac gccaagacaa aacccaggga ggagcagtac    10140
aacagcacat atcgggtggt gagcgtgctg accgtgctgc accaggactg gctgaacggc    10200
```

```
aaggagtaca agtgcaaggt gtccaacaag gccctcccccg ccccccattga agaagaccatc    10260 tccaaggcca agggccagcc tagggagccc caggtgtaca cactgcctcc cagcagggac      10320
gagctgacca agaaccaggt gagcctgacc tgcctggtga agggcttcta ccctccgat      10380 atcgccgtgg agtgggagtc caatggccag cccgaaaaca actacaagac cacccccct      10440 gtgctggact ccgatggcag cttcttcctc tactccaagc tgaccgtgga caagtcccgg     10500
tggcagcagg gcaacgtgtt cagctgttcc gtgatgcacg aggccctgca caaccattac    10560
acccagaagt ccctgagcct gtccccccgga aaatgatggg gcgcgccgct tcgaagcgac   10620
ttttgtcccg aattcctgca gcccctagct agtctttccg atcgatggaa ggatccgtcg   10680
gagctctacc ttgcggccgc gacatgataa gatacattga tgagtttgga caaccacaa    10740 ctagaatgca gtgaaaaaaa tgctttattt gtgaaatttg tgatgctatt gctttatttg    10800
tgaaatttgt gatgctattg ctttatttgt aaccattata agctgcaata aacaagttaa    10860
caacaacaat tgcattcatt ttatgtttca ggttcagggg gaggtgtggg aggttttta     10920 aagcaagtaa aacctctaca aatgtggtag atcatttgac ccg                       10963
```

<210> SEQ ID NO 4
<211> LENGTH: 6679
<212> TYPE: DNA
<213> ORGANISM: artificial sequence
<220> FEATURE:
<223> OTHER INFORMATION: chemically synthesized

<400> SEQUENCE: 4

```
agcttgcatg cctgcaggtc gccagtcctg ttttgacaag ttgcctctgg aagcctctac      60
aatgcctctc ttcttttttct ccagagtaag cggaggccag ggccccccgg cctctgctta   120
atactaaaaa aaacagctgt tgtcatagta atgattgggt ggaaacattc taggcagatc     180
tagtcgggag gaaaattact gtgttggagg ccctccgcca tcttctgaag ctgatccccg     240
ggggatccac tagtcgggta tcatatgctg actgtatacg catgaggata gcatatgcta    300
cccggataca gattaggata gcatatacta cccagatata gattaggata gcatatgcta    360
cccagatata gattaggata gcctatgcta cccagatata aattaggata gcatatacta    420
cccagatata gattaggata gcatatgcta cccagatata gattaggata gcctatgcta    480
cccagatata gattaggata gcatatgcta cccagatata gattaggata gcatatgcta    540
tccagatatt tgggtagtat atgctaccca gatataaatt aggatagcat atactacct    600 aatctctatt aggatagcat atgctacccg gatacagatt aggatagcat atactaccca   660
gatatagatt aggatagcat atgctaccca gatatagatt aggatagcct atgctaccca   720
gatataaatt aggatagcat atactaccca gatatagatt aggatagcat atgctaccca   780
gatatagatt aggatagcct atgctaccca gatatagatt aggatagcat atgctatcca   840
gatatttggg tagtatatgc tacccatggc aacattagac tagttctagc gaagacggta    900
tcgattttcc atggcagctg agaatagctt agatctaaat gagtcttcgg acctcgcggg    960
ggccgcttaa gcggtggtta gggtttgtct gacgcgggggg gaggggggaag gaacgaaaca  1020 ctctcattcg gaggcggctc gggggtttggt cttggtggcc acgggcacgc agaagagcgc   1080
cgcgatcctc ttaagcaccc ccccgccctc cgtggaggcg ggggtttggt cggcgggtgg    1140
taactggcgg gccgctgact cgggcgggtc gcgcgcccca gagtgtgacc ttttcggtct   1200
gctcgcagac ccccgggcgg cgccgccgcg gcggcgacgg gctcgctggg tcctaggctc    1260
```

-continued

```
catgggacc gtatacgtgg acaggctctg gagcatccgc acgactgcgg tgatattacc    1320
ggagaccttc tgcgggacga gccgggtcac gcggctgacg cggagcgtcc gttgggcgac    1380
aaacaccagg acggggcaca ggtacactat cttgtcaccc ggaggcgcga gggactgcag    1440
gagcttcagg gagtggcgca gctgcttcat ccccgtggcc cgttgctcgc gtttgctggc    1500
ggtgtccccg gaagaaatat atttgcatgt ctttagttct atgatgacac aaaccccgcc    1560
cagcgtcttg tcattggcga attcgaacac gcagatgcag tcggggcggc gcggtcccag    1620
gtccacttcg catattaagg tgacgcgtgt ggcctcgaac accgagcgac cctgcagcga    1680
cccgcttaaa agctagcgta tacgatcga tcctgcaggt cgactctaga cgccagaaca    1740
caggtaagtg ccgtgtgtgg ttcccgcggg cctggcctct ttacgggtta tggcccttgc    1800
gtgccttgaa ttacttccac gcccctggct gcagtacgtg attcttgatc ccgagcttcg    1860
ggttggaagt gggtgggaga gttcgaggcc ttgcgcttaa ggagccccctt cgcctcgtgc    1920
ttgagttgag gcctggcttg ggcgctgggg ccgccgcgtg cgaatctggt ggcaccttcg    1980
cgcctgtctc gctgctttcg ataagtctct agccattaa aattttttgat gacctgctgc    2040
gacgcttttt ttctggcaag atagtcttgt aaatgcgggc caagatctgc acactggtat    2100
ttcggttttt ggggccgcgg gcggcgacgg ggcccgtgcg tcccagcgca catgttcggc    2160
gaggcggggc ctgcgagcgc ggccaccgag aatcggacgg gggtagtctc aagctggccg    2220
gcctgctctg tgcctggcc tcgcgccgcc gtgtatcgcc ccgccctggg cggcaaggct    2280
ggcccggtcg gcaccagttg cgtgagcgga agatggccg cttcccggcc ctgctgcagg    2340
gagctcaaaa tggaggacgc ggcgctcggg agagcgggcg ggtgagtcac ccacacaaag    2400
gaaaagggcc tttccgtcct cagccgtcgc ttcatgtgac tccacggagt accgggcgcc    2460
gtccaggcac ctcgattagt tctcgagctt ttggagtacg tcgtctttag gttgggggga    2520
ggggttttat gcgatggagt tccccacac tgagtgggtg gagactgaag ttaggccagc    2580
ttggcacttg atgtaattct ccttggaatt tgccctttttt gagtttggat cttggttcat    2640
tctcaagcct cagacagtgg ttcaaagttt tttccttcca tttcaggtgt cgtgtctaga    2700
gcggccgcca ccgaaacgcc gtacggcgcg atcgcccgct agcgcattta aatcctgtac    2760
agccggtccg ggggcgcgcc gcttcgaagc gacttctaga ggatctaaga ggatggagac    2820
agcatgcgaa cgtttacatg tagcgcaaga aacacaaatg cagttgattg agaaaagtag    2880
tgataagttg caagatcata tactgtactg gactgctgtt agaactgaga acacactgct    2940
ttatgctgca aggaaaaaag gggtgactgt cctaggacac tgcagagtac cacactctgt    3000
agtttgtcaa gagagagcca agcaggccat tgaaatgcag ttgtctttgc aggagttaag    3060
caaaactgag tttgggatg aaccatggtc tttgcttgac acaagctggg accgatatat    3120
gtcagaacct aaacggtgct ttaagaaagg cgccagggtg gtagaggtgg agtttgatgg    3180
aaatgcaagc aatacaaact ggtacactgt ctacagcaat ttgtacatgc gcacagagga    3240
cggctggcag cttgcgaagg ctggggctga cggaactggg ctctactact gcaccatcgc    3300
cggtgctgga cgcatttact attctcgctt tggtgacgag gcagccagat ttagtacaac    3360
agggcattac tctgtaagag atcaggacag agtgtatgct ggtgtctcat ccacctcttc    3420
tgatttttaga gatcgcccag acggagtctg ggtcgcatcc gaaggacctg aaggagaccc    3480
tgcaggaaaa gaagccgagc cagcccagcc tgtctcttct ttgctcggct ccccgcctg    3540
cggtcccatc agagcaggcc tcggttgggt acggacggt cctcgctcgc accectacaa    3600
tttttcctgca ggctcggggg gctctattct ccgctcttcc tccacccegg tgcagggcac    3660
```

```
ggtaccggtg gacttggcat caaggcagga agaagaggag cagtcgcccg actccacaga    3720
ggaagaacca gtgactctcc caaggcgcac caccaatgat ggattccacc tgttaaaggc    3780
aggagggtca tgctttgctc taatttcagg aactgctaac caggtaaagt gctatcgctt    3840
tcgggtgaaa aagaaccata gacatcgcta cgagaactgc accaccacct ggttcacagt    3900
tgctgacaac ggtgctgaaa gacaaggaca agcacaaata ctgatcacct ttggatcgcc    3960
aagtcaaagg caagactttc tgaaacatgt accactacct cctggaatga acatttccgg    4020
ctttacagcc agcttggact tctgatcact gccattgcct tttcttcatc tgactggtgt    4080
actatgccaa atctatggtt tctattgttc ttgggactag ttgtcccgaa ttcctgcagc    4140
ccctagctag tctttccgat cgatggaagg atccgtcgga gctctacctt gcggccgcga    4200
catgataaga tacattgatg agtttggaca aaccacaact agaatgcagt gaaaaaaatg    4260
ctttatttgt gaaatttgtg atgctattgc tttatttgtg aaatttgtga tgctattgct    4320
ttatttgtaa ccattataag ctgcaataaa caagttaaca acaacaattg cattcatttt    4380
atgtttcagg ttcaggggga ggtgtgggag gttttttaaa gcaagtaaaa cctctacaaa    4440
tgtggtagat catttaaatg ttaattgtac tagcttgcca aacctacagg tggggtcttt    4500
cattcccccc ttttctggaa gactaaataa aatcttttat tttatcgatg cgttgctggc    4560
gttttttccat aggctccgcc cccctgacga gcatcacaaa aatcgacgct caagtcagag    4620
gtggcgaaac ccgacaggac tataaagata ccaggcgttt ccccctggaa gctccctcgt    4680
gcgctctcct gttccgaccc tgccgcttac cggatacctg tccgcctttc tcccttcggg    4740
aagcgtggcg ctttctcata gctcacgctg taggtatctc agttcggtgt aggtcgttcg    4800
ctccaagctg ggctgtgtgc acgaaccccc cgttcagccc gaccgctgcg ccttatccgg    4860
taactatcgt cttgagtcca acccggtaag acacgactta tcgccactgg cagcagccac    4920
tggtaacagg attagcagag cgaggtatgt aggcggtgct acagagttct tgaagtggtg    4980
gcctaactac ggctacacta agaacagt atttggtatc tgcgctctgc tgaagccagt    5040
taccttcgga aaaagagttg gtagctcttg atccggcaaa caaaccaccg ctggtagcgg    5100
tggttttttt gtttgcaagc agcagattac gcgtaaccac cacacccgcc gcatcgatgc    5160
atcgatgcga cccccagagt cccgctcaga agaactcgtc aagaaggcga tagaaggcga    5220
tgcgctgcga atcgggagcg gcgataccgt aaagcacgag gaagcggtca gcccattcgc    5280
cgccaagctc ttcagcaata tcacgggtag ccaacgctat gtcctgatag cggtccgcca    5340
cacccagccg gccacagtcg atgaatccag aaaagcggcc attttccacc atgatattcg    5400
gcaagcaggc atcgccatgg gtcacgacga gatcctcgcc gtcgggcatg cgcgccttga    5460
gcctggcgaa cagttcggct ggcgcgagcc ctgatgctc ttcgtccaga tcatcctgat    5520
cgacaagacc ggcttccatc cgagtacgtg ctcgctcgat gcgatgtttc gcttggtggt    5580
cgaatgggca ggtagccgga tcaagcgtat gcagccgccg cattgcatca gccatgatgg    5640
atactttctc ggcaggagca aggtgagatg acaggagatc ctgccccggc acttcgccca    5700
atagcagcca gtcccttccc gcttcagtga acgtcgag cacagctgcg caaggaacgc    5760
ccgtcgtggc cagccacgat agccgcgctg cctcgtcctg cagttcattc agggcaccgg    5820
acaggtcggt cttgacaaaa agaaccgggc gcccctgcgc tgacagccgg aacacggcgg    5880
catcagagca gccgattgtc tgttgtgccc agtcatagcc gaatagcctc tccacccaag    5940
cggccggaga acctgcgtgc aatccatctt gttcaatcat gcgaaacgat cctcatcctg    6000
```

```
tctcttgatc agatcttgat cccctgcgcc atcagatcct tggcggcaag aaagccatcc    6060
agtttacttt gcagggcttc ccaaccttac cagagggcgc cccagctggc aattccggtt    6120
cgcttgctgt ccataaaacc gcccagtcta gctatcgcca tgtaagccca ctgcaagcta    6180
cctgctttct ctttgcgctt gcgttttccc ttgtccagat agcccagtag ctgacattca    6240
tccggggtca gcaccgtttc tgcggactgg cttctacgt gttccgcttc ctttagcagc     6300
ccttgcgccc tgagtgcttg cggcagcgtg aagcttttg caaaagccta ggcctccaaa     6360
aaagcctcct cactacttct ggaatagctc agaggccgag gcggcctcgg cctctgcata    6420
aataaaaaaa attagtcagc catggggcgg agaatgggcg gaactgggcg gagttagggg    6480
cgggatgggc ggagttaggg gcgggactat ggttgctgac taattgagat gcatgctttg    6540
catacttctg cctgctgggg agcctgggga ctttccacac ctggttgctg actaattgag    6600
atgcatgctt tgcatacttc tgcctgctgg ggagcctggg gactttccac accctaactg    6660
acacacattc cacagggtc                                                 6679

<210> SEQ ID NO 5
<211> LENGTH: 34
<212> TYPE: DNA
<213> ORGANISM: artificial sequence
<220> FEATURE:
<223> OTHER INFORMATION: chemically synthesized

<400> SEQUENCE: 5
ataacttcgt ataatgtatg ctatacgaag ttat                                34

<210> SEQ ID NO 6
<211> LENGTH: 34
<212> TYPE: DNA
<213> ORGANISM: artificial sequence
<220> FEATURE:
<223> OTHER INFORMATION: chemically synthesized

<400> SEQUENCE: 6
ataacttcgt ataaagtatc ctatacgaag ttat                                34

<210> SEQ ID NO 7
<211> LENGTH: 48
<212> TYPE: DNA
<213> ORGANISM: artificial sequence
<220> FEATURE:
<223> OTHER INFORMATION: chemically synthesized

<400> SEQUENCE: 7
gaagttccta ttccgaagtt cctattctct agaaagtata ggaacttc                 48

<210> SEQ ID NO 8
<211> LENGTH: 48
<212> TYPE: DNA
<213> ORGANISM: Artificial sequence
<220> FEATURE:
<223> OTHER INFORMATION: chemically synthesized

<400> SEQUENCE: 8
gaagttccta ttccgaagtt cctattcttc aaaaagtata ggaacttc                 48

<210> SEQ ID NO 9
<211> LENGTH: 48
<212> TYPE: DNA
<213> ORGANISM: artificial sequence
<220> FEATURE:
<223> OTHER INFORMATION: chemically synthesized
```

<400> SEQUENCE: 9

```
ggtttgtctg gtcaaccacc gcggtctcag tggtgtacgg tacaaacc        48
```

<210> SEQ ID NO 10
<211> LENGTH: 38
<212> TYPE: DNA
<213> ORGANISM: artificial sequence
<220> FEATURE:
<223> OTHER INFORMATION: chemically synthesized

<400> SEQUENCE: 10

```
ggcttgtcga cgacggcggt ctccgtcgtc aggatcat        38
```

<210> SEQ ID NO 11
<211> LENGTH: 1497
<212> TYPE: DNA
<213> ORGANISM: artificial sequence
<220> FEATURE:
<223> OTHER INFORMATION: chemically synthesized

<400> SEQUENCE: 11

```
atggagtggt cttgggtgtt cctgttcttt ctgtccgtga ccacaggcgt ccacagccag        60
tcggtggagg agtccggggg aggcctggtc aagcctgagg atccctgac actcacctgc        120
acagcctctg gattctcctt cagttccaac tactggatat gctgggtccg ccaggctccg        180
gggaaggggc tggagtggat cgcatgcatt tatgctggta gtgatagtac cactgactac        240
gcgagctggg cgaaaggccg attcaccatc tccaaaacct cgtcgaccac ggtgactctg        300
caaatgacca gtctgacagc cgcggacacg gccacctatt tctgtgcgag aggtactgat        360
cgtagtgctg actactttaa cttgtggggc caggcaccc tggtcaccat ctcttcagct        420
ggaggaggcg gtagtggtgg tggtggatct ggtggtggtg gatccgccga tctgacccag        480
actccagcct cgatgtctgc agctgtggga ggcacagtca ccatcaactg ccaggccagt        540
cagagtgtta gtagtaacaa ccgcttagcc tggtatcagc agaaaccagg gcagcctccc        600
aagctcctta tctacagggc atccactctg catctgggg tcccatcgcg gttcaaaggc        660
agtggatctg gacacagtt cactctcacc atcagcgacc tggagtgtgc cgatgctgcc        720
acttactact gtcagagcta ttattggggt agtagtaata gttataattc ctgggctttc        780
ggcggaggga ccgaggtggt cgtcaaaggt gctgacaaga cccacacctg tcccccttgc        840
cctgctcctg agctgctggg aggcctagc gtgttcctgt ttcccctaa gcccaaggac        900
accctgatga tctccaggac ccccgaagtg acctgcgtgg tggtggatgt gagccacgag        960
gaccctgagg tgaagttcaa ctggtacgtg gacggcgtgg aggtccacaa cgccaagaca       1020
aaacccaggg aggagcagta caacagcaca tatcgggtgg tgagcgtgct gaccgtgctg       1080
caccaggact ggctgaacgg caaggagtac aagtgcaagg tgtccaacaa ggccctcccc       1140
gcccccattg agaagaccat ctccaaggcc aagggccagc ctaggagcc ccaggtgtac       1200
acactgcctc ccagcaggga cgagctgacc aagaaccagg tgagcctgac ctgcctggtg       1260
aagggcttct accctccga tatcgccgtg gagtgggagt ccaatggcca gcccgaaaac       1320
aactacaaga ccacccccc tgtgctggac tccgatggca gcttcttcct ctactccaag       1380
ctgaccgtgg acaagtcccg gtggcagcag ggcaacgtgt tcagctgttc cgtgatgcac       1440
gaggccctgc acaaccatta cacccagaag tccctgagcc tgtcccccgg aaaatga       1497
```

<210> SEQ ID NO 12

<211> LENGTH: 3075
<212> TYPE: DNA
<213> ORGANISM: artificial sequence
<220> FEATURE:
<223> OTHER INFORMATION: chemically synthesized

<400> SEQUENCE: 12

| | | | | | |
|---|---|---|---|---|---|
| atgggcgtga | aggtgctgtt | cgccctgatc | tgtatcgccg | tggccgaggc | caagcccacc | 60 |
| gagaacaatg | aggacttcaa | catcgtggcc | gtggccagca | acttcgccac | cacagacctg | 120 |
| gatgccgaca | gaggcaagct | gcccggcaag | aaactgcccc | tggaagtgct | gaaagagatg | 180 |
| gaagccaatg | ccagaaaggc | cggctgcacc | agaggctgcc | tgatctgcct | gagccacatc | 240 |
| aagtgcaccc | ccaagatgaa | gaagttcatc | cccggcagat | gccacaccta | tgagggcgac | 300 |
| aaagagtctg | cccagggcgg | catcggcgag | gccatcgtgg | acatccccga | gatccccggc | 360 |
| ttcaaggacc | tggaacccat | ggaacagttt | atcgcccagg | tggacctgtg | cgtggactgc | 420 |
| accaccggct | gtctgaaggg | cctggccaac | gtgcagtgca | gcgacctgct | gaagaagtgg | 480 |
| ctgccccaga | gatgcgccac | cttcgccagc | aagatccagg | gccaggtgga | caagatcaag | 540 |
| ggggctggcg | gcgacgcacc | ggtgaaacag | actttgaatt | ttgaccttct | caagttggcg | 600 |
| ggagacgtgg | agtccaaccc | tgggcccttc | gaaatggtga | gcaagggcga | ggagctgttc | 660 |
| accggggtgg | tgcccatcct | ggtcgagctg | gacggcgacg | taaacggcca | caagttcagc | 720 |
| gtgtccggcg | agggcgaggg | cgatgccacc | tacggcaagc | tgaccctgaa | gttcatctgc | 780 |
| accaccggca | agctgcccgt | gccctggccc | accctcgtga | ccaccctgac | ctacggcgtg | 840 |
| cagtgcttca | gccgctaccc | cgaccacatg | aagcagcacg | acttcttcaa | gtccgccatg | 900 |
| cccgaaggct | acgtccagga | gcgcaccatc | ttcttcaagg | acgacggcaa | ctacaagacc | 960 |
| cgcgccgagg | tgaagttcga | gggcgacacc | ctggtgaacc | gcatcgagct | gaagggcatc | 1020 |
| gacttcaagg | aggacggcaa | catcctgggg | cacaagctgg | agtacaacta | caacagccac | 1080 |
| aacgtctata | tcatggccga | caagcagaag | aacggcatca | aggtgaactt | caagatccgc | 1140 |
| cacaacatcg | aggacggcag | cgtgcagctc | gccgaccact | accagcagaa | cacccccatc | 1200 |
| ggcgacggcc | ccgtgctgct | gcccgacaac | cactacctga | gcacccagtc | cgccctgagc | 1260 |
| aaagacccca | acgagaagcg | cgatcacatg | gtcctgctgg | agttcgtgac | cgccgccggg | 1320 |
| atcactctcg | gcatggacga | gctgtacaag | gcaccggtga | acagactttt | gaattttgac | 1380 |
| cttctcaagt | tggcgggaga | cgtggagtcc | aaccctgggc | ccatggaaga | tgccaaaaac | 1440 |
| attaagaaag | cccagcgcc | attctaccca | ctcgaagacg | ggaccgccgg | cgagcagctg | 1500 |
| cacaaagcca | tgaagcgcta | cgccctggtg | cccggcacca | tcgcctttac | cgacgcacat | 1560 |
| atcgaggtgg | acattaccta | cgccgagtac | ttcgagatga | gcgttcggct | ggcagaagct | 1620 |
| atgaagcgct | atgggctgaa | tacaaaccat | cggatcgtgg | tgtgcagcga | gatagcttg | 1680 |
| cagttcttca | tgcccgtgtt | gggtgccctg | ttcatcggtg | tggctgtggc | cccagctaac | 1740 |
| gacatctaca | cgagcgcga | gctgctgaac | agcatgggca | tcagccagcc | caccgtcgta | 1800 |
| ttcgtgagca | agaaagggct | gcaaaagatc | ctcaacgtgc | aaaagaagct | accgatcata | 1860 |
| caaaagatca | tcatcatgga | tagcaagacc | gactaccagg | gcttccaaag | catgtacacc | 1920 |
| ttcgtgactt | cccatttgcc | accggcttc | aacgagtacg | acttcgtgcc | cgagagcttc | 1980 |
| gaccgggaca | aaaccatcgc | cctgatcatg | aacagtagtg | gcagtaccgg | attgcccaag | 2040 |
| ggcgtagccc | taccgcaccg | caccgcttgt | gtccgattca | gtcatgcccg | cgaccccatc | 2100 |
| ttcggcaacc | agatcatccc | cgacaccgct | atcctcagcg | tggtgccatt | tcaccacggc | 2160 |

```
ttcggcatgt tcaccacgct gggctacttg atctgcggct ttcgggtcgt gctcatgtac      2220
cgcttcgagg aggagctatt cttgcgcagc ttgcaagact ataagattca atctgccctg      2280
ctggtgccca cactatttgg cttcttcgct aagagcactc tcatcgacaa gtacgaccta      2340
agcaacttgc acgagatcgc cagcggcggg gcgccgctca gcaaggaggt aggtgaggcc      2400
gtggccaaac gcttccacct accaggcatc cgccagggct acggcctgac agaaacaacc      2460
agcgccattc tgatcacccc cgaaggggac gacaagcctg cgcagtagg caaggtggtg       2520 cccttcttcg aggctaaggt ggtggacttg gacaccggta agacactggg tgtgaaccag      2580
cgcggcgagc tgtgcgtccg tggccccatg atcatgagcg gctacgttaa caaccccgag      2640
gctacaaacg ctctcatcga aaggacggc tggctgcaca gcggcgacat cgcctactgg        2700
gacgaggacg agcacttctt catcgtggac cggctgaaga gcctgatcaa atacaagggc      2760
taccaggtag ccccagccga actggagagc atcctgctgc aacaccccaa catcttcgac      2820
gccggggtcg ccggcctgcc cgacgacgat gccggcgagc tgcccgccgc agtcgtcgtg      2880
ctggaacacg gtaaaaccat gaccgagaag gagatcgtgg actatgtggc cagccaggtt      2940
acaaccgcca agaagctgcg cggtggtgtt gtgttcgtgg acgaggtgcc taaaggactg      3000
accggcaagt ggacgcccg caagatccgc gagattctca ttaaggccaa gaagggcggc       3060
aagatcgccg tgtga                                                       3075

<210> SEQ ID NO 13
<211> LENGTH: 2664
<212> TYPE: DNA
<213> ORGANISM: artificial sequence
<220> FEATURE:
<223> OTHER INFORMATION: chemically synthesized

<400> SEQUENCE: 13
atgctgctgc tgctgctgct gctgggcctg aggctacagc tctccctggg catcatccca        60
gttgaggagg agaacccgga cttctggaac cgcgaggcag ccgaggccct gggtgccgcc       120
aagaagctgc agcctgcaca gacagccgcc aagaacctca tcatcttcct gggcgatggg       180 atggggtgt ctacggtgac agctgccagg atcctaaaag ggcagaagaa ggacaaactg        240
gggcctgaga tacccctggc catgaccgc ttcccatatg tggctctgtc caagacatac        300
aatgtagaca aacatgtgcc agacagtgga gccacagcca cggcctacct gtgcgggtc        360 aagggcaact tccagaccat tggcttgagt gcagccgccc gctttaacca gtgcaacacg       420
acacgcggca acgaggtcat ctccgtgatg aatcgggcca agaaagcagg gaagtcagtg       480
ggagtggtaa ccaccacacg agtgcagcac gcctcgccag ccggcaccta cgcccacacg       540
gtgaaccgca ctggtactc ggacgccgac gtgcctgcct cggcccgcca ggagggggtgc       600 caggacatcg ctacgcagct catctccaac atggacattg acgtgatcct aggtggaggc       660
cgaaagtaca tgtttcgcat gggaacccca gaccctgagt acccagatga ctacagccaa       720
ggtgggacca ggctggacgg aagaatctg gtgcaggaat ggctggcgaa gcgccagggt        780
gcccggtatg tgtggaaccg cactgagctc atgcaggctt ccctggaccc gtctgtgacc       840
catctcatgg gtctctttga gcctggagac atgaaatacg agatccaccg agactccaca      900
ctggacccct ccctgatgga gatgacagag gctgccctgc gctgctgag caggaacccc       960 cgcggcttct tcctcttcgt ggagggtggt cgcatcgacc atggtcatca tgaaagcagg     1020
gcttaccggg cactgactga gacgatcatg ttcgacgacg ccattgagag ggcgggccag     1080
```

| | |
|---|---|
| ctcaccagcg aggaggacac gctgagcctc gtcactgccg accactccca cgtcttctcc | 1140 |
| ttcggaggct accccctgcg agggagctcc atcttcgggc tggccccctgg caaggcccgg | 1200 |
| gacaggaagg cctacacggt cctcctatac ggaaacggtc caggctatgt gctcaaggac | 1260 |
| ggcgcccggc cggatgttac cgagagcgag agcgggagcc ccgagtatcg gcagcagtca | 1320 |
| gcagtgcccc tggacgaaga gacccacgca ggcgaggacg tggcggtgtt cgcgcgcggc | 1380 |
| ccgcaggcgc acctggttca cggcgtgcag gagcagacct tcatagcgca cgtcatggcc | 1440 |
| ttcgccgcct gcctggagcc ctacaccgcc tgcgacctgg cgcccccgc cggcaccacc | 1500 |
| gacgccgcgc acccgggtta ctctagagtc ggggcggccg gccgcttcga gcagacagca | 1560 |
| ccggtgaaac agactttgaa ttttgacctt ctcaagttgg cgggagacgt ggagtccaac | 1620 |
| cctgggccca aaaagcctga actcaccgcg acgtctgtcg agaagtttct gatcgaaaag | 1680 |
| ttcgacagcg tctccgacct gatgcagctc tcggagggcg aagaatctcg tgctttcagc | 1740 |
| ttcgatgtag agggcgtgg atatgtcctg cgggtaaata gctgcgccga tggtttctac | 1800 |
| aaagatcgtt atgtttatcg gcactttgca tcggccgcgc tcccgattcc ggaagtgctt | 1860 |
| gacattgggg aattcagcga gagcctgacc tattgcatct cccgccgtgc acagggtgtc | 1920 |
| acgttgcaag acctgcctga aaccgaactg cccgctgttc tgcagccggt cgcggaggcc | 1980 |
| atggatgcga tcgctgcggc cgatcttagc cagacgagcg gttcggccc attcggaccg | 2040 |
| caaggaatcg tcaatacac tacatggcgt gatttcatat gcgcgattgc tgatccccat | 2100 |
| gtgtatcact ggcaaactgt gatggacgac accgtcagtg cgtccgtcgc gcaggctctc | 2160 |
| gatgagctga tgctttgggc cgaggactgc cccgaagtcc ggcacctcgt gcacgcggat | 2220 |
| ttcggctcca acaatgtcct gacggacaat ggccgcataa cagcggtcat tgactggagc | 2280 |
| gaggcgatgt cgggggattc caatacgag gtcgccaaca tcttcttctg gaggccgtgg | 2340 |
| ttggcttgta tggagcagca gacgcgctac ttcgagcgga gcatccgga gcttgcagga | 2400 |
| tcgccgcggc tccgggcgta tatgctccgc attggtcttg accaactcta tcagagcttg | 2460 |
| gttgacggca atttcgatga tgcagcttgg gcgcagggtc gatgcgacgc aatcgtccga | 2520 |
| tccggagccg ggactgtcgg gcgtacacaa atcgcccgca gaagcgcggc cgtctggacc | 2580 |
| gatggctgtg tagaagtact cgccgatagt ggaaaccgac gccccagcac tcgtccggat | 2640 |
| cgggagatgg gggaggctaa ctga | 2664 |

<210> SEQ ID NO 14
<211> LENGTH: 7908
<212> TYPE: DNA
<213> ORGANISM: artificial sequence
<220> FEATURE:
<223> OTHER INFORMATION: chemically synthesized

<400> SEQUENCE: 14

| | |
|---|---|
| gacccagcga gcccgtcgcc gccgcggcgg cgccgcccgg gggtctgcga gcagaccgaa | 60 |
| aaggtcacac tctggggcgc gcgacccgcc cgagtcagcg gcccgccagt taccaccccgc | 120 |
| cgaccaaacc cccgcctcca cggagggcgg gggggtgctt aagaggatcg cggcgctctt | 180 |
| ctgcgtgccc gtggccacca agaccaaacc ccgagccgcc tccgaatgag agtgtttcgt | 240 |
| tccttccccc tccccccgcg tcagacaaac cctaaccacc gcttaagcgg cccccgcgag | 300 |
| gtccgaaagac tcatttcgta ctcgtcgaca ccggaagcgg tcgccactct gaccggacac | 360 |
| ggttcagaca tagaccgcag gcggttcgta cccataccgt tgccggtgaa atgagttacc | 420 |
| gatcacggtg gcacgcctaa ccgccaacgg tgtgtctaaa gaccgcgtcc ggtagctgtc | 480 |

```
cttaccgttg acgtgtcca gacagaccgc gaacggttgg ttttccaacc gatagcggta    540
agcttgatat agctccggtg cccgtcagtg ggcagagcgc acatcgccca cagtccccga    600
gaagttgggg ggaggggtcg gcaattgaac cggagcttga tgcgtctaga tgatttcctt    660
catccctggc acacgtccag gcagtgtcga atccatctct gctacagggg aaaacaaata    720
acatttgagt ccagtggaga ccgggagcag aagtaaaggg aagtgataac ccccagagcc    780
cggaagcctc tggaggctga gacctcgccc cccttgcgtg atagggccta cggagccaca    840
tgaccaaggc actgtcgcct ccgcacgtgt gagagtgcag ggccccaaga tggctgccag    900
gcctcgaggc ctgactcttc tatgtcactt ccgtaccggc gagaaaggcg ggccctccag    960
ccaatgaggc tgcggggcgg gccttcacct tgataggcac tcgagttatc caatggtgcc   1020
tgcgggccgg agcgactagg aactaacgtc atgccgagtt gctgagcgcc ggcaggcggg   1080
gccggggcgg ccaaaccaat gcgatggccg gggcggagtc gggcgctcta taagttgtcg   1140
ataggcgggc actccgccct agtttctaag gaaccggtag atcgaattcc tgcagcccgg   1200
gggatccact agttctagac gccagaacac aggtaagtgc cgtgtgtggt tcccgcgggc   1260
ctggcctctt tacgggttat ggcccttgcg tgccttgaat tacttccacg cccctggctg   1320
cagtacgtga ttcttgatcc cgagcttcgg gttggaagtg ggtgggagag ttcgaggcct   1380
tgcgcttaag gagccccttc gcctcgtgct tgagttgagg cctggcttgg gcgctggggc   1440
cgccgcgtgc gaatctggtg gcaccttcgc gcctgtctcg ctgctttcga taagtctcta   1500
gccatttaaa attttttgatg acctgctgcg acgcttttttt tctggcaaga tagtcttgta   1560
aatgcgggcc aagatctgca cactggtatt tcggtttttg gggccgcggg cggcgacggg   1620
gcccgtgcgt cccagcgcac atgttcggcg aggcggggcc tgcgagcgcg gccaccgaga   1680
atcggacggg ggtagtctca agctggccgg cctgctctgg tgcctggcct cgcgccgccg   1740
tgtatcgccc cgccctgggc ggcaaggctg gcccggtcgg caccagttgc gtgagcggaa   1800
agatggccgc ttcccggccc tgctgcaggg agctcaaaat ggaggacgcg gcgctcggga   1860
gagcgggcgg gtgagtcacc cacacaaagg aaaagggcct ttccgtcctc agccgtcgct   1920
tcatgtgact ccacggagta ccgggcgccg tccaggcacc tcgattagtt ctcgagcttt   1980
tggagtacgt cgtctttagg ttggggggag gggttttatg cgatggagtt tccccacact   2040
gagtgggtgg agactgaagt taggccagct tggcacttga tgtaattctc cttgaatttt   2100 gcccttttttg agtttggatc ttggttcatt ctcaagcctc agacagtggt tcaaagtttt   2160
ttccttccat ttcaggtgtc gtgtctagag cggccgccac cgaaacgccg tacgtcgcca   2220
ccatgaggct cgccgtggga gccctgctgg tctgcgccgt cctggggctg tgtctggctg   2280
tccctgataa aactgtgaga tggtgtcag tgtcggagca tgaggccact aagtgccaga   2340
gtttccgcga ccatatgaaa agcgtcattc catccgatgg tcccagtgtt gcttgtgtga   2400
agaaagcctc ctaccttgat tgcatcaggg ccattgcggc aaacgaagcg gatgctgtga   2460
cactggatgc tggtttggtg tatgatgctt acctggctcc aataacctga agcctgtgg   2520 tggcagagtt ctatgggtcc aaggaggacc cccagacctt ctactacgct gttgctgtgg   2580
tgaagaagga tagtggcttc cagatgaacc agcttcgagg caagaagtcc tgccacacgg   2640
gtctaggccg ctccgctggg tggaacatcc ccataggctt actttactgt gacttacctg   2700
agccacgtaa acctcttgag aaaagcagtgg ccaatttcctt ctcgggcagc tgtgcccctt   2760
gtgcggatgg gacggacttc ccccagctgt gtcaactgtg tccagggtgt ggctgctcca   2820
```

```
cccttaacca atacttcggc tactcgggag ccttcaagtg tctgaaggat ggtgctgggg    2880
atgtggcctt tgtcaagcac tcgactatat ttgagaactt ggcaaacaag gctgacaggg    2940
accagtatga gctgctttgc ctggacaaca cccggaagcc ggtagatgaa tacaaggact    3000
gccacttggc ccaggtccct tctcataccg tcgtggcccg aagtatgggc ggcaaggagg    3060
acttgatctg ggagcttctc aaccaggccc aggaacattt tggcaaggac aagtccaagg    3120
agttccagct cttcagctct cctcatggga aggacctgct gtttaaggac tctgcccacg    3180
ggttcttgaa ggtccccccc aggatggatg ccaagatgta cctgggctat gagtatgtca    3240
ctgccatccg gaatctacgg gaaggcacat gcccagaagc cccaacagat gaatgcaagc    3300
ctgtgaagtg gtgtgcgctg agccaccacg agaggctcaa gtgtgatgag tggagtgtta    3360
acagtgtagg gaaaatagag tgtgtatcag cagagaccac cgaagactgc atcgccaaga    3420
tcatgaatgg agaagctgat gccatgagct tggatggagg gtttgtctac atagcgggca    3480
agtgtggtct ggtgcctgtc ctcgccgaga actacaacaa gagcgacaac tgtgaggata    3540
caccagaggc agggtatttt gctgtagcag tggtgaagaa atcagcttct gacctcacct    3600
gggacaatct gaaaggcaag aagtcctgcc atacggcagt tggcagaacc gctggctgga    3660
acatccccat gggcctgctc tacaataaga tcaaccactg ccgcttcgac gagttcttca    3720
gcgagggctg cgcccctggg tctaagaaag actccagtct ctgtaagctg tgtatgggct    3780
caggcctaaa cctgtgtgaa cccaacaaca agagaggata ctacggctac acaggcgctt    3840
tcaggtgtct ggttgagaag ggagatgtgg cctttgtgaa acaccagact gtcccacaga    3900
acactggggg aaagaacccc tgatccatgg gctaagaacct gaacgagaag gactacgagc    3960
tcctgtgcct tgatggtacc aggaaacctg tggaggagta tgcgaactgc cacctggcca    4020
gagcccgcaa tcacgctgtg gtcacacgga agataagga agcttgcgtc cacaagatat    4080
tacgtcaaca gcagcaccta tttggaagca acgtaactga ctgctcgggc aacttttgtt    4140
tgttccggtc ggaaaccaag gaccttctgt tcagagatga cacagtatgt ttggccaaac    4200
ttcatgacag aaacacctac gagaagtact gggcgaggga gtacgtcaag gctgttggta    4260
acctgagaaa atgctccacc tcatcactcc tggaagcctg cactttccgt agaccttaat    4320
gattcgaagc gacttttgtc ccgaattcct gcagccccta gctagtcttt ccgatcgatg    4380
gaaggatccg tcggagctct accttgcggc cgcgacatga taagatacat tgatgagttt    4440
ggacaaacca caactagaat gcagtgaaaa aaatgcttta tttgtgaaat ttgtgatgct    4500
attgctttat ttgtgaaatt tgtgatgcta ttgctttatt tgtaaccatt ataagctgca    4560
ataaacaagt taacaacaac aattgcattc attttatgtt tcaggttcag ggggaggtgt    4620
gggaggtttt ttaaagcaag taaaacctct acaaatgtgg tagatcattt aaatgttaat    4680
tgtgtcgaca ggatcctata acttcgtata gcatacatta tacgaagtta tcagacaccc    4740
agtgtcgaac aacacctgac cgcgttgctg gcgttttttcc ataggctccg cccccctgac    4800
gagcatcaca aaaatcgacg ctcaagtcag aggtggcgaa acccgacagg actataaaga    4860
taccaggcgt ttccccctgg aagctccctc gtgcgctctc ctgttccgac cctgccgctt    4920
accggatacc tgtccgcctt tctcccttcg ggaagcgtgg cgctttctca tagctcacgc    4980
tgtaggtatc tcagttcggt gtaggtcgtt cgctccaagc tgggctgtgt gcacgaaccc    5040
cccgttcagc ccgaccgctg cgccttatcc ggtaactatc gtcttgagtc aacccggta    5100 agacacgact tatcgccact ggcagcagcc actggtaaca ggattagcag agcgaggtat    5160
gtaggcggtg ctacagagtt cttgaagtgg tggcctaact acggctacac tagaaggaca    5220
```

```
gtatttggta tctgcgctct gctgaagcca gttaccttcg gaaaaagagt tggtagctct    5280
tgatccggca aacaaaccac cgctggtagc ggtggttttt ttgtttgcaa gcagcagatt    5340
acgcgcagaa aaaaggatc tcaagaagat cctttgatct tttctacggg gtctgacgct     5400
cagtggaacg aaaactcacg ttaagggatt ttggtcatga gattatcaaa aaggatcttc    5460
acctagatcc ttttaaatta aaaatgaagt tttaaatcaa tctaaagtat atatgagtaa    5520
acttggtctg acagttacca atgcttaatc agtgaggcac ctatctcagc gatctgtcta    5580
tttcgttcat ccatagttgc ctgactcccc gtcgtgtaga taactacgat acgggagggc    5640
ttaccatctg gccccagtgc tgcaatgata ccgcgagacc cacgctcacc ggctccagat    5700
ttatcagcaa taaaccagcc agccggaagg gccgagcgca gaagtggtcc tgcaacttta    5760
tccgcctcca tccagtctat taattgttgc cgggaagcta gagtaagtag ttcgccagtt    5820
aatagtttgc gcaacgttgt tgccattgct acaggcatcg tggtgtcacg ctcgtcgttt    5880
ggtatggctt cattcagctc cggttcccaa cgatcaaggc gagttacatg atccccccatg   5940 ttgtgcaaaa aagcggttag ctccttcggt cctccgatcg ttgtcagaag taagttggcc    6000
gcagtgttat cactcatggt tatggcagca ctgcataatt ctcttactgt catgccatcc    6060
gtaagatgct tttctgtgac tggtgagtac tcaaccaagt cattctgaga atagtgtatg    6120
cggcgaccga gttgctcttg cccggcgtca atacgggata ataccgcgcc acatagcaga    6180
actttaaaag tgctcatcat tggaaaacgt tcttcggggc gaaaactctc aaggatctta    6240
ccgctgttga tccagttc gatgtaaccc actcgtgcac ccaactgatc ttcagcatct      6300
tttactttca ccagcgtttc tgggtgagca aaaacaggaa ggcaaaatgc cgcaaaaaag    6360
ggaataaggg cgacacggaa atgttgaata ctcatactct ccttttttca atattattga    6420
agcatttatc agggttattg tctcatgagc ggatacatat ttgaatgtat ttagaaaaat    6480
aaacaaatag gggttccgcg cacatttccc cgaaaagtgc cacctgacgt ctaagaaacc    6540
attattatca tgacattaac ctataaaaat aggcgtatca cgaggccctt tcgtctcgcg    6600
cgtttcggtg atgacggtga aaacctctga cacatgcagc tcccggagac ggtcacagct    6660
tgtctgtaag cggatgccgg gagcagacaa gcccgtcagg gcgcgtcagc gggtgttggc    6720
gggtgtcggg gctggcttaa ctatgcggca tcagagcaga ttgtactgag agtgcaccat    6780
atgcggtgtg aaataccgca cagatgcgta aggagaaaat accgcatcag gcgtaccata    6840
acttcgtata agtatcccta tacgaagtta tccatatgtg acagtaggcc caagggtctc    6900
gacttaattt cgttcacctg ctattgtctt cccaatcctc cccttgctg tcctgcccca     6960 ccccaccccc cagaatagaa tgacacctac tcagacaatg cgatgcaatt tcctcatttt    7020
attaggaaag gacagtggga gtggcacctt ccagggtcaa ggaaggcacg ggggaggggc    7080
aaacaacaga tggctggcaa ctagaaggca cagtcgaggc tgatcagcga tcgatgcagt    7140
catcagtcct gctcctcggc cacgaagtgc acgcagttgc cggccgggtc gcgcagggcg    7200
aactcccgcc cccacggctg ctcgccgatc tcggtcatgg ccggcccgga ggcgtcccgg    7260
aagttcgtgg acacgacctc cgaccactcg gcgtacagct cgtccaggcc gcgcacccac    7320
acccaggcca gggtgttgtc cggcaccacc tggtcctgga ccgcgctgat gaacagggtc    7380
acgtcgtccc ggaccacacc ggcgaagtcg tcctccacga agtcccggga gaacccgagc    7440
cggtcggtcc agaactcgac cgctccggcg acgtcgcgcg cggtgagcac cggaacggca    7500
ctggtcaact tggccatggt aagcttttg caaaagccta ggcctccaaa aaagcctcct    7560
```

| | |
|---|---:|
| cactacttct ggaatagctc agaggccgag gcggcctcgg cctctgcata aataaaaaaa | 7620 |
| attagtcagc catggggcgg agaatgggcg gaactgggcg gagttagggg cgggatgggc | 7680 |
| ggagttaggg gcgggactat ggttgctgac taattgagat gcatgctttg catacttctg | 7740 |
| cctgctgggg agcctgggga cttttccacac ctggttgctg actaattgag atgcatgctt | 7800 |
| tgcatacttc tgcctgctgg ggagcctggg gactttccac accctaactg acacacattc | 7860 |
| cacaggtcga ccactgtgct ggcgaattcc tactacggtc cccactag | 7908 |

```
<210> SEQ ID NO 15
<211> LENGTH: 10186
<212> TYPE: DNA
<213> ORGANISM: artificial sequence
<220> FEATURE:
<223> OTHER INFORMATION: chemically synthesized

<400> SEQUENCE: 15
```

| | |
|---|---:|
| gtagatgtac tgccaagtag gaaagtccca taaggtcatg tactgggcat aatgccaggc | 60 |
| gggccattta ccgtcattga cgtcaatagg gggcgtactt ggcatatgat acacttgatg | 120 |
| tactgccaag tgggcagttt accgtaaata ctccacccat tgacgtcaat ggaaagtccc | 180 |
| tattggcgtt actatgggaa catacgtcat tattgacgtc aatgggcggg ggtcgttggg | 240 |
| cggtcagcca gcggggccat ttaccgtaag ttatgtaacg cggaactcca tatatgggct | 300 |
| atgaactaat gaccccgtaa ttgattacta ttaataacta gccggttcaa ttgccgaccc | 360 |
| ctccccccaa cttctcgggg actgtgggcg atgtgcgctc tgcccactga cgggcaccgg | 420 |
| agctatatca agcttaccgc tatcggttgg aaaaccaacc gttcgcggtc tgtctggaca | 480 |
| ccgtcaacgg taaggacagc taccggacgc ggtctttaga cacaccgttg gcggttaggc | 540 |
| gtgccaccgt gatcggtaac tcatttcacc ggcaacggta tgggtacgaa ccgcctgcgg | 600 |
| tctatgtctg aaccgtgtcc ggtcagagtg gcgaccgctt ccggtgtcga cgtaccgggc | 660 |
| ccccccctcga ggtcgacggt atcgataagc tagcttgata tatctagttc tagcgaattc | 720 |
| tagtacccctc gacctgcagg tcgatcgact ctagtatggt gcactctcag tacaatctgc | 780 |
| tctgatgccg catagttaag ccagtatctg ctccctgctt gtgtgttgga ggtcgctgag | 840 |
| tagtgcgcga gcaaaattta agctacaaca aggcaaggct tgaccgacaa ttgcatgaag | 900 |
| aatctgctta gggttaggcg ttttgcgctg cttcgcgatg tacgggccag atatacgcgt | 960 |
| atctgagggg actagggtgt gtttaggcga aaagcggggc ttcggttgta cgcggttagg | 1020 |
| agtcccctca ggatatagta gtttcgcttt tgcataggga gggggaaatg tagtcttatg | 1080 |
| caatactctt gtagtcttgc aacatggtaa cgatgagtta gcaacatgcc ttacaaggag | 1140 |
| agaaaaagca ccgtgcatgc cgattggtgg aagtaaggtg gtacgatcgt gccttattag | 1200 |
| gaaggcaaca gacgggtctg acatggattg gacgaaccac tgaattccgc attgcagaga | 1260 |
| tattgtattt aagtgcctag ctcgatacaa taaacgccat tgaccattc accacattgg | 1320 |
| tgtgcacctc caagctggta gaggatcggt cgatcgactc tagacgccag aacacaggta | 1380 |
| agtgccgtgt gtggttcccg cgggcctggc ctctttacgg gttatggccc ttgcgtgcct | 1440 |
| tgaattactt ccacgcccct ggctgcagta cgtgattctt gatcccgagc ttcgggttgg | 1500 |
| aagtgggtgg gagagttcga ggccttgcgc ttaaggagcc ccttcgcctc gtgcttgagt | 1560 |
| tgaggcctgg cttgggcgct ggggccgccg cgtgcgaatc tggtggcacc ttcgcgcctg | 1620 |
| tctcgctgct ttcgataagt ctctagccat ttaaaatttt tgatgacctg ctgcgacgct | 1680 |
| ttttttctgg caagatagtc ttgtaaatgc gggccaagat ctgcacactg gtatttcggt | 1740 |

```
ttttggggcc gcgggcggcg acggggcccg tgcgtcccag cgcacatgtt cggcgaggcg    1800
gggcctgcga gcgcggccac cgagaatcgg acggggtag tctcaagctg gccggcctgc    1860
tctggtgcct ggcctcgcgc cgccgtgtat cgcccgccc tgggcggcaa ggctggcccg    1920
gtcggcacca gttgcgtgag cggaaagatg gccgcttccc ggccctgctg cagggagctc    1980
aaaatggagg acgcggcgct cgggagagcg ggcgggtgag tcacccacac aaaggaaaag    2040
ggcctttccg tcctcagccg tcgcttcatg tgactccacg gagtaccggg cgccgtccag    2100
gcacctcgat tagttctcga gcttttggag tacgtcgtct ttaggttggg gggaggggtt    2160
ttatgcgatg gagtttcccc acactgagtg ggtggagact gaagttaggc cagcttggca    2220
cttgatgtaa ttctccttgg aatttgccct ttttgagttt ggatcttggt tcattctcaa    2280
gcctcagaca gtggttcaaa gttttttct tccatttcag gtgtcgtgtc tagagcggcc    2340
gccaccgaaa cgccgtaccg ccaccatgga gtggtcttgg gtgttcctgt tctttctgtc    2400
cgtgaccaca ggcgtccaca gcgaagtgca actggtggaa agcggcggag gactcgtcca    2460
acctggaggc tccctcagac tgtcctgcgc cgcgagcgga ttcaacatca agacaccta    2520 tatccactgg gtcaggcaag cccctggcaa aggactggag tgggtcgcca ggatctaccc    2580
caccaatgga tacaccaggt acgctgacag cgtgaaaggc aggttcacaa tctccgccga    2640
caccagcaaa aacaccgcct atctccagat gaactccctg agggccgagg ataccgccgt    2700
ctactactgc agcaggtggg gaggcgacgg cttctacgcc atggattatt ggggacaagg    2760
caccctggtg accgtcagct ccgcttcgac caagggacct agcgtgttcc ctctggcccc    2820
cagcagcaag tctaccagcg gcggaacagc cgccctgggc tgcctggtca aggactactt    2880
ccccgagccc gtgaccgtgt cctggaacag cggagccctg acaagcggag tgcacacctt    2940
ccctgccgtg ctgcagtcca gcggcctgta tagcctgagc agcgtcgtga ccgtgcctag    3000
cagcagcctg ggcacccaga cctacatctg caacgtgaac cacaagccca gcaacaccaa    3060
ggtggacaag aaggtggagc ccaagagctg cgacaagacc catacctgcc cccttgtcc    3120 tgcccctgag ctgctgggcg gacccagcgt gtttctgttc cccccaagc caaggacac    3180 cctgatgatc agccggaccc ccgaagtgac ctgcgtggtg gtggatgtgt cccacgagga    3240
ccctgaagtg aagttcaatt ggtacgtgga cggcgtggag gtgcacaacg ccaagaccaa    3300
gccccgggag gaacagtaca acagcaccta ccgggtggtg tccgtgctga ccgtgctgca    3360
ccaggactgg ctgaacggca agaatacaa gtgcaaggtg tccaacaagg ccctgcctgc    3420
ccccatcgag aaaaccatca gcaaggccaa gggccagccc agagaacccc aggtgtacac    3480
cctgcctccc agcagagatg agctgaccaa gaaccaggtg tccctgacct gcctcgtgaa    3540
gggcttctac ccctccgata tcgccgtgga gtgggagagc aacggccagc ctgagaacaa    3600
ctacaagacc accccccctg tgctggatag cgacggcagc ttcttcctgt acagcaagct    3660
gaccgtggac aagagcagat ggcagcaggg caacgtgttc agctgcagcg tgatgcacga    3720
ggccctgcac aaccactaca cccagaagtc cctgagcctg agccccggca gtgatgaac    3780 cggtggcgcg cctagccggc cgcgacatga taagatacat tgatgagttt ggacaaacca    3840
caactagaat gcagtgaaaa aaatgcttta tttgtgaaat ttgtgatgct attgctttat    3900
ttgtgaaatt tgtgatgcta ttgctttatt tgtaaccatt ataagctgca ataaacaagt    3960
taacaacaac aattgcattc attttatgtt tcaggttcag ggggaggtgt gggaggtttt    4020
ttaaagcaag taaaacctct acaaatgtgg tagatcattt aaatgttaat tgtgtcgaca    4080
```

```
ggatcctata acttcgtata gcatacatta tacgaagtta tcagacaccc agtgtcgaac    4140
aacacctgac cgcgttgctg gcgttttttcc ataggctccg ccccctgac gagcatcaca    4200 aaaatcgacg ctcaagtcag aggtggcgaa acccgacagg actataaaga taccaggcgt    4260 ttcccctgg aagctccctc gtgcgctctc ctgttccgac cctgccgctt accggatacc    4320
tgtccgcctt tctcccttcg ggaagcgtgg cgctttctca tagctcacgc tgtaggtatc    4380
tcagttcggt gtaggtcgtt cgctccaagc tgggctgtgt gcacgaaccc cccgttcagc    4440
ccgaccgctg cgccttatcc ggtaactatc gtcttgagtc caacccggta agacacgact    4500
tatcgccact ggcagcagcc actggtaaca ggattagcag agcgaggtat gtaggcggtg    4560
ctacagagtt cttgaagtgg tggcctaact acggctacac tagaaggaca gtatttggta    4620
tctgcgctct gctgaagcca gttaccttcg gaaaaagagt tggtagctct tgatccggca    4680
aacaaaccac cgctggtagc ggtggttttt tgtttgcaa gcagcagatt acgcgcagaa    4740
aaaaaggatc tcaagaagat cctttgatct tttctacggg gtctgacgct cagtggaacg    4800
aaaactcacg ttaagggatt ttggtcatga gattatcaaa aaggatcttc acctagatcc    4860
ttttaaatta aaaatgaagt tttaaatcaa tctaaagtat atatgagtaa acttggtctg    4920
acagttacca atgcttaatc agtgaggcac ctatctcagc gatctgtcta tttcgttcat    4980
ccatagttgc ctgactcccc gtcgtgtaga taactacgat acgggagggc ttaccatctg    5040
gccccagtgc tgcaatgata ccgcgagacc cacgctcacc ggctccagat ttatcagcaa    5100
taaaccagcc agccggaagg gccgagcgca gaagtggtcc tgcaacttta tccgcctcca    5160
tccagtctat taattgttgc cgggaagcta gagtaagtag ttcgccagtt aatagtttgc    5220
gcaacgttgt tgccattgct acaggcatcg tggtgtcacg ctcgtcgttt ggtatggctt    5280
cattcagctc cggttcccaa cgatcaaggc gagttacatg atcccccatg ttgtgcaaaa    5340
aagcggttag ctccttcggt cctccgatcg ttgtcagaag taagttggcc gcagtgttat    5400
cactcatggt tatggcagca ctgcataatt ctcttactgt catgccatcc gtaagatgct    5460
tttctgtgac tggtgagtac tcaaccaagt cattctgaga atagtgtatg cggcgaccga    5520
gttgctcttg cccggcgtca atacgggata ataccgcgcc acatagcaga actttaaaag    5580
tgctcatcat tggaaaacgt tcttcggggc gaaaactctc aaggatctta ccgctgttga    5640
gatccagttc gatgtaaccc actcgtgcac ccaactgatc ttcagcatct tttactttca    5700
ccagcgtttc tgggtgagca aaaacaggaa ggcaaaatgc cgcaaaaaag ggaataaggg    5760
cgacacggaa atgttgaata ctcatactct ccttttttca atattattga agcatttatc    5820
agggttattg tctcatgagc ggatacatat ttgaatgtat ttagaaaaat aaacaaatag    5880
gggttccgcg cacatttccc cgaaaagtgc cacctgacgt ctaagaaacc attattatca    5940
tgacattaac ctataaaaat aggcgtatca cgaggccctt tcgtctcgcg cgtttcggtg    6000
atgacggtga aaacctctga cacatgcagc tcccggagac ggtcacagct tgtctgtaag    6060
cggatgccgg gagcagacaa gcccgtcagg gcgcgtcagc gggtgttggc gggtgtcggg    6120
gctggcttaa ctatgcggca tcagagcaga ttgtactgag agtgcaccat atgcggtgtg    6180
aaataccgca cagatgcgta aggagaaaat accgcatcag gcgtaccata acttcgtata    6240
aagtatccta tacgaagtta tccatatgtg acagtaggcc caagggtctc gacttaattt    6300
cgttcacctg ctattgtctt cccaatcctc cccttgctg tcctgcccca ccccacccc     6360 cagaatagaa tgacacctac tcagacaatg cgatgcaatt tcctcatttt attaggaaag    6420
gacagtggga gtggcacctt ccagggtcaa ggaaggcacg ggggaggggc aaacaacaga    6480
```

```
tggctggcaa ctagaaggca cagtcgaggc tgatcagcga tcgatgcatc atcagtcctg   6540
ctcctcggcc acgaagtgca cgcagttgcc ggccgggtcg cgcagggcga actcccgccc   6600
ccacggctgc tcgccgatct cggtcatggc cggcccggag gcgtcccgga agttcgtgga   6660
cacgacctcc gaccactcgg cgtacagctc gtccaggccg cgcacccaca cccaggccag   6720
ggtgttgtcc ggcaccacct ggtcctggac cgcgctgatg aacagggtca cgtcgtcccg   6780
gaccacaccg gcgaagtcgt cctccacgaa gtcccgggag aacccgagcc ggtcggtcca   6840
gaactcgacc gctccggcga cgtcgcgcgc ggtgagcacc ggaacggcac tggtcaactt   6900
ggccatggta agcttttttgc aaaagcctag gcctccaaaa aagcctcctc actacttctg   6960
gaatagctca gaggccgagg cggcctcggc ctctgcataa ataaaaaaaa ttagtcagcc   7020
atggggcgga gaatgggcgg aactgggcgg agttaggggc gggatgggcg gagttagggg   7080
cgggactatg gttgctgact aattgagatg catgctttgc atacttctgc ctgctgggga   7140
gcctggggac tttccacacc tggttgctga ctaattgaga tgcatgcttt gcatacttct   7200
gcctgctggg gagcctgggg actttccaca ccctaactga cacacattcc acaggtcgac   7260
cactgtgctg gcgaattcct actacggtcc ccatggagcc taggacccag cgagcccgtc   7320
gccgccgcgg cggcgccgcc cggggtctg cgagcagacc gaaaaggtca cactctgggg   7380
cgcgcgaccc gcccgagtca gcggcccgcc agttaccacc cgccgaccaa accccgcct   7440 ccacggaggg cggggggtg cttaagagga tcgcggcgct cttctgcgtg cccgtggcca   7500
ccaagaccaa accccgagcc gcctccgaat gagagtgttt cgttccttcc ccctcccccc   7560
gcgtcagaca aaccctaacc accgcttaag cggccccgc gaggtccgaa gactcatttc   7620
gtactcgtcg acagcccaga ccccacgcaa cgcccaaaat aataacccc acgaaccata   7680 aaccattccc catggggacc ccgtccctaa cccacggggc cagtggctat ggcagggcct   7740
gccgccccga cgttggctgc gagccctggg ccttcacccg aacttggggg gtggggtggg   7800
gaaaaggaag aaacgcgggc gtattggccc caatgggtc tcggtggggt atcgacagag   7860
tgccagccct gggaccgaac cccgcgttta tgaacaaacg acccaacacc cgtgcgtttt   7920
attctgtctt tttattgccg tcatagcgcg ggttccttcc ggtattgtct ccttccgtgt   7980
ttcagttagc ctccccccatc tccttaatta agccggtcat cagcactcgc cccggttgaa   8040
gctcttggtc acgggctgg acaggccctg gtgggtcact tcgcaggcgt acaccttgtg   8100
cttctcgtag tcggccttgc tcagggtcag ggtgctgctc aggctgtagg tggagtcctt   8160
gctgtcctgc tcggtgacgc tttcctggct gttgccggac tgcagggcgt tgtccacctt   8220
ccactgcacc ttggcctccc ggggggtagaa gttgttcagc aggcacacga cgctggcggt   8280
gccggacttc agctgctcgt cgctgggggg gaagatgaac acgcttggag cagcaacggt   8340
tcgtttgatc tccacctttg tgccttggcc gaaggtgggg ggggttgtgt aatgctgctg   8400
gcagtagtag gtggcaaaat cctcgggttg caggctggag attgtcagtg tgaagtcggt   8460
tccggacctg gagccggaaa atctggaagg cacgccgcta tacaggaagg aggcgctata   8520
gatgagcagc ttgggagcct tgccaggttt ctgctggtac caagccacgg ctgtgttcac   8580
atcctggctg gccctgcagg taatggtcac cctatctccc acggaagcgg acagggagga   8640
gggggactgt gtcatctgaa tgtcgcacct ggcgtctgtc agccacagca gcagcaggcc   8700
caggacctgg gtgggcacgg acatggtggc ttcgccggac ttgtacgcta gaagggtacg   8760
gcgtttcggt ggcggccgct agatcggatc ctgcagaatt ccaccacact ggactagaat   8820
```

-continued

```
tctttgccaa aatgatgaga cagcacaata accagcacgt tgcccaggag ctgtaggaaa      8880
aagaagaagg catgaacatg gttagcagag gctctagagc cgccggtcac acgccagaag      8940
ccgaaccccg ccctgccccg tccccccga aggcagccgt cccccgcgg acagccccga        9000
ggctggagag ggagaagggg acggcggcgc ggcgacgcac gaaggccctc ccgcccatt       9060
tccttcctgc cggcgccgca ccgcttcgcc ccgcgcccgc tagagggggt gcggcggcgc      9120
ctcccagatt tcggctccgc acagatttgg gacaaaggaa gtccctgcgc cctctcgcac      9180
gattaccata aaaggcaatg gctgcggctc gccgcgcctc gacagccgcc ggcgctccgg      9240
gggccgccgc gcccctcccc cgagccctcc ccggcccgag gcggcccgc ccgcccggc        9300
accccacct gccgccaccc cccgcccggc acggcgagcc ccgcgccacg ccccgtacgg       9360
agccccgcac ccgaagccgg gccgtgctca gcaactcggg gagggggtg caggggggt        9420
tgcagcccga ccgacgcgcc cacaccccct gctcaccccc ccacgcacac accccgcacg     9480
cagcctttgt tccctcgca gcccccccg caccgcgggg caccgccccc ggccgcgctc       9540
cccctcgcgca cactgcggag cgcacaaagc cccgcgccgc gcccgcagcg ctcacagccg    9600
ccgggcagcg cggagccgca cgcggcgctc cccacgcaca cacacacgca cgcaccccc      9660
gagccgctcc ccccgcacaa agggccctcc cggagcccct caaggctttc acgcagccac    9720
agaaaagaaa caagccgtca ttaaaccaag cgctaattac agcccggagg agaagggccg    9780
tcccgcccgc tcacctgtgg gagtaacgcg gtcagtcaga gccggggcgg gcggcgcgag     9840
gcggcggcgg agcggggcac ggggcgaagg cagcgcgcag cgactcccgc ccgccgcgcg    9900
cttcgctttt tatagggccg ccgccgccgc cgcctcgcca taaaaggaaa ctttcggagc    9960
gcgccgctct gattggctgc cgccgcacct ctccgcctcg ccccgccccg ccctcgccc    10020
cgccccgccc cgcctggcgc gcgccccccc ccccgcccc catcgctgca caaaataatt   10080
aaaaaataaa taaatacaaa attggggtg gggaggggg ggagatgggg agagtgaagc    10140
agaacgtggg gctcacctcg accatggtaa tagcgatgac taatac                  10186
```

<210> SEQ ID NO 16
<211> LENGTH: 519
<212> TYPE: PRT
<213> ORGANISM: Homo sapiens

<400> SEQUENCE: 16

```
Met Leu Leu Leu Leu Leu Leu Gly Leu Arg Leu Gln Leu Ser Leu
1               5                   10                  15

Gly Ile Ile Pro Val Glu Glu Asn Pro Asp Phe Trp Asn Arg Glu
                20                  25                  30

Ala Glu Ala Leu Gly Ala Ala Lys Lys Leu Gln Pro Ala Gln Thr
            35                  40                  45

Ala Ala Lys Asn Leu Ile Ile Phe Leu Gly Asp Gly Met Gly Val Ser
        50                  55                  60

Thr Val Thr Ala Ala Arg Ile Leu Lys Gly Gln Lys Lys Asp Lys Leu
65                  70                  75                  80

Gly Pro Glu Ile Pro Leu Ala Met Asp Arg Phe Pro Tyr Val Ala Leu
                85                  90                  95

Ser Lys Thr Tyr Asn Val Asp Lys His Val Pro Asp Ser Gly Ala Thr
                100                 105                 110

Ala Thr Ala Tyr Leu Cys Gly Val Lys Gly Asn Phe Gln Thr Ile Gly
            115                 120                 125

Leu Ser Ala Ala Ala Arg Phe Asn Gln Cys Asn Thr Thr Arg Gly Asn
```

```
            130                 135                 140
Glu Val Ile Ser Val Met Asn Arg Ala Lys Lys Ala Gly Lys Ser Val
145                 150                 155                 160

Gly Val Val Thr Thr Thr Arg Val Gln His Ala Ser Pro Ala Gly Thr
                165                 170                 175

Tyr Ala His Thr Val Asn Arg Asn Trp Tyr Ser Asp Ala Asp Val Pro
                180                 185                 190

Ala Ser Ala Arg Gln Glu Gly Cys Gln Asp Ile Ala Thr Gln Leu Ile
                195                 200                 205

Ser Asn Met Asp Ile Asp Val Ile Leu Gly Gly Arg Lys Tyr Met
210                 215                 220

Phe Arg Met Gly Thr Pro Asp Pro Glu Tyr Pro Asp Tyr Ser Gln
225                 230                 235                 240

Gly Gly Thr Arg Leu Asp Gly Lys Asn Leu Val Gln Glu Trp Leu Ala
                245                 250                 255

Lys Arg Gln Gly Ala Arg Tyr Val Trp Asn Arg Thr Glu Leu Met Gln
                260                 265                 270

Ala Ser Leu Asp Pro Ser Val Thr His Leu Met Gly Leu Phe Glu Pro
                275                 280                 285

Gly Asp Met Lys Tyr Glu Ile His Arg Asp Ser Thr Leu Asp Pro Ser
                290                 295                 300

Leu Met Glu Met Thr Glu Ala Ala Leu Arg Leu Leu Ser Arg Asn Pro
305                 310                 315                 320

Arg Gly Phe Phe Leu Phe Val Glu Gly Gly Arg Ile Asp His Gly His
                325                 330                 335

His Glu Ser Arg Ala Tyr Arg Ala Leu Thr Glu Thr Ile Met Phe Asp
                340                 345                 350

Asp Ala Ile Glu Arg Ala Gly Gln Leu Thr Ser Glu Glu Asp Thr Leu
                355                 360                 365

Ser Leu Val Thr Ala Asp His Ser His Val Phe Ser Phe Gly Gly Tyr
                370                 375                 380

Pro Leu Arg Gly Ser Ser Ile Phe Gly Leu Ala Pro Gly Lys Ala Arg
385                 390                 395                 400

Asp Arg Lys Ala Tyr Thr Val Leu Leu Tyr Gly Asn Gly Pro Gly Tyr
                405                 410                 415

Val Leu Lys Asp Gly Ala Arg Pro Asp Val Thr Glu Ser Glu Ser Gly
                420                 425                 430

Ser Pro Glu Tyr Arg Gln Gln Ser Ala Val Pro Leu Asp Glu Glu Thr
                435                 440                 445

His Ala Gly Glu Asp Val Ala Val Phe Ala Arg Gly Pro Gln Ala His
                450                 455                 460

Leu Val His Gly Val Gln Glu Gln Thr Phe Ile Ala His Val Met Ala
465                 470                 475                 480

Phe Ala Ala Cys Leu Glu Pro Tyr Thr Ala Cys Asp Leu Ala Pro Pro
                485                 490                 495

Ala Gly Thr Thr Asp Ala Ala His Pro Gly Tyr Ser Arg Val Gly Ala
                500                 505                 510

Ala Gly Arg Phe Glu Gln Thr
                515

<210> SEQ ID NO 17
<211> LENGTH: 24
<212> TYPE: PRT
<213> ORGANISM: Foot and mouth disease virus
```

<400> SEQUENCE: 17

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 18
<211> LENGTH: 344
<212> TYPE: PRT
<213> ORGANISM: artificial sequence
<220> FEATURE:
<223> OTHER INFORMATION: chemically synthesized

<400> SEQUENCE: 18

Lys Lys Pro Glu Leu Thr Ala Thr Ser Val Glu Lys Phe Leu Ile Glu
1               5                   10                  15

Lys Phe Asp Ser Val Ser Asp Leu Met Gln Leu Ser Glu Gly Glu Glu
                20                  25                  30

Ser Arg Ala Phe Ser Phe Asp Val Gly Gly Arg Gly Tyr Val Leu Arg
            35                  40                  45

Val Asn Ser Cys Ala Asp Gly Phe Tyr Lys Asp Arg Tyr Val Tyr Arg
50                  55                  60

His Phe Ala Ser Ala Ala Leu Pro Ile Pro Glu Val Leu Asp Ile Gly
65                  70                  75                  80

Glu Phe Ser Glu Ser Leu Thr Tyr Cys Ile Ser Arg Arg Ala Gln Gly
                85                  90                  95

Val Thr Leu Gln Asp Leu Pro Glu Thr Glu Leu Pro Ala Val Leu Gln
            100                 105                 110

Pro Val Ala Glu Ala Met Asp Ala Ile Ala Ala Asp Leu Ser Gln
        115                 120                 125

Thr Ser Gly Phe Gly Pro Phe Gly Pro Gln Gly Ile Gly Gln Tyr Thr
130                 135                 140

Thr Trp Arg Asp Phe Ile Cys Ala Ile Ala Asp Pro His Val Tyr His
145                 150                 155                 160

Trp Gln Thr Val Met Asp Asp Thr Val Ser Ala Ser Val Ala Gln Ala
                165                 170                 175

Leu Asp Glu Leu Met Leu Trp Ala Glu Asp Cys Pro Glu Val Arg His
            180                 185                 190

Leu Val His Ala Asp Phe Gly Ser Asn Asn Val Leu Thr Asp Asn Gly
        195                 200                 205

Arg Ile Thr Ala Val Ile Asp Trp Ser Glu Ala Met Phe Gly Asp Ser
210                 215                 220

Gln Tyr Glu Val Ala Asn Ile Phe Phe Trp Arg Pro Trp Leu Ala Cys
225                 230                 235                 240

Met Glu Gln Gln Thr Arg Tyr Phe Glu Arg Arg His Pro Glu Leu Ala
                245                 250                 255

Gly Ser Pro Arg Leu Arg Ala Tyr Met Leu Arg Ile Gly Leu Asp Gln
            260                 265                 270

Leu Tyr Gln Ser Leu Val Asp Gly Asn Phe Asp Asp Ala Ala Trp Ala
        275                 280                 285

Gln Gly Arg Cys Asp Ala Ile Val Arg Ser Gly Ala Gly Thr Val Gly
    290                 295                 300

Arg Thr Gln Ile Ala Arg Arg Ser Ala Ala Val Trp Thr Asp Gly Cys
305                 310                 315                 320

```
Val Glu Val Leu Ala Asp Ser Gly Asn Arg Pro Ser Thr Arg Pro
                325                 330                 335

Asp Arg Glu Met Gly Glu Ala Asn
            340
```

<210> SEQ ID NO 19
<211> LENGTH: 185
<212> TYPE: PRT
<213> ORGANISM: artificial sequence
<220> FEATURE:
<223> OTHER INFORMATION: chemically synthesized

<400> SEQUENCE: 19

```
Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
            20                  25                  30

Ser Asn Phe Ala Thr Thr Asp Leu Asp Ala Asp Arg Gly Lys Leu Pro
        35                  40                  45

Gly Lys Lys Leu Pro Leu Glu Val Leu Lys Glu Met Glu Ala Asn Ala
    50                  55                  60

Arg Lys Ala Gly Cys Thr Arg Gly Cys Leu Ile Cys Leu Ser His Ile
65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Ile Gly Glu Ala Ile
            100                 105                 110

Val Asp Ile Pro Glu Ile Pro Gly Phe Lys Asp Leu Glu Pro Met Glu
        115                 120                 125

Gln Phe Ile Ala Gln Val Asp Leu Cys Val Asp Cys Thr Thr Gly Cys
    130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
            180                 185
```

<210> SEQ ID NO 20
<211> LENGTH: 241
<212> TYPE: PRT
<213> ORGANISM: artificial sequence
<220> FEATURE:
<223> OTHER INFORMATION: chemically synthesized

<400> SEQUENCE: 20

```
Phe Glu Met Val Ser Lys Gly Glu Glu Leu Phe Thr Gly Val Val Pro
1               5                   10                  15

Ile Leu Val Glu Leu Asp Gly Asp Val Asn Gly His Lys Phe Ser Val
            20                  25                  30

Ser Gly Glu Gly Glu Gly Asp Ala Thr Tyr Gly Lys Leu Thr Leu Lys
        35                  40                  45

Phe Ile Cys Thr Thr Gly Lys Leu Pro Val Pro Trp Pro Thr Leu Val
    50                  55                  60

Thr Thr Leu Thr Tyr Gly Val Gln Cys Phe Ser Arg Tyr Pro Asp His
65                  70                  75                  80

Met Lys Gln His Asp Phe Phe Lys Ser Ala Met Pro Glu Gly Tyr Val
                85                  90                  95
```

Gln Glu Arg Thr Ile Phe Phe Lys Asp Asp Gly Asn Tyr Lys Thr Arg
            100                 105                 110

Ala Glu Val Lys Phe Glu Gly Asp Thr Leu Val Asn Arg Ile Glu Leu
            115                 120                 125

Lys Gly Ile Asp Phe Lys Glu Asp Gly Asn Ile Leu Gly His Lys Leu
            130                 135                 140

Glu Tyr Asn Tyr Asn Ser His Asn Val Tyr Ile Met Ala Asp Lys Gln
145                 150                 155                 160

Lys Asn Gly Ile Lys Val Asn Phe Lys Ile Arg His Asn Ile Glu Asp
            165                 170                 175

Gly Ser Val Gln Leu Ala Asp His Tyr Gln Gln Asn Thr Pro Ile Gly
            180                 185                 190

Asp Gly Pro Val Leu Leu Pro Asp Asn His Tyr Leu Ser Thr Gln Ser
            195                 200                 205

Ala Leu Ser Lys Asp Pro Asn Glu Lys Arg Asp His Met Val Leu Leu
            210                 215                 220

Glu Phe Val Thr Ala Ala Gly Ile Thr Leu Gly Met Asp Glu Leu Tyr
225                 230                 235                 240

Lys

<210> SEQ ID NO 21
<211> LENGTH: 550
<212> TYPE: PRT
<213> ORGANISM: artificial sequence
<220> FEATURE:
<223> OTHER INFORMATION: chemically synthesized

<400> SEQUENCE: 21

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
            35                  40                  45

Val Asp Ile Thr Tyr Ala Glu Tyr Phe Glu Met Ser Val Arg Leu Ala
        50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
            115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
            165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
            195                 200                 205

```
Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Gly Phe Phe Ala Lys Ser Thr Leu Ile Asp Lys Tyr
290                 295                 300

Asp Leu Ser Asn Leu His Glu Ile Ala Ser Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
530                 535                 540

Gly Gly Lys Ile Ala Val
545                 550

<210> SEQ ID NO 22
<211> LENGTH: 181
<212> TYPE: DNA
<213> ORGANISM: artificial sequence
<220> FEATURE:
<223> OTHER INFORMATION: chemically synthesized

<400> SEQUENCE: 22
accgttgccg gtcggatctg taccgttgcc ggtcggatct gtaccgttgc cggtcggatc      60
tgtaccgttg ccgtcggat ctgtaccgtt gccggtcgga tctgtaccgt tgccggtcgg     120
```

-continued

```
atctgtaccg ttgccggtcg gatctgtacc gttgccggtc ggatctgtac cgttgccggt      180
c                                                                     181

<210> SEQ ID NO 23
<211> LENGTH: 210
<212> TYPE: DNA
<213> ORGANISM: artificial sequence
<220> FEATURE:
<223> OTHER INFORMATION: chemically synthesized

<400> SEQUENCE: 23
agcttcagaa gatggcggag ggcctccaac acagtaattt cctcccgac agatctccta       60 gaatgtttcc acccaatcat tactatgaca acagctgttt tttttagtat taagcagagg    120 ccggggggccc ctggcctccg cttactctgg agaaaaagaa gagaggcatt gtagaggctt    180
ccagaggcaa cttgtcaaaa caggactggc                                     210

<210> SEQ ID NO 24
<211> LENGTH: 622
<212> TYPE: DNA
<213> ORGANISM: artificial sequence
<220> FEATURE:
<223> OTHER INFORMATION: chemically synthesized

<400> SEQUENCE: 24
taatgttgcc atgggtagca tatactaccc aaatatctgg atagcatatg ctatcctaat     60
ctatatctgg gtagcatagg ctatcctaat ctatatctgg gtagcatatg ctatcctaat    120
ctatatctgg gtagtatatg ctatcctaat ttatatctgg gtagcatagg ctatcctaat    180
ctatatctgg gtagcatatg ctatcctaat ctatatctgg gtagtatatg ctatcctaat    240
ctgtatccgg gtagcatatg ctatcctaat agagattagg gtagtatatg ctatcctaat    300
ttatatctgg gtagcatata ctacccaaat atctggatag catatgctat cctaatctat    360
atctgggtag catatgctat cctaatctat atctgggtag cataggctat cctaatctat    420
atctgggtag catatgctat cctaatctat atctgggtag tatatgctat cctaatttat    480
atctgggtag cataggctat cctaatctat atctgggtag catatgctat cctaatctat    540
atctgggtag tatatgctat cctaatctgt atccgggtag catatgctat cctcatgcgt    600
atacagtcag catatgatac cc                                            622

<210> SEQ ID NO 25
<211> LENGTH: 194
<212> TYPE: DNA
<213> ORGANISM: artificial sequence
<220> FEATURE:
<223> OTHER INFORMATION: chemically synthesized

<400> SEQUENCE: 25
gtaagtggcg tttctcgggg agccagctgc gtccgctgtc gtgctgtcgg tgtagtacta     60
gcaagcgtta agtccccatc tggctgcggc ctaccgaaga gtggtcttca cgtcacacgc    120
tgtcccacgc acgtggttgg tttggtcgct tctggttact gactactaag cagccttttc    180
ttttttcctt tcag                                                     194

<210> SEQ ID NO 26
<211> LENGTH: 258
<212> TYPE: DNA
<213> ORGANISM: artificial sequence
<220> FEATURE:
```

```
<223> OTHER INFORMATION: chemically synthesized

<400> SEQUENCE: 26
cgacatgata agatacattg atgagtttgg acaaaccaca actagaatgc agtgaaaaaa      60
atgctttatt tgtgaaattt gtgatgctat tgctttattt gtgaaatttg tgatgctatt     120
gctttatttg taaccattat aagctgcaat aaacaagtta acaacaacaa ttgcattcat     180
tttatgtttc aggttcaggg ggaggtgtgg gaggtttttt aaagcaagta aaacctctac     240
aaatgtggta gatcattt                                                   258
```

PLATFORM FOR DEVELOPING STABLE MAMMALIAN CELL LINES

PRIORITY

This application claims the priority of U.S. provisional application No. 62/747,158 filed on Oct. 18, 2018 the contents of which is fully incorporated herein by reference.

BACKGROUND OF THE INVENTION

About 20-30% of new drugs approved by European Medicines Agency (EMA) and US Food and Drug Administration (FDA) are biologics (biopharmaceuticals, biotherapeutics). In addition to approved biopharmaceuticals, a large number of biologic drugs are under development and in the pipeline for approval. To produce these products in large quantities, good and robust expression systems are needed for discovery, development and manufacturing of drug candidates.

Production of therapeutic proteins such as monoclonal antibodies, peptides and recombinant proteins is challenging as most of the biologics are proteins with complex post-translational modifications. To achieve proper modification, the protein production using mammalian cells is required. Chinese hamster ovary (CHO) cells are used for the majority of products, both on the market and in clinical development, as the products produced in these cells are safe, efficient, and have a similar glycosylation pattern as human proteins (Zhu, 2012). In addition, CHO cells can grow in chemically defined serum-free media and cultivated in suspension culture, meaning that the protein production in CHO cells can easily be scaled-up which is crucial for industrial manufacturing of therapeutics.

To continuously produce biologics, stable high-producer cell lines need to be generated. Historically, such cell lines have been produced by random integration of gene-of-interest expression cassette to the genome, followed by selection with antibiotic compound and cassette amplification using either glutamine synthetase/MSX or dihydrofolate reductase/MTX systems (Bebbington et al., 1992; Kaufman and Sharp, 1982). For both systems, knock-out cell lines have been generated (Liu et al., 2010; Urlaub and Chasin, 1980; Wigler et al., 1980). However, stable cell line development using gene amplification approach is time consuming and always requires lot of effort as the selected pools are heterogeneous. Single-cell cloning of selected pools is necessary to identify rare high-producer clones. Furthermore, proofing of "monoclonality" of production cell line is required for the safety and efficiency of the produced protein (Frye et al., 2016). Stability of generated cell line(s) can be tested in the end of development and unfortunately, due to lack of control of insertion sites in random integration, protein productivity of some clones could be high in the beginning of the development but may diminish over time, causing instability of cell lines. This means that several clonal cell lines need to be generated and tested for further stability studies which naturally makes development work slow and expensive.

Accordingly, the cell line development with classical random integration is a long and costly process. Mostly, the high cost is caused by large number of clones that need to be screened in order to get a suitable cell line and therefore, development of cell lines for production of therapeutics in large-scale is often unaffordable for small and medium size enterprises. Use of site-specific or targeted integration that improves development efficiency is a promising strategy which could reduce the price of stable cell line generation. Therefore, there is a need for new cell line development technologies, based on the targeted integration of a transgene for decreasing the number of clones to be screened and by that, to reduce the price of whole process.

Several enzymes can be used to achieve targeted integration of a transgene expression cassette to the cells—e.g., site-specific recombinases (Cre, Flp or BxB1), engineered nucleases (TALENs or zinc-finger nucleases), or the most recently developed tool, CRISPR-Cas9 system. The usage of site-specific recombinases like Cre, Flp or BxB1 needs introduction of specific recognition sequence(s) to the host cell genome and after that, the gene-of-interest expression cassette can be targeted into the same locus. For example, in the Flp-in system provided by Thermo Fisher Scientific, a single Flp-recognition (FRT) site is introduced in host genome to integrate the expression plasmids containing the same recognition site. However, with this type of integration, together with a gene-of-interest sequence, unnecessary plasmid backbone consisting of bacterial origin of replication and antibiotic resistance gene that were used for molecular cloning purposes also integrate to eukaryotic cell genome. Bacterial sequences are unwanted in eukaryotic cells because their presence can lead to silencing of the locus of integration. However, if there are 2 different or incompatible recombinase target sites (e. g., a wild-type and a mutant site) in the host cells, the gene-of-interest expression vector containing the same set of recombination sites can be integrated by the recombination-mediated cassette exchange (RMCE) reaction. RMCE leads to replacement of the sequence between the recombination sites and to the excision of the regions outside of the recombination sites. RMCE does not leave behind extraneous vector sequences such as bacterial origin of replication and antibiotic resistance cassette needed for plasmid amplification in bacteria, as these elements can be placed outside of the recombination target sites. The use of recombinase mediated cassette exchange allows avoiding the integration of unnecessary regions into the mammalian cell genome. Therefore, transgene silencing, caused by co-integration bacterial elements, should not occur in RMCE cell line.

Some CHO based parental cell lines that can be used for stable cell line development through RMCE have already been shown to have good productivities of monoclonal antibodies after recombination (Inniss et al., 2017; Zhang et al., 2015). However, the repertoire of different cell lines is scarce and only a very few genomic hotspots in CHO cells such as Fer1L4 locus, have been tested in terms of productivity and stability (Zhang et al., 2015). Thus, there is still demand for new parental cell lines containing the integrated transgene in genomic hotspots.

In addition, the systems that help to target the transgenes to the transcriptionally active region are also needed for identifying superior genomic loci suitable for stable cell line development. Furthermore, it is crucial to uncover the mechanisms that help to increase the stable and transient expression of therapeutics in mammalian cells.

SUMMARY OF THE INVENTION

Here, a mammalian cell-based technology that allows for faster and more efficient production of recombinant proteins and biologic drugs compared to traditional random integration cell line development methods is disclosed. By creating parental landing pad cell lines that express the integrated reporter genes at high-yield for a long period of time and use these parental cell lines as platforms for making cell lines that produce protein of interest in a similar manner, it is possible to reduce the price of stable cell line development.

The present invention provides methods and constructs for developing parental cell lines that can be used for targeted integration to produce cell lines expressing protein-of-interest, such as antibodies or other recombinant proteins.

The parental cell lines are developed similarly to traditional methods, by random integration of the expression cassette to the cells. However, here an advantage is taken of the properties of the master transcriptional regulator of papillomaviruses, which is the E2-protein. Many different DNA viruses, including papillomaviruses, replicate as extra-chromosomal episomes. For efficient gene expression and replication, episomal viral genomes should be located to transcriptionally active regions of chromatin. The viral genomes are often transferred to these regions by viral proteins (e.g., BPV1 E2) that bind to their respective binding-sites (BS) located on viral genome. Here, we show that by inserting papillomavirus (e.g BPV1) E2 binding sites to landing pad cassette, in the presence of viral protein expression, the landing pad cassette is directed to transcriptionally active region of the chromatin prior to integration. E2 binding sites were added in the landing pad cassettes and when an BPV1 E2 expression vector is co-transfected with the landing pad or any other DNA that contains E2 binding sites (E2BS), it is possible to tether the vector to the transcriptionally active chromatin locus and thereby increase the chance that the construct integrates into an active genomic region ensuring stable high-yield expression of the integrated sequences.

Accordingly, it is an object of this invention to provide co-transfection of BPV1 E2 expression cassette and landing pad construct containing BPV1 E2 binding sites leading to generation of cell pools with higher expression of the reporter gene as compared to landing pads without the BPV1 E2 binding sites.

It is an object of the present invention to provide plasmid DNA sequence encoding bovine papillomavirus E2 protein for use in parental cell line development.

A further object of this invention is to provide increase in transcriptional activity of promoters that are in the proximity of BPV1 E2 binding sites, when the expression cassette of E2 protein is stably integrated to the cells and the cell line is expressing this protein.

It is an object of this invention to provide landing pad cassettes expressing detectable reporter genes for easy screening by high-throughput methods. These cassettes are flanked by recognition sites of site-specific recombinases, which makes possible to replace the cassette with another vector containing the same set of recognition sequences in a recombination-mediated cassette exchange (RMCE) reaction. For targeted integration via RMCE, the gene-of-interest vector need to be co-transfected with either the expression vector or mRNA of a site-specific recombinase.

Compared to parental cell line development by random integration, the generation of protein of interest cell line via targeted integration takes less time and energy since less clones need to be screened to find clones with suitable stability and productivity.

It is an object of this invention to provide high producer gene of interest (GOI) cell lines.

Another object of the invention is to provide parental cell lines containing integrated landing pad vector for use in development of high producer GOI-cell lines.

It is an object of this invention to provide landing pad vectors including recognition sites of site-specific recombinases. According to certain aspects of the invention the recognition sites may be Cre, Flp and BxB1 sites. According to certain aspects the landing pad vectors encode one or more reporter proteins, enabling the screening of best producing clones.

According to certain aspects based on the expression of reporter genes, the clonal cell lines with high-yield expression of reporter genes can be screened out to generate the parental cell lines.

According to certain aspects of the parental cell lines will be characterized and the well-described parental cell lines with a single integration of the landing pad vector are used in recombination-mediated cassette exchange to replace the landing pad vector with a gene-of-interest expression vector to generate the cell line with similar properties as the parental cells.

Accordingly, it is an object the invention to provide:

A landing pad construct having recognition sites of site-specific recombinases at both of its ends, and comprising: coding sequences for at least one reporter gene coding for a detectable reporter protein, coding sequences for at least one selection marker and papillomavirus E2 binding sites.

It is another object of the invention to provide a landing pad plasmid having a nucleotide sequence according to SEQ ID NO:1; SEQ ID NO:2 or SEQ ID NO:3.

It is an object to provide a cell line, comprising a landing pad plasmid having recognition sites of site-specific recombinases at both of its ends, and comprising: coding sequences for at least one reporter gene coding for a detectable reporter protein, coding sequences for at least one selection marker and coding sequences for BPV 1 E2 binding site.

A further object of the invention is to provide a cell line co-transfected with a landing pad plasmid having recognition sites of site-specific recombinases at both of its ends, and comprising: coding sequences for at least one reporter gene coding for a detectable reporter protein, coding sequences for at least one selection marker and coding sequences for BPV 1 E2 binding site and with an expression vector for BPV E2 protein.

It is another object of the invention to provide a method to develop high producer cell lines, said method comprising the steps of: providing a landing pad vector flanked by recognition sites of site-specific recombinases, and comprising coding sequences for at least one reporter gene and for papillomavirus E2 binding sites; providing an expression plasmid of BPV1 E2 protein; co-transfecting a cell with the landing pad vector and the expression plasmid; allowing expression from the landing pad vector and the expression vector, whereby targeting of the landing pad vector to transcriptionally active regions of the chromatin is improved; and selecting the cells with highest production a parental cell lines.

Still another object of the invention is to provide a method for high stable production of a gene of interest, said method comprising the steps of developing a high producer cell line by way of co-transfecting a cell line with a landing pad vector flanked by recognition sites of site-specific recombinases, and comprising coding sequences for at least one reporter gene and for BPV1 E2 binding site, and with an expression plasmid of BPV1 E2 protein; providing a gene of interest vector comprising same recognition sites of site-specific recombinases as the landing pad vector; replacing the landing pad vector with the gene of interest vector by co-transfecting the cell line with the gene of interest vector and an expression vector or mRNA for site-specific recombinases recognized by the recognition sites, and cultivating the cell line in environment suitable for protein expression.

It is yet another object of this invention to provide a kit comprising, a landing pad vector flanked by recognition sites of site-specific recombinases, and comprising coding sequences for at least one reporter gene and for BPV1 E2 sites and with an expression plasmid of BPV1 E2 protein(s); a gene of interest vector comprising same recognition sites of site-specific recombinases as the landing pad vector; and a suitable cell line for co-transfection.

Further objects and aspects of the invention are described in the following drawings and detailed disclosure of the invention.

SHORT DESCRIPTION OF THE FIGURES

FIG. 1. Generic scheme of landing pad cell line development. Each box on the scheme characterizes one stage in a classical stable cell line development process.

Figure 2:
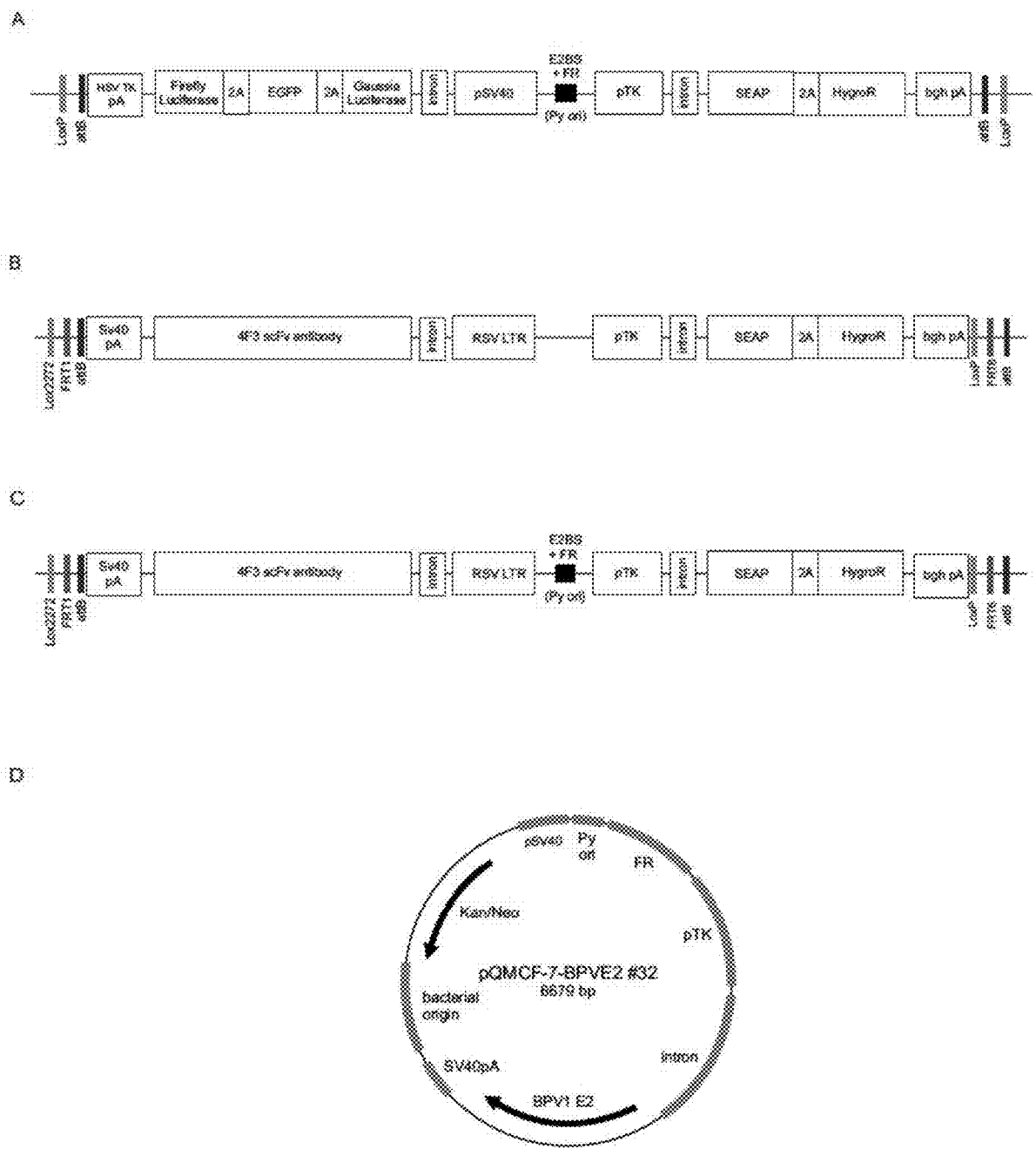

FIG. 2. Schemes of constructs used in parental cell line development. A) LP2str #132; B) LP2str_4F3_wo BS #3; C) LP2str_4F3_CAR #182; D) pQMCF-7-BPVE2 #32. Figures A-C illustrate different landing pad constructs that are flanked by recombination target sites and encode for detectable reporter genes and antibiotic resistance gene. These cassettes can be used in parental cell line development for identifying suitable clonal cell lines that can later be used for protein of interest cell line generation. Figure D illustrates pQMCF-7-BPVE2 #32 vector encoding for BPV1 E2 protein that enables targeting the landing pad vectors to transcriptionally active region.

Figure 3:
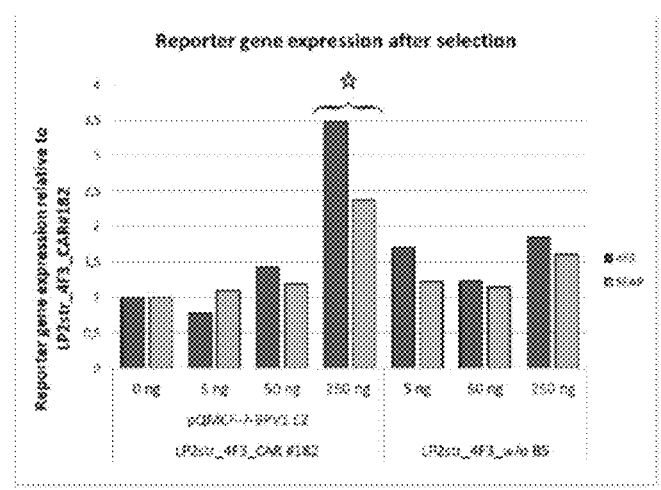

FIG. 3. ELISA assay for evaluating the role of BPV1 E2 in reporter gene 4F3 scFv expression in selected cell pools. Results are presented relative to LP2str 4F3_CAR #182 transfection. Marked cell pool, expressing 4F3 scFv at highest level, was selected to be used in parental cell line development.

Figure 4:
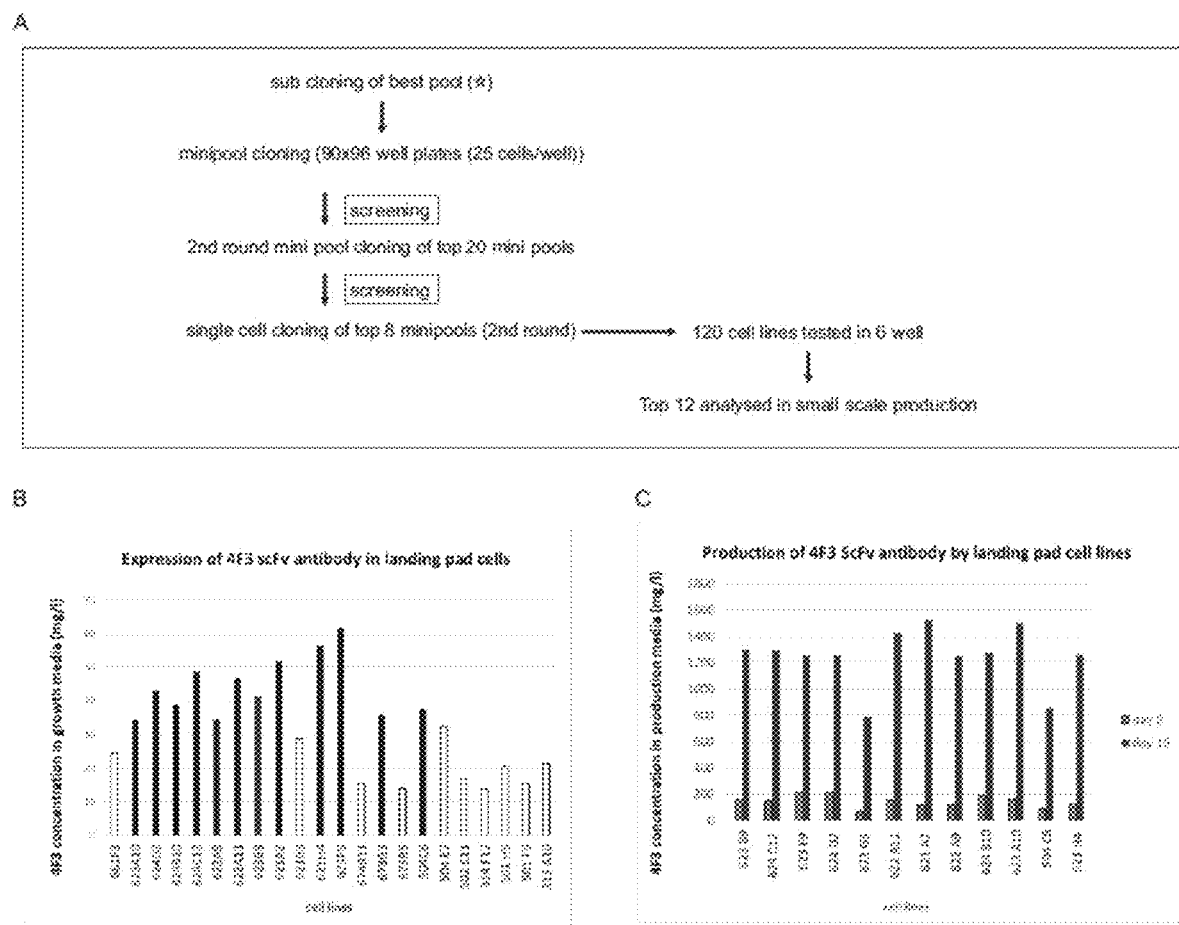

FIG. 4. Example of a landing pad cell line generation. A) Scheme of the screening of high-producer cell line. The selected pool with highest expression of reporter gene was divided to mini-pools followed by single-cell cloning of best mini-pools based on the reporter gene expression. For final screening, the cell densities in 6-well plate were normalized and after 2 days, media was collected for the ELISA analysis. B) ELISA assay for measuring 4F3 expression in 6-well plate. C) The small-scale fed-batch culture production analysis of top 12 clonal cell lines. Length of production was 10 days, production supernatants were analyzed by Octet K2.

Figure 5:
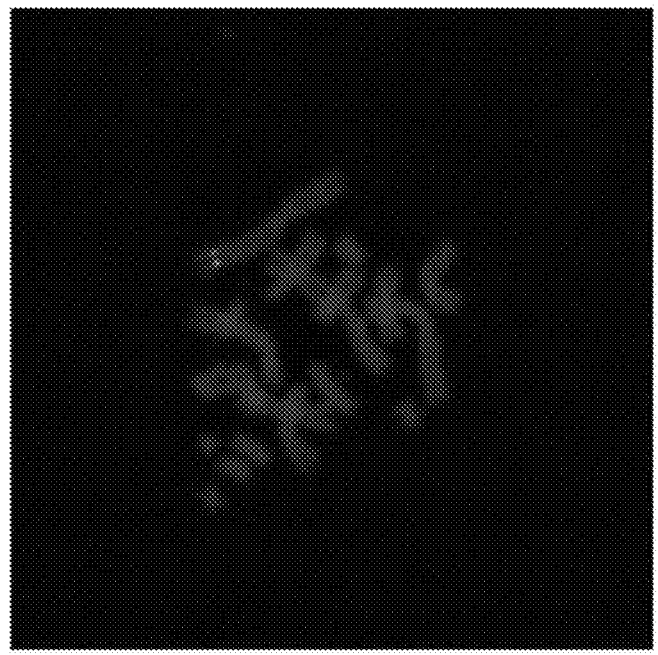

FIG. 5. Characterization of #504C6 landing pad cell line by fluorescence in situ hybridization. Metaphase chromosomes were hybridized with biotin labeled landing pad vector LP2str_4F3_CAR #182, signal was amplified with Tyramide signal amplification kit and detected with HRP-Streptavidin and Alexa Fluor™ 488 Tyramide. Here, the #504C6 cell line was characterized as having a single integration site.

Figure 6:
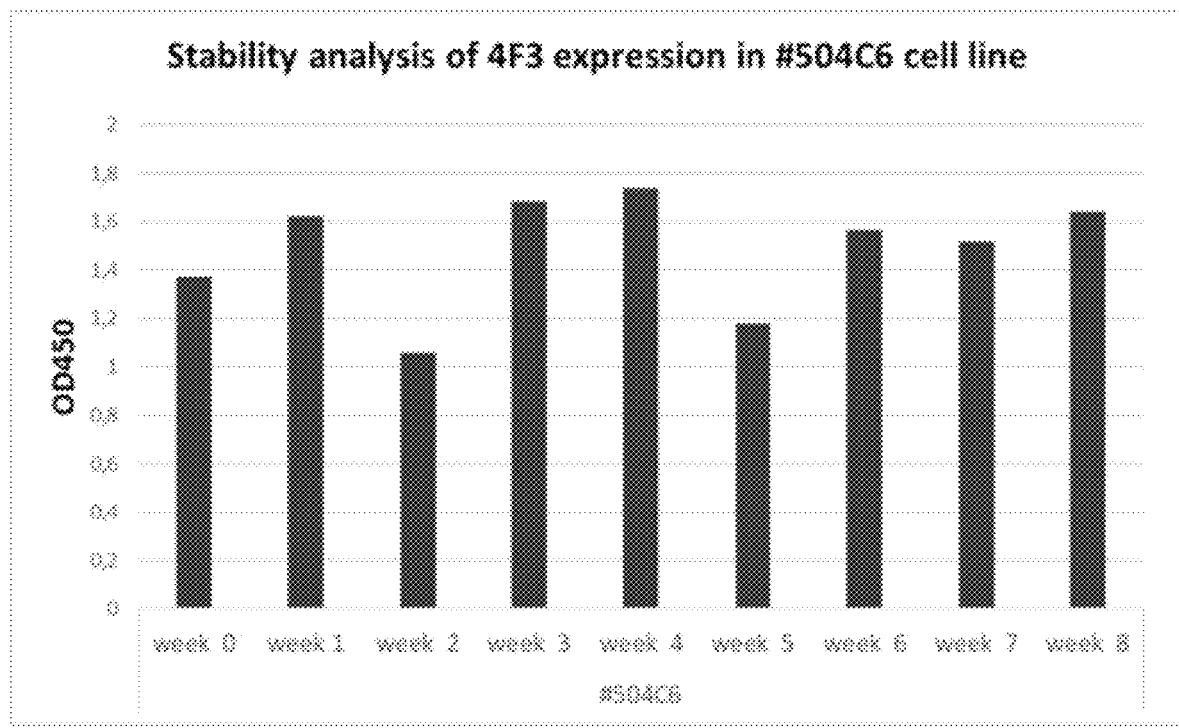

FIG. 6. Stability analysis of 4F3 expression in #504C6 landing pad cell line. For stability analysis, #504C6 cell line was cultivated for 8 weeks. Each week, cells were counted and seeded with density ($5 \times 10^5$ cells/ml) and 2 days later, the samples from cell culture media were collected. 4F3 scFv expression analysis was conducted by ELISA, x-axis presents absorbance at 450 nm.

Figure 7:
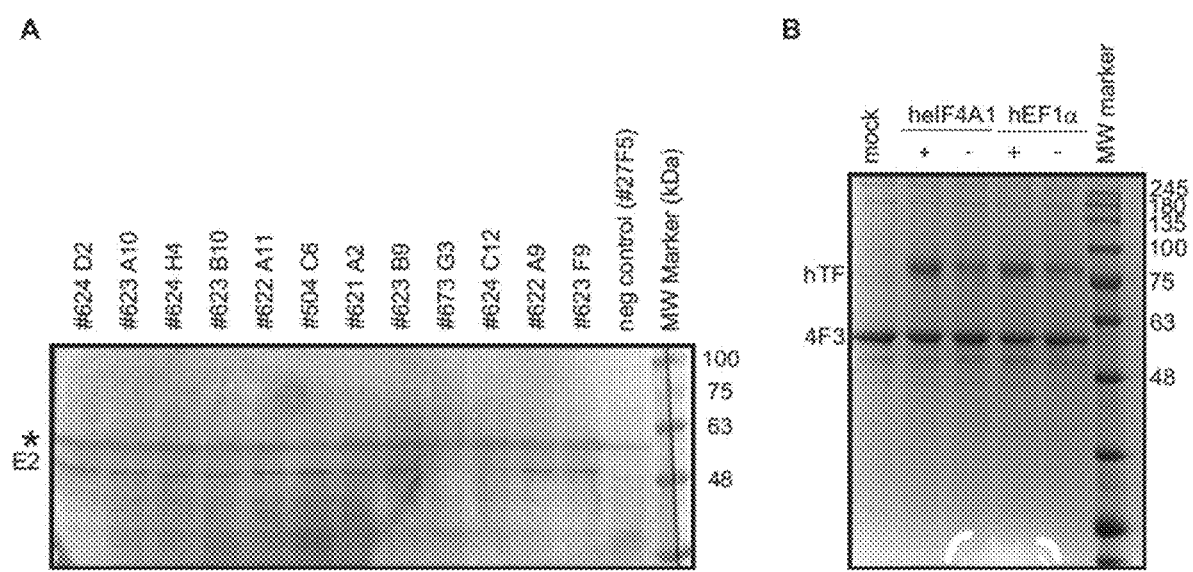

FIG. 7. The presence of BPV1 E2 protein in the landing pad cell lines increases the expression from promoters in the proximity of E2 binding sites. A) Western blot analysis of the expression of BPV1 E2 protein in landing pad cell lines. The mixture of in-house developed antibodies against BPV1 E2 protein (#1E4 and #3E8) was used for detection. E2 marks the BPV1 E2 protein and * marks the unspecific protein recognized by E2 antibody. B) The presence of BPV1 E2 binding sites in the proximity of promoters driving the transcription of recombinant protein (as an example human transferrin, but any preferred protein may be expressed) has positive effect on the expression level of these proteins. Western blot analysis detecting human transferrin expression in BPV1 E2 positive landing pad cell line #504C6 3 days after transfection. Plasmids with (+) or without (−) BPV1 E2 binding sites in front of heIF4A1 and hEF1α promoters driving hTF expression were analyzed. The expression of reporter antibody 4F3 scFv is also detectable, as the secondary antibody recognizing the hTF antibody cross-reacts with human scFV antibody.

Figure 8:
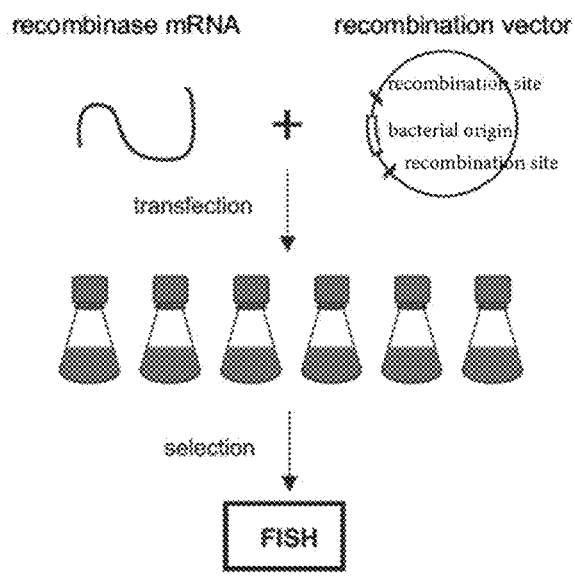

FIG. 8. Optimization of recombination efficiency in landing pad cell lines. A) Scheme for the gene of interest (GOI) cell line development experiment for finding suitable conditions for recombination. CHO cells were transfected with different amounts of plasmid DNA (100 ng, 300 ng or 1000 ng) or recombinase mRNA (1 or 3 ng), followed by selection with antibiotics and recovery of pools. B) Estimation of recombination efficiency by fluorescence in situ hybridization (FISH). At least 100 metaphase cells were examined for each pool to calculate the frequencies of targeted integration, targeted integration with additional random integration of the recombination cassette, or random integration events with up to 2 or more integration sites. Cell pool transfected with 3 μg Cre mRNA and 300 ng pGOI had highest frequency of targeted integration and lowest frequency of random integration and was selected for use in single-cell cloning by limiting dilution.

Figure 9:
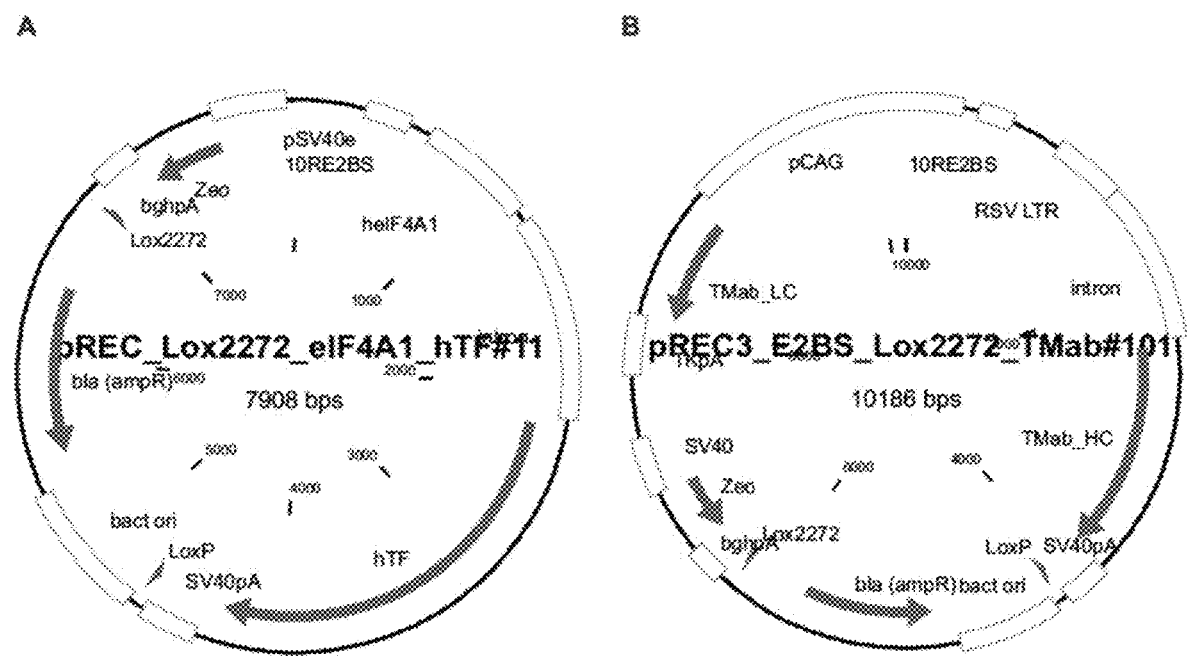

FIG. 9. The schemes of exchange vectors A) single-cassette gene-of-interest expression vectors used for targeted integration. B) double-cassette gene-of-interest expression vector suitable for targeted integration.

Figure 10:
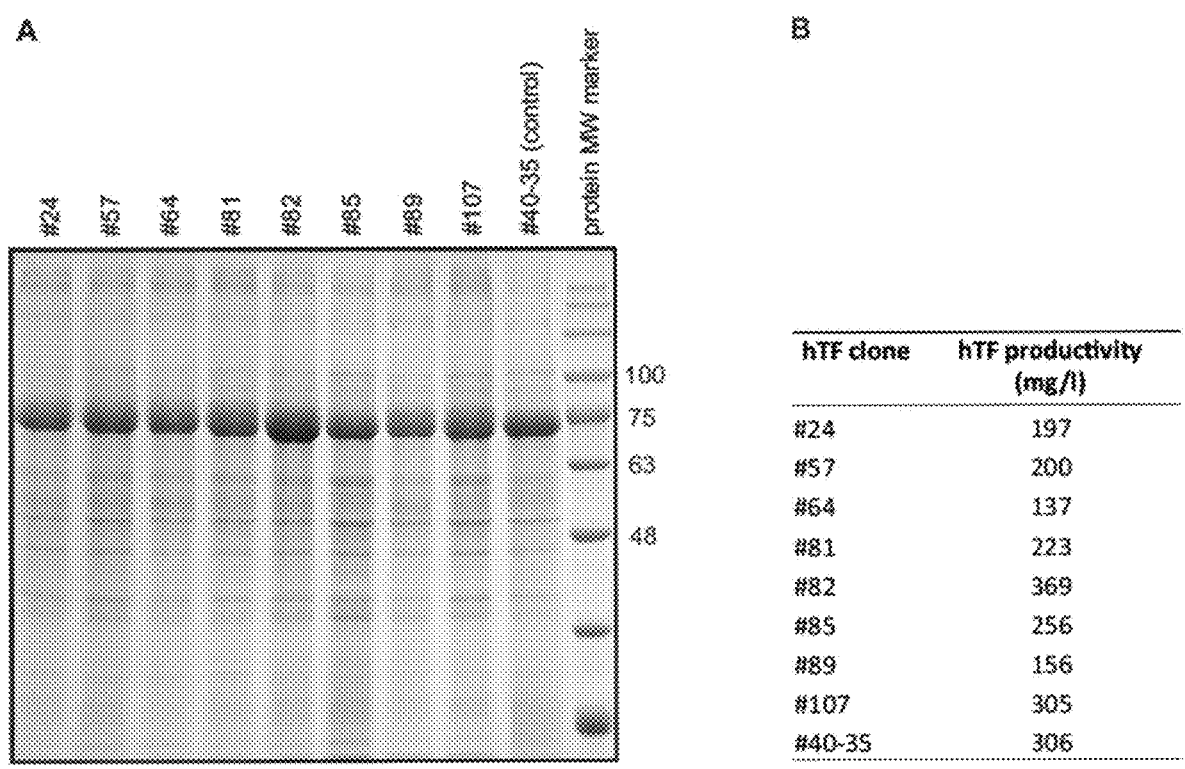

FIG. 10. The production of recombinant protein (e.g. human transferrin) in cell lines generated from #504C6 parental cell line. The clonal cell lines were generated by limiting dilution of the pool with highest frequency of targeted integration, followed by screening of the loss of reporter gene in 96-well format. The cell lines with no expression of the reporter antibody (4F3) were expanded to 24-well, 6-well and then to 125 ml shaker flask, after which the fed-batch production was performed. Supernatants were analyzed by SDS-PAGE (A) and ELISA (B). A) SDS-PAGE analysis of the fed-batch production supernatants collected in the end of production; B) ELISA analysis of the fed-batch production supernatants collected in the end of production. Productivity of human transferrin by these cell lines (mg/l) was calculated.

Figure 11:
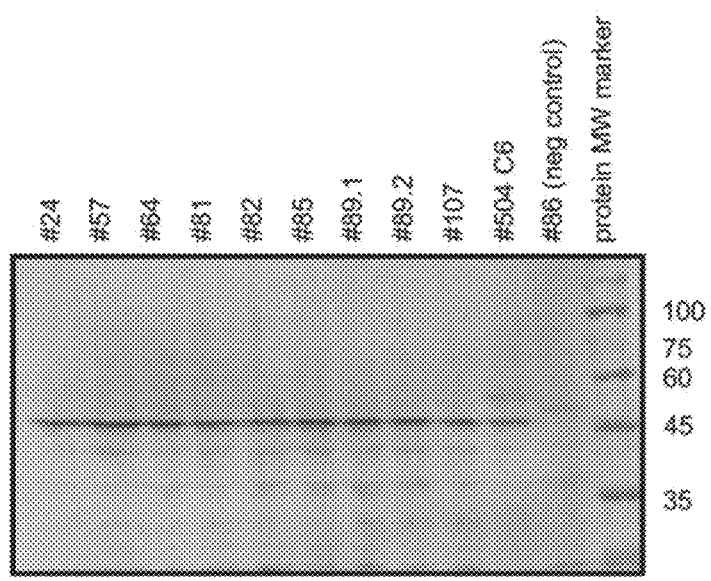

FIG. 11. BPV1 E2 protein is expressed in the human transferrin cell lines generated from #504C6 cell line by RMCE. The expression of BPV1 E2 protein is evaluated by immunoblot. The lysate of ~50 000 cells was separated by SDS-PAGE and transferred to PVDF membrane. For detection, the mixture of in-house developed antibodies against E2 protein (#1E4 and #3E8) were used at concentration 1 μg/ml.

DETAILED DESCRIPTION OF THE INVENTION

Definitions. In this disclosure the following terms are used as defined below:

"A gene of interest" refers to a cDNA encoding a gene product of interest such as a protein of interest or recombinant protein of interest.

"attB" refers to nucleotide sequence
(SEQ ID NO: 9)
GGTTTGTCTGGTCAACCACCGCGGTCTCAGTGGTGTACGGTACAAACC.

"attP" refers to sequence
(SEQ ID NO: 10)
GGCTTGTCGACGACGGCGGTCTCCGTCGTCAGGATCAT.

"BPV1" refers to bovine papillomavirus type I.

"E2" refers to a protein encoded by nucleotides 2594-3837 of BPV subtype 1.

"E2BS" refers to bovine papillomavirus E2 protein binding sites.

"EGFP" refers to Enhanced Green Fluorescent Protein.

"FLuc" refers to Firefly Luciferase.

"FR" refers to Family of Repeats, Epstein Barr virus EBNA1 protein binding site.

"FRT1" refers to recombinase recognition sequence of Flp (SEQ ID NO: 7)
GAAGTTCCTATTCCGAAGTTCCTATTCTCTAGAAAGTATAGGAACTTC "FRT6" refers to modified recombinase recognition sequence of Flp (SEQ ID NO: 8)
GAAGTTCCTATTCCGAAGTTCCTATTCTTCAAAAAGTATAGGAACTTC.

"GLuc" refers to Gaussia luciferase.

"landing pad cell line" refers to a mammalian cell line, that contains the integrated landing pad cassette.

"landing pad" refers to plasmids that contain recognition sequences for site-specific recombinases (suitable recombinases are e. g., BxB1 integrase, Flp or Cre recombinase, but it is to be noted that other recombinases may also be used), expression cassettes of reporter genes (suitable reporter genes are secreted alkaline phosphatase (SEAP), Gaussia luciferase, Firefly luciferase, enhanced green fluorescent protein (EGFP) and/or in-house developed single chain antibody 4F3, but it is to be noted that other reported genes may also be used), and expression cassettes for proteins giving resistance to selection antibiotics. Some but not all "landing pad" vectors contain binding sites for BPV1 E2 protein and/or binding sites for EBV EBNA 1 binding sites.

"Lox2272" refers to 34 nucleotide sequence ATAACTTCGTATAAaGTATcCTATACGAAGTTAT (SEQ ID NO:6) which contains 2 altered residues compared to LoxP sequence.

"LoxP" refers to 34 nucleotide sequence ATAACTTCGTATAATGTATGCTATACGAAGTTAT (SEQ ID NO: 5) found on bacteriophage P1. This is a recombination target site of Cre recombinase of bacteriophage P1;

"pyORI" refers to polyomavirus replication origin.

"RMCE" refers to Recombination Mediated Cassette Exchange, facilitated by site-specific recombinase enzymes such as but not limited to Cre, Flp or BxB1.

"SEAP" refers to Secreted Alkaline Phosphatase

The present disclosure provides a method and constructs for development of stable mammalian cell lines for protein production. The mammalian cells may be CHO cells, but other cell lines such as HEK 293, NS0, Sp2/0 are also possible. The methods and constructs of this disclosure can be used to generate host cells for targeted integration. These host cells or landing pad cells contain expression cassettes of reporter genes, selection markers and recognition sites for site-specific recombinases. Based on the expression of the reporter genes and their stability in time, the best parental cell lines can be selected and thoroughly characterized. After this, cell lines expressing protein-of-interest are generated from suitable parental cell line. For this, site-specific recombinases are used in recombination mediated cassette exchange (RMCE) through recombinase target sites flanking the landing pad cassette and recombination vectors.

It was surprisingly found that E2 protein enables generating stable cell pools with high expression level of reporter genes when landing pad constructs containing BPV1 E2 binding sites are used. Therefore, the present invention provides constructs and methods for co-transfecting BPV1 E2 protein together with the landing pad construct, so that landing pad cell pools with higher expression level of reporter genes can be generated.

According to one aspect of the invention methods and constructs for generation of host cells for targeted integration by using landing pad constructs that contain binding sites for BPV1 E2 protein are provided.

According to one aspect recombination plasmids and mechanisms for targeted integration of the gene-of-interest (GOI) expression vectors to the parental mammalian cell lines are provided.

An advantage of the present invention is reduction of the length of cell line development process compared to classical random integration approach and decrease the cost of the process as less cells/plates need to be screened.

According to one aspect of the invention the bovine papillomavirus type I protein E2, the main transcriptional regulator of BPV1 helps to activate the transcription of promoters in the proximity of E2 binding sites in mammalian cells, including but not limited to CHO-S cells. By regulating transcription through E2 binding sites, BPV1 E2 supports the increase of recombinant protein expression level in E2 positive cell line.

Landing Pad Cell Line Development

Landing pad constructs of this disclosure with all necessary elements are shown in FIG. 2. The landing pad cell line development (schematically characterized in FIG. 1) is performed according to classical random integration approach. The process consists of 5 steps and starts with introduction of linearized landing pad expression cassette into the cell by transfection (e.g., electroporation) and is followed by stable pool selection which starts at 3-5 days after transfection. Antibiotic selection lasts about 1-2 weeks, depending on the antibiotic used, after which the pool is divided by limiting-dilution to generate single cell clones (0.7 to 1 cells/well) or mini-pools (5 to 50 cells/well). In case of landing pad cell line development, thousands of clones/mini-pools need to be screened to achieve clones with high expression of the reporter genes. Based on the expression of reporter genes (e.g. but not limited to SEAP, GLuc, Fluc, EGFP or a scFv antibody), the best producing clones (100-200 clones) were selected in the 96-well format and expanded to 24-wells and then to 6-wells plates. In 6-well, clonal cell lines were counted, normalized based on cell number, and then screened again to reduce the number of clones to be transferred to 125 ml shaker flasks. Research cell banks (RCBs) were generated for best producing landing pad cell lines and the small-scale fed-batch production of reporter genes was performed. Finally, top 4-6 cell lines were characterized by fluorescence in situ hybridization (FISH) to estimate the number of landing pad cassette integration site(s) in the genome of host cells. Monoclonal cell lines that contain only one integration site of the landing pad were considered as suitable cell lines for use for targeted integration of gene-of-interest cassette by recombination-mediated cassette exchange.

Designing of Landing Pad Vectors

To overcome the limitations of random integration, we have engineered landing-pad (LP) expression cassettes that can be integrated to the genome of mammalian cell lines, e.g. but not limited to CHO cells for developing parental cell lines, so called landing pad cell lines. For quantifiable, quick and cost-effective screening, the landing pad constructs encode for one or more detectable fluorescent proteins (e.g. EGFP among others) or secretable proteins (such as antibodies). Once integrated into the cells, landing pad cassette can be replaced with gene-of interest expression cassette by recombination-mediated cassette exchange (RMCE) to generate cell lines producing biologics.

Several versions of the landing pad expression cassettes containing the following elements were engineered:

1. Reporter genes for easy and cost-effective screening of high-producing clones. For protein production in industrial scale, a cell line should have high transcription and translation levels and for evaluation of these processes, both intracellular reporter genes (e.g. but not limited to Firefly luciferase, Fluc; EGFP, Green fluorescent protein) and extracellular reporter genes (e.g. but not limited Gaussia luciferase, Gluc; Secretative alkaline phosphatase, SEAP; monoclonal antibody) can be used. After the synthesis and post-translational modification, recombinant protein has to be secreted to the growth media, so that the purification of the protein would be easier. Therefore, besides transcription and translation, the ability to efficiently secrete large amount of protein(s) is crucial. Thus, secretative reporter genes such as SEAP (although other secretative reporter genes may also be used) describe the secretion machinery of the CHO clone.

2. Promoters for driving gene expression. Most promoters used in the landing pad cassettes are relatively weak viral or eukaryotic promoters, the purpose of which is to avoid downregulation of gene expression caused by high level of intracellular proteins. Relatively high levels of reporter gene expression driven by weak promoter usually means that the construct has integrated into transcriptionally active chromatin region.

3. Binding sites for chromatin anchoring proteins. Many different DNA-viruses replicate as extrachromosomal episomes. For efficient gene expression and replication, the episomal viral genomes situate near transcriptionally active regions of cell genome. The viral genomes are often transferred to these regions by viral protein(s) that bind to their respective binding-sites (BS). Therefore, by inserting virus BS-s into LP (landing pad) DNA, in the presence of viral proteins, the LP should be directed to transcriptionally active region of the chromatin prior to integration. For that, a binding region of BPV1 E2 protein and FR-binding region for Epstein Barr virus EBNA1 protein were inserted into the landing pad constructs. In addition, there is also included Polyomavirus replication origin (PY ori) that facilitates amplification of the integrated cassette in the presence of PY LT protein.

4. Recombination target sites (LoxP, FRT and attB) of site-specific recombinases are flanking the expression cassettes of reporter genes and selection marker. These sites are used for generation of cell lines for production of protein of interest. By inserting compatible recombinase target sites for site-specific recombinases to the gene-of-interest expression construct, it can be specifically inserted into genome of a parental cell line to the same position as landing pad. The targeted integration occurs between two LoxP sites facilitated by Cre recombinase, between FRT sites facilitated by Flp recombinase or between attB and attP sites facilitated by BxB1 recombinase.

5. Resistance gene for antibiotic, e.g., for Hygromycin B is required for selection of cells that contain integrated copy or copies of the landing pad cassette.

Plasmids. Detailed Description Vectors Used in Landing Pad Cell Line Development Landing pad vectors were constructed according to principles described above and the integrity of the elements was assessed by sequencing. Linearized constructs are schematically shown in FIG. 2. All plasmid DNA sequences (SEQ ID NO: 1, 2 and 3) are provided; therefore, the detailed molecular cloning steps are not presented here.

LP2str #132 (FIG. 1A, SEQ ID NO:1) contains two expression cassettes. Herpes simplex virus thymidine kinase promoter (pTK), followed by human elongation factor 1a intron A (NCBI Reference Sequence: NC 000006.12) is responsible for expressing the polypeptide, 887 amino acids in length. This polypeptide, encoded by SEQ ID NO:13, is marked as SEAP-2A-HygroR, consists of three parts:

```
i) Secreted alkaline phosphatase (SEAP) from
human placenta:
(SEQ ID NO: 16)
(MLLLLLLLGLRLQLSLGIIPVEEENPDFWNREAAEALGAAKKLQPAQTA

AKNLIIFLGDGMGVSTVTAARILKGQKKDKLGPEIPLAMDRFPYVALSKT

YNVDKHVPDSGATATAYLCGVKGNFQTIGLSAAARFNQCNTTRGNEVISV

MNRAKKAGKSVGVVTTTRVQHASPAGTYAHTVNRNWYSDADVPASARQEG

CQDIATQLISNMDIDVILGGGRKYMFRMGTPDPEYPDDYSQGGTRLDGKN

LVQEWLAKRQGARYVWNRTELMQASLDPSVTELMGLFEPGDMKYEIHRDS

TLDPSLMEMTEAALRLLSRNPRGFFLFVEGGRIDHGHHESRAYRALTETI

MFDDAIERAGQLTSEEDTLSLVTADHSHVFSFGGYPLRGSSIFGLAPGKA

RDRKAYTVLLYGNGPGYVLKDGARPDVTESESGSPEYRQQSAVPLDEETH

AGEDVAVFARGPQAHLVHGVQEQTFIAHVMAFAACLEPYTACDLAPPAGT

TDAAHPGYSRVGAAGRFEQT)
followed by ii) 2A peptide from foot-and-mouth disease virus
(SEQ ID NO: 17):
(APVKQTLNFDLLKLAGDVESNPGP)
followed by iii) hygromycin B phosphotransferase
(SEQ ID NO: 18)
(KKPELTATSVEKFLIEKFDSVSDLMQLSEGEESRAFSFDVGGRGYVLRV

NSCADGFYKDRYVYRHFASAALPIPEVLDIGEFSESLTYCISRRAQGVTL

QDLPETELPAVLQPVAEAMDAIAAADLSQTSGFGPFGPQGIGQYTTWRDF

ICAIADPHVYHWQTVMDDTVSASVAQALDELMLWAEDCPEVRHLVHADFG

SNNVLTDNGRITAVIDWSEAMFGDSQYEVANIFFWRPWLACMEQQTRYFE
```

-continued

RRHPELAGSPRLRAYMLRIGLDQLYQSLVDGNFDDAAWAQGRCDAIVRSG

AGTVGRTQIARRSAAVWTDGCVEVLADSGNRRPSTRPDREMGEAN).

This polypeptide is processed co-translationally, yielding two final products—detectable SEAP and hygromycin B phosphotransferase that gives resistance to hygromycin B.

The second expression cassette contains the SV40 enhancer and early promoter (pSV40e), in-house developed synthetic intron, expression cassette of a second polypeptide, GLuc-2A-EGFP-2A-Fluc, and herpes simplex virus 1 thymidine kinase polyA signal. GLuc-2A-EGFP-2A-Fluc polypeptide, encoded by SEQ ID NO:12, consisting of 1024 amino acids has the following parts:

i) Gaussia luciferase
(SEQ ID NO: 19)
(MGVKVLFALICIAVAEAKPTENNEDFNIVAVASNFATTDLDADRGKLPG

KKLPLEVLKEMEANARKAGCTRGCLICLSHIKCTPKMKKFIPGRCHTYEG

DKESAQGGIGEAIVDIPEIPGFKDLEPMEQFIAQVDLCVDCTTGCLKGLA

NVQCSDLLKKWLPQRCATFASKIQGQVDKIKGAGGD)
followed by ii) 2A peptide from foot-and-mouth diseasevirus
(SEQ ID NO: 17)
(APVKQTLNFDLLKLAGDVESNPGP)
followed by iii) Enhanced green fluorescent protein
(SEQ ID NO: 20)
(FEMVSKGEELFTGVVPILVELDGDVNGERFSVSGEGEGDATYGKLTLKF

ICTTGKLPVPWPTLVTTLTYGVQCFSRYPDHMKQHDFFKSAMPEGYVQER

TIFFKDDGNYKTRAEVKFEGDTLVNRIELKGIDFKEDGNILGHKLEYNYN

SHNVYIMADKQKNGIKVNFKIRHNIEDGSVQLADHYQQNTPIGDGPVLLP

DNHYLSTQSALSKDPNEKRDHMVLLEFVTAAGITLGMDELYK)
(SEQ ID NO: 15)
followed by iv) 2A peptide from foot-and-mouth disease virus
(SEQ ID NO: 16)
(APVKQTLNFDLLKLAGDVESNPGP)
followed by v) Firefly luciferase
(SEQ ID NO: 21)
MEDAKNIKKGPAPFYPLEDGTAGEQLHKAMKRYALVPGTIAFTDAHIEVD

ITYAEYFEMSVRLAEAMKRYGLNTNHRIVVCSENSLQFFMPVLGALFIGV

AVAPANDIYNERELLNSMGISQPTVVFVSKKGLQKILNVQKKLPIIQKII

IMDSKTDYQGFQSMYTFVTSHLPPGFNEYDFVPESFDRDKTIALIMNSSG

STGLPKGVALPHRTACVRFSHARDPIFGNQIIPDTAILSVVPFHHGFGMF

TTLGYLICGFRVVLMYRFEEELFLRSLQDYKIQSALLVPTLFGFFAKSTL

IDKYDLSNLHEIASGGAPLSKEVGEAVAKRFHLPGIRQGYGLTETTSAIL

ITPEGDDKPGAVGKVVPFFEAKVVDLDTGKTLGVNQRGELCVRGPMIMSG

YVNNPEATNALIDKDGWLHSGDIAYWDEDEHFFIVDRLKSLIKYKGYQVA

PAELESILLQHPNIFDAGVAGLPDDDAGELPAAVVVLEHGKTMTEKEIVD

YVASQVTTAKKLRGGVVFVDEVPKGLTGKLDARKIREILIKAKKGGKIA

V).

This polypeptide is also processed co-translationally, yielding three final products—Gaussia luciferase, EGFP and Firefly luciferase, all of which are reporter proteins that can be used for evaluating the productivity of the cell clones.

Between two expression cassettes are located:
i) The binding sites of BPV1 E2 protein (BPV E2BSs; SEQ ID NO: 22)
ii) polyomavirus core origin (PyVOri SEQ ID NO:23)
iii) The binding sites for EBNA-1 protein from Epstein-Barr virus known as Family of repeats (FR; SEQ ID NO:24)

LP2str #132 contains two types of recombinase target sites—LoxP and attB, recognized by Cre recombinase from bacteriophage P1 and BxB1 integrase from bacteriophage. When cells containing the LP2str #132 are used for generation of cell lines producing protein-of-interest, the exchange vectors should contain either two LoxP sites or two attP sites.

In LP2str_CAR_4F3 #182 and LP2str_4F3_wo BS #3, the expression cassette of Gluc-2A-EGFP-2A-Fluc is replaced with cassette encoding for an in-house developed antibody (4F3 scFv) that recognizes the Ebolavirus Zaire glycoprotein. The expression of this reporter gene is driven by Rous sarcoma virus long terminal repeat promoter (RSV LTR). A small intron (SEQ ID NO:25), located upstream of the ORF, and SV40 polyA signal are also included in the cassette.

LP2str_CAR_4F3 #182 contains incompatible or "hetero-specific" recombinase target sites. At one side of the expression cassette, there is wild-type recognition site of Cre recombinase, known as LoxP site. A mutated target site, Lox2272 is flanking the expression cassettes from another side. Recombination occurs between two LoxP sites or between two Lox2272 sites, but not between the incompatible LoxP and Lox2272 sites. The introduction of different recombinase target sites to the plasmids helps to avoid the intramolecular recombination events. In addition, this landing pad cassette includes another set of incompatible recombinase target sites, FRT1 and FRT6 that are used by *Saccharomyces cerevisiae* site specific recombinase flippase (Flp). Recombination occurs between two FRT1 sites or between two FRT6 sites but not between the incompatible sites. For GOI-cell line development, the exchange vectors should also have two incompatible recombinase target sites, either Lox2272 and LoxP site, or FRT1 and FRT6 sites. At the same time, the Cre or Flp recombinase should be expressed.

pQMCF-7-BPVE2 #32 is the expression vector for BPV1 E2 protein. Expression cassette contains herpes simplex virus thymidine kinase promoter followed by human elongation factor 1α intron A, the coding region for BPV1 E2 protein and SV40 polyA sequence. SV40 enhancer and early promoter (pSV40e) drives expression of aminoglycoside phosphotransferase from Tn5 that gives resistance to aminoglycoside antibiotics, such as kanamycin and geneticin, used for selecting bacterial and mammalian cells, respectively. The purpose of using BPV1 E2 protein was to bind it to E2BS present in landing pad expression cassette in order to facilitate the loading of landing pad sequences to transcriptionally active chromatin region.

Designing of Gene-of-Interest Expression Vectors

Depending on the type of protein to be produced, vectors containing either one (e.g. SEQ ID NO:14) or two expression cassettes (SEQ ID NO:15) can be used. It is to be understood that other vectors may also be developed for this purpose. For driving the expression of gene of interest, human eIF4A1, human hEF1α, CAG promoter and RSV LTR are introduced to the cassettes. It is to be understand that other weak promoters may also be used. Also replacing these weak promoters with a stronger one, e.g. with CMV promoter or even with a transcriptionally active cellular promotor may be used.

Recombination vectors contain the expression cassette of another selection marker compared to landing pad cell lines, e.g. *Streptoalloteichus hindustanus* Sh ble gene, conferring resistance to zeocin or puromycin N-acetyltransferase, conferring resistance to puromycin. The expression of resistance gene is driven by SV40 early enhancer and promoter or HSV TK promoter and the bgh polyA signal is used in both cases.

For RMCE, recombinase target sites must be introduced to the recombination vectors. In order to use cell lines containing the LP2str #132 landing pad for protein-of-interest cell line development, recombination plasmids containing two wild-type LoxP sites or two attP sites should be used. For using cell lines having the LP2str_CAR_4F3 #182, recombination plasmids with incompatible Lox2272 and LoxP or recombination plasmids with incompatible FRT1 and FRT6 sites are use in RMCE to develop new cell lines.

Cell Culture and Transfections

CHO cells were cultivated in medium containing 1:1 mixture of CD CHO (Thermo Fisher Scientific, Cat No. 10743-029) and 293 SFMII (Thermo Fisher Scientific, Cat No. 11686-029). Medium is supplemented with 6 mM GlutaMax (Thermo Fisher Scientific, Cat No. 35050-038) and 10 ml/l HT Supplement (Thermo Fisher Scientific, Cat No. 41065-12). For selecting landing pad cell pools, medium is supplemented with 400 µg/ml Hygromycin B (Thermo Fisher Scientific, Cat No. 10687-010). For selecting cells expressing protein of interest, medium is supplemented with 100 µg/ml zeocin (Thermo Fisher Scientific, Cat. No. R250). Cells were grown at 37° C. in a humidified 8% $CO_2$ environment. For cultivating cells in 24-well, 6-well plates or 125 ml shaker flasks, orbital shaking incubator at 110 rpm (orbital diameter 25 mm) is used.

Cells were transfected by electroporation with Bio-Rad Gene Pulser II that was supplied with a capacitance extender (Bio-Rad Laboratories). For transfecting plasmid DNA or co-transfecting mRNA and plasmid DNA, capacitance and voltage settings were at 975 µF and 220 V. Cre (Cat. No. 30-101-113) and Flp mRNA (Cat. No. 130-106769) were obtained from Miltenyi Biotec.

Western Blot Analysis and Coomassie Blue Staining

Western blot analysis is performed to evaluate the expression of intracellular BPV1 E2 protein or the secreted human transferrin present in the cell culture media or fed-batch production media. For lysis, cells were collected by centrifugation, suspended in phosphate buffered saline, lysed in equal volume of Laemmli buffer containing DTT and heated at 100° C. for 5 minutes. The cases when DTT is not added, will be marked. Proteins were separated by SDS-polyacrylamide gel electrophoresis and transferred by a semidry blotting method to a polyvinylidene difluoride (PVDF) membrane (Millipore Corp.). For detecting BPV1 E2, membranes were incubated with in-house developed antibodies against E2 protein (1:1 mixture of #1E4 and #3E8, concentration 1 µg/ml). For detecting hTF, membranes were incubated with antibody against human transferrin (Abcam, Cat. No. 82411, concentration 1:8000). As secondary antibodies, goat anti-mouse IgG or goat anti-rabbit IgG, conjugated with HRP were. Detection was performed using TMB Solution III (Biopanda Diagnostics, Cat. No. TMB-P-001) following the manufacturer's recommendations.

SEAP and GLuc Measurement

For evaluating SEAP and GLuc expression, Secrete-Pair Dual Luminescence Assay Kit (GeneCopoeia, Cat. No. LF032) was used according to manufacturer's suggestions.

ELISA

To evaluate the expression of reporter gene 4F3 scFv by ELISA, in-house produced recombinant Zaire Ebolavirus glycoprotein (1 µg/ml) diluted in PBS was coated onto 96-well MaxiSorp NUNC-immunoplates and incubated overnight at 4° C. Plates were washed with 0.05% Tween20 (PBS-Tw) in PBS and blocked for 1 hour with 2% BSA in PBS-Tw. Dilutions from the cell culture media was prepared and incubated for one hour at room temperature on the shaker. Typically, growth media collected from the 96-well plate is diluted 1:2 to 1:10 and growth media collected from 6-well plate is diluted 1:1000. Horseradish peroxidase (HRP)-conjugated goat anti-human IgG (LabAS), diluted in 1% BSA in PBS-Tw, was used as a secondary antibody for 45 min. After washing, the reaction was developed with the TMB solution VIII (2 in 1) (Biopanda Diagnostics, Cat. No. TMB-P-003) for 10 min and stopped with 0.5 M H2504. The absorbance at 450 nm was measured spectrophotometrically using the ELISA plate reader. For evaluating the concentration of 4F3 scFv in growth media, 2-fold serial dilutions of in-house purified 4F3 scFv antibody were added as standards.

For evaluating the expression level of hTF and calculating the productivity of hTF cell lines, the Elisa kit from Abcam (Cat. No. ab187391) was used according to manufacturer's protocol.

Fed-Batch Production

For fed-batch production analysis, cells were seeded at $4 \times 10^6$ cells/ml in 25-30 ml (in 125 shaker flasks) and the incubation temperature was shifted from 37° C. to 30° C. Cells were fed on days 0, 2, 4, 6 and 8 with 6% of proprietary feed and the production media was collected at day 10. For production of recombinant proteins, Feed B (Thermo Fisher Scientific, Cat. No. A1024001) supplemented with 6 mM GlutaMax (*Thermo Fisher Scientific*, Cat No. 35050-038) was used. For production of antibodies, the 1:1 mixture of Feed A (Thermo Fisher Scientific, Cat. No. A1023401) and Feed B (Thermo Fisher Scientific, Cat. No. A1024001), supplemented with 6 mM GlutaMax (*Thermo Fisher Scientific*, Cat No. 35050-038) was used.

Example 1

BPV1 E2 Protein Increases the Expression Level of Recombinant Proteins in Mammalian Cells To test whether BPV1 E2 protein affects the recombinant protein expression in mammalian cells and could be used in stable cell line development, the landing pad vectors with (SEQ ID NO:2) and without BPV1 E2 binding sites (SEQ ID NO:3) were generated. Expect in the presence or absence of E2 binding sites, both vectors are similar and contain the expression cassettes of two reporter genes—one for in-house developed single chain antibody (4F3 scFv, encoded by SEQ ID NO: 11) and the other for secreted alkaline phosphatase (SEAP). SEAP-2A-Hygromycin is transcribed as a single transcript and cleaved during translation by 2A peptide to SEAP and hygromycin phosphotransferase that gives resistance to hygromycin B. Compared to SEAP-2A-Hygromycin, 4F3 scFv was expressed from opposite strand.

Before transfection, LP2str 4F3 CAR #182 (SEQ ID NO:2) and LP2str_4F3_wo BS #3 (SEQ ID NO:3) were linearized with VspI restrictase to excise unnecessary bacterial origin of replication and prokaryotic selection marker region. The gel-purified linearized landing pad cassettes and the circular expression vector of bovine papillomavirus E2 protein (SEQ ID NO:4) were co-transfected to CHO-S clone #QE3 cells by electroporation.

In each transfection, 150 ng of landing pad vector (either SEQ ID NO:8 or SEQ ID NO:9) was used, whereas the amount of transfected BPV1 E2 vector was changed in the experiment. The scheme of the transfection is the following:
1) mock
2) 150 ng LP2str_4F3_CAR #182/VspI
3) 150 ng LP2str_4F3_CAR #182/VspI+5 ng pQMCF-7-BPV1E2 #32
4) 150 ng LP2str_4F3_CAR #182/VspI+50 ng pQMCF-7-BPV1E2 #32
5) 150 ng LP2str_4F3_CAR #182/VspI+250 ng pQMCF-7-BPV1E2 #32
6) 150 ng LP2str_4F3_w/o BS #3/VspI+5 ng pQMCF-7-BPV1E2 #32
7) 150 ng LP2str_4F3_w/o BS #3/VspI+50 ng pQMCF-7-BPV1E2 #32
8) 150 ng LP2str_4F3_w/o BS #3/VspI+250 ng pQMCF-7-BPV1E2 #32

Two days after transfection, the 400 µg/ml Hygromycin B was added to the media and the cells were selected in the presence of antibiotic for one week to generate stable cell pools containing integrated landing pad cassettes. The probe number 1 (mock) did not survive the selection as it was not transfected with landing pad cassette and therefore, it does not contain the hygromycin phosphotransferase gene. 7 days after the addition of hygromycin B, the cells of selected pools were counted, seeded with equal density and the probes for analyzing the expression of reporter genes were collected 2 days after the normalization. The expression of 4F3 scFv was tested by enzyme-linked immunosorbent assay (ELISA) and the expression of SEAP was measured by Secrete-Pair Dual Luminescence Assay Kit (GeneCopoeia) according to manufacturer's recommendations. FIG. 3 summarizes the results of both assays. Results are presented as relatives to probe 2, transfected only with the landing pad expression cassette.

As seen in FIG. 3, the presence of E2 binding sites in the landing pad vector positively affects the expression of 4F3 scFv and SEAP reporter genes. Furthermore, when E2 binding sites are present, the expression of both reporter genes increases together with the amount of transfected BPV1 E2 construct. The expression level of SEAP and 4F3 scFv from LP2str_4F3_CAR #182 is similar to the control (probe 2) if only 5 ng of pQMCF-7-BPV1 E2 was transfected. However, the expression of 4F3 scFv is ~3.5 fold and the expression of SEAP is ~2.5 fold higher than control when 250 ng of pQMCF-7-BPV1 E2 was transfected. When E2 binding sites are not present in the landing pad cassette, the concentration of the reporter proteins in the media is not dependent on the amount of transfected BPV1 E2 vector.

Taken together, the expression of BPV1 E2 protein increases the reporter gene expression when E2 binding sites are introduced to the landing pad vectors. Thus, BPV 1 E2 protein could be used in stable mammalian cell line development to increase the expression of recombinant protein, such as antibodies or other secreted proteins.

Example 2

The Generation of #504C6 Landing Pad Cell Line

FIG. 4A provides an example of landing pad cell line generation. The selected pool, originating from transfection number 5 (FIG. 3, marked with star) had the highest expression of both reporter genes and therefore, it was chosen for sub-cloning to mini-pools. Cloning to mini-pools rather than single-cell clones was preferred as this approach helps to increase the number of clonal cell lines to be analysed.

For mini-pool cloning, the cell pool was counted, diluted to density of 250 cells/ml and seeded to 90 96-well plates (100 µl per well). 5 days later, the ELISA screen for testing the expression of 4F3 scFv antibody was performed, after which the top 20 mini-pools were divided again ($2^{nd}$ round mini-pool cloning). This time, each well, containing ~400-800 cells was divided between two 96-well plates and cultivated for 2 weeks, after which the screening to test the expression of 4F3 scFv was performed to select top 8 mini-pools (#51, 62, 66, 67, 60, 31, 50 and 15). These highest producers were cultivated to larger volume and divided by limiting dilution (0.5 cells/well) to achieve clonal cell lines. After the clones achieved desired cell density, the expression analysis of 4F3 scFv was performed to select top 120 cell lines that were expanded to 6-well plates.

In 6-well plates, cells were counted and diluted to similar density ($5 \times 10^5$ cells/ml). After 3 days, the samples from growth media were collected for evaluating 4F3 scFv expression by ELISA. In 6-well, 120 clonal cell lines were analysed and based on the ELISA results, the top 10% of cell lines (FIG. 4B) were transferred to 125 ml shaker flasks and cultivated to desired volume and density for research cell bank generation. The calculated concentration of 4F3 scFv in culture media of selected 12 cell lines ranged from ~30-60 mg/l in growth conditions. Next, top 12 cell lines were transferred to 30° C. to test the productivity of reporter antibody in small-scale fed-batch production. Throughout production, 6% of the mixture of Feed A and B was added to the cells on days 0, 2, 4, 6 and 8. At day 10, the production media was collected, clarified by centrifugation (1000×g, 30 min, 4° C.) after which the concentration of secreted 4F3 was analysed by Octet K2 (FIG. 4C). The results of Octet K2 show that the productivities of the cell lines ranged from ~800 to 1500 mg/l in all cell lines. All clones from mini-pool #62 produced more than 1200 mg/l of 4F3 scFv, whereas the clones from mini-pools #50 and #67 produced 850 mg/l and 800 mg/ of 4F3 scFv, respectively.

Thus, by co-transfecting CHO cells with the landing pad vector (SEQ ID NO:2) and BPV1 E2 expression cassette (SEQ ID NO:4), it is possible to generate the parental cell lines with high expression of reporter antibody.

Example 3

504C6 Landing Pad Cell Line has One Integration Site in the CHO Genome

Great parental cell lines have integrated the landing pad expression cassette into the active site of the genome. Random integration approach, used in the landing pad cell line development, could generate cell lines with either single or several integration sites of the cassette. Therefore, when only one integration site of the transgene is acceptable for the parental cell line, more than one clonal cell line should be developed to the RCB stage.

To investigate the monoclonality of the cell lines as well as the number of integration sites of LP2str_4F3_CAR #182 (SEQ ID NO:2) in the CHO cell genome by fluorescence in situ hybridization (FISH), metaphase chromosomes from three cell lines (#621 A2, #622 A11 and #504 C6) were prepared and hybridized with biotin labeled LP2str_4F3_CAR #182. Signal was amplified with Tyramide signal amplification kit and detected with HRP-Streptavidin and Alexa Fluor™ 488 Tyramide. According to the results, all three cell lines were monoclonal, meaning that all metaphase cells have a similar integration pattern. Two of the cell lines (#621 A2 and #622 A11), originating from the mini-pool #62, had two integration sites of the landing pad cassette and will therefore not used in the later stages of the development. The cell line #504 C6, originating from mini-pool #50, was selected for further studies because this cell line has a single integration site of the LP2str_4F3_CAR #182, located at telomeric region of a large chromosome. The results of FISH analysis of #504 C6 cell line are presented on FIG. 5.

Targeted locus amplification (TLA) analysis (outsourced from Cergentis B.V.) confirmed the FISH analysis, showing that there is only one integration site of the LP2str_4F3_CAR #182 located in the scaffold 15 (data not shown).

Example 4

The Expression of 4F3 scFv Antibody is Stable for at Least 8 Weeks in #504 C6 Landing Pad Cell Line A long generation time of mammalian cells is needed to achieve the desired growth volume and cell density in bioreactors before the production of biologics could be started. Therefore, one important requirement for the production cell line is the stability of recombinant protein expression for at least one month. For testing the stability of the reporter gene expression in our landing pad cell line #504 C6, it was cultivated for 8 weeks. Throughout the experiment, cells were monitored and diluted every 2-3 days. Each week, cells were diluted to the same density ($5 \times 10^5$ cells/ml in 20 ml) and after 2 days, the sample of the growth media was collected. After 8 weeks, ELISA analysis was performed to compare the amount of 4F3 scFv antibody in growth media. The results, presented in FIG. 6, demonstrate that #504 C6 cell line maintains the stable expression of 4F3 scFv for at least 8 weeks. There are small reductions in the expression level of 4F3 scFv on weeks 2 and 5, probably caused by the difference in the counting of cells.

Example 5

BPV1 E2 Expression Vector Has Integrated to the Genome of the Landing Pad Cells Enabling the Constant Expression of BPV1 E2 Protein For generation of landing pad cell line #504 C6, the unmodified CHO-S cell line was co-transfected with LP2str_4F3_CAR #182 and pQMCF-7-BPV1E2 #32. The landing pad vector has the expression cassette for hygromycin phosphotransferase, favoring the integration of the cassette in the presence of hygromycin B selection. pQMCF-7-BPV1E2 #32 contains the expression cassette for aminoglycoside phosphotransferase that makes cells resistant to neomycin and geneticin, however, these antibiotics were not used to select the integration of BPV1 E2 expression cassette. To find out whether the fragments of pQMCF-7-BPV1E2 #32 could also have integrated to the #504 C6 cell line, the TLA analysis of this vector was done together with LP2str_4F3_CAR #182 analysis. To our surprise, #504 C6 cell line contained the whole pQMCF-7-BPV1E2 #32.

Although pQMCF-7-BPV1E2 #32 was integrated to the #504 C6 landing pad cells it does not necessarily mean that the BPV1 E2 protein itself is expressed at the detectable level. Therefore, western blot analysis for evaluating BPV1 E2 expression was performed in 12 parental cell lines, characterized in FIG. 4C. A control cell line #21F5, generated by random integration of only LP2str_4F3_CAR #182 but without pQMCF7-BPV1E2 #32 was also included in the experiment as a negative control. As seen on the western blot, presented in FIG. 7A, all landing pad cell lines, except the negative control #21F5 express BPV1 E2.

Example 6

BPV1 E2 Protein Upregulates the Transient Expression of Recombinant Proteins Via E2 Binding Sites Introduced to the Plasmids BPV1 E2 protein is a transcription factor that regulates the transcription via its binding sites in the viral genome. To study whether the BPV1 E2 protein, encoded from the integrated expression cassette in CHO cells, could help to increase the expression level of an ectopically expressed recombinant protein via E2 binding sites introduced to the plasmid DNA, a transient expression experiment was performed in #504 C6 landing pad cell lines. For this, 4 different constructs expressing a recombinant protein such as human transferrin were prepared. In two of the plasmids, hTF transcription is driven by the heIF4A1 promoter and in another two plasmids by hEF1α promoter. In both cases, one of the cassette contained the E2 binding sites upstream of the promoter (marked with +), whereas another construct lacks E2 binding sites (marked with −). For evaluating the effect of the E2BSs on the hTF protein expression, the plasmid DNAs and a mock control (only carrier DNA) were transfected by electroporation to #504 C6 cells. 3 days later, supernatant samples were collected and the expression of hTF was analysed by western blot. As seen in FIG. 7B, two proteins have been visualized. The immunoblot analysis demonstrates that the expression of hTF (upper band) is highest from plasmids containing the E2 binding sites. In case of both promoters (heIF4A1 and hEF1), the expression of hTF was lower in the absence of BPV1 E2 binding sites. The reporter antibody 4F3 scFv (lower band), detectable due to the cross-reactivity of the secondary antibody towards scFv, is expressed at similar level in all pools.

Taken together, the presence of BPV1 E2 binding sites in the proximity of promoters driving the transcription of a recombinant protein (such as human transferrin) has a positive effect on the expression level of these proteins in BPV1 E2 positive cell line such as #504 C6.

Example 7

Optimization of the Conditions for Recombination-Mediated Cassette Exchange Required for the Efficient Development of Cell Lines Producing Protein of Interest The IcoCell parental cell lines such as #504 C6 contain the integrated landing pad cassette in the active site of the genome which facilitates the high expression of the reporter genes. In addition, the recognition sites of several site-specific recombinases were introduced to ends of the landing pad cassette so that these sites could facilitate the recombination mediated cassette exchange to replace the landing pad construct with the expression cassettes of monoclonal antibodies or other recombinant proteins. Since #504 C6 landing pad cell line maintains the stable expression of 4F3 scFv for at least 8 weeks (FIG. 6), the cell lines generated via targeted integration through RMCE should have the similar stability properties. The productivity of 4F3 scFv antibody in fed-batch conditions was ~850 mg/l (FIG. 4C) and it is expected that the cell lines generated from #504 C6 by targeted integration produce the recombinant proteins in a similar manner.

504 C6 landing pad cell line consists the LP2str_4F3_CAR #182 (SEQ ID NO:2) which contains the recognition sequences for different site-specific recombinases (Cre, Flp and BxB1). The site-specific recombinase of bacteriophage P1, the Cre protein, recognizes 34 bp DNA sequence known as LoxP site (SEQ ID NO: 5), mutated sites such as Lox2272 (SEQ ID: NO6) and others. Compared to LoxP site, Lox2272 contains two mutated residues in the 8 bp spacer sequence and preferably, site-specific recombination occurs either between LoxP or Lox2272 sites. In respect to each other, the "heterospecific" LoxP and Lox2272 sites are "incompatible", meaning that the recombination between these two sites does not take place or occurs at a very low frequency.

LoxP and Lox2272 sites are also included in exchange vectors (SEQ ID NO:7 and SEQ ID NO:8) and for targeted integration, the landing pad cells (e.g., to #504 C6 cells) should be co-transfected with exchange vectors and with either the plasmid DNA or mRNA encoding the Cre recombinase. In respect to recombination efficiency, each genomic locus is different and therefore, optimization of transfection e.g., the amount of plasmid DNA and Cre mRNA is crucial for each parental cell line.

To optimize the recombination process in #504 C6 parental cell line and find suitable conditions for protein of interest cell line development, these cells were co-transfected with pREC-Lox2272-E2BS-heIF4A1-hTF-SV40eP-Zeo #11 plasmid and Cre recombinase mRNA (Miltenyi Biotec GmbH). Scheme of the optimization experiment is presented in FIG. 8A.

As seen in FIG. 8A, either 1 or 3 µg of Cre mRNA and 100 ng, 300 ng or 1000 ng of the exchange vector was used in each transfection. For increasing transfection efficiency 50 µg of in-house purified carrier DNA from CHO cells was added to each transfection. Mock control, transfected with carrier DNA was included to the experiment to assess the the length of zeocin selection. For each transfection, 6×10⁶ cells (in 250 µl of the growth media) were mixed with appropriate amount of carrier, plasmid DNA and Cre mRNA in 4-mm electroporation cuvette and transfected by electroporation using BioRad Gene Pulser II, supplied with a capacitance extender (Bio-Rad Laboratories) (settings 230 V; 975 µF). After transfection, cells were collected by centrifugation (300×g 5 min), diluted to required cell density (10⁶ cells/ml) and cultivated for 48 hours, after which fresh media was added to the cells. 72 hours after transfection, 100 µg/ml zeocin was added to select the cells containing the exchange vector. After 2 weeks, selection was over and the efficiencies of targeted and random integration of selected pools were assessed by FISH analysis.

For FISH, the plasmid DNA containing unique elements of pREC-Lox2272-E2BS-heIF4A1-hTF-SV40eP-Zeo #11 was constructed, labeled with biotin and used for hybridization of metaphase chromosomes of cell pools selected with zeocin. Signal was amplified with Tyramide signal amplification kit and detected with HRP-Streptavidin and Alexa Fluor™ 488 Tyramide, At least 100 metaphase cells were examined for each pool to calculate the frequencies of targeted integration, targeted integration with additional random integration of the recombination cassette, or random integration events with up to 2 or more integration sites. The results of FISH, summarized in FIG. 8B, demonstrate that the recombination efficiency is the best (42%) in cell pool no 5 which was transfected with 3 µg of Cre mRNA and 300 µg of recombination plasmid. 19% of the cells from pool no 5 contain the exchange vector in 2 integration sites, one of which is targeted and another in the random site of the genome. In 39% of the cells, the targeted integration has not occurred, and the recombination plasmid has integrated to the random site of the genome. The frequency of random integration is high (~60% or more) in cell pools no. 1-3 (transfected with 1 µg of Cre mRNA) and no. 4 (transfected with 3 µg of Cre mRNA and 100 ng exchange vector). Compared to cell pool no. 5, pool no. 6 (3 µg of Cre mRNA and 1000 ng exchange vector) has slightly higher frequency (45%) for random integration and lower (31%) for targeted integration with one integration site. Therefore, the pool no. 5 will be sub-cloned by limiting dilution.

Similar experiment was also performed with Flp recombinase and the exchange vectors containing incompatible recombination target sequences of this enzyme, namely FRT1 and FRT6 sites. It has been shown by several authors that RMCE using FRT sites is efficient and precise and could be used for development of cell lines encoding for protein of interest (Kim and Lee, 2008; Zhang et al., 2015). However, in our system, the frequency of site-specific integration using the Lox2272 and LoxP sites is higher compared to the use of FRT1 and FRT6 sites. In our system, Cre recombinase and exchange plasmids containing its incompatible recombination target sites Lox2272 and LoxP are preferred according to the results of this investigation.

Transfection with 3 µg Cre mRNA and 300 µg recombination plasmid yielded the cell pool with highest frequency of RMCE and lowest frequency of random integration and thus, these conditions will be used for following cell line developments with the #504 C6 parental cell line.

Example 8

Generation of a Cell Line Expressing Recombinant Protein

For generation of clonal cell line expressing human transferrin, the cell pool that had the highest frequency of targeted integration was sub-cloned by limiting dilution. After 3-4 weeks, screening of the loss of 4F3 scFv was performed in 96-well format to select cells with targeted integration of the exchange vector and to eliminate clones with random integration of the cassette. The cell lines without 4F3 scFv were expanded to 24-well and to 6-well and normalized to similar density. hTF expression was analyzed using the commercial ELISA kit (Abcam, Cat. No. ab187391) according to manufacturer's recommendation. Cell lines #24, #57, #64, #82, #85, #89 and #107, expressing hTF at highest level, were transferred to 125 ml shaker flasks, cultivated to desired cell density for research cell bank generation. After that, the productivities of cell lines were tested in small-scale fed-batch culture, similarly to 4F3 production described in example 2, except Feed B (not the mixture of Feed A and B) was added every 2 days. Production supernatants were analyzed by SDS-Page followed by Coomassie blue staining (FIG. 10A) and the amount of hTF in the media/productivities of hTF cell lines were quantified with hTF ELISA kit (FIG. 10B).

The Coomassie blue staining of hTF production supernatants (FIG. 10A) demonstrate the proteins are intact and the migration properties of the produced protein are as expected (~75 kDa). The presence of other cellular proteins in the production media is minimal. According to the SDS-Page analysis, clone #82 produces hTF protein at highest level, followed by a control #40-35 from another development. hTF quantification by Elisa (FIG. 10B) confirm that clone #82 with productivity of 369 mg/l is the best cell line, followed by clone #107 and control #40-35 both producing human transferrin with productivity of ~300 mg/l. Thus, the use of RMCE using the #504 C6 parental cell line permits to develop protein of interest cell lines with good productivity.

Example 9

Protein of Interest Cell Lines Developed from #504 C6 Parental Cell Line by RMCE Express BPV1 E2 Protein The parental cell line #504 C6 is BPV1 E2 positive, meaning that it expresses E2 protein at detectable level. Although, BPV1 E2 expression cassette is integrated to the #504 C6 landing pad cell line, it is unknown whether E2 protein is also expressed in protein of interest cell lines that have undergone RMCE, antibiotic selection and the long cultivation time from single cell to RCB. Western blot analysis was performed to test the BPV1 E2 protein expression in hTF cell lines. For this, cells in fed-batch production were counted, lysed and the lysate of ~50 000 cells was analyzed. The immunoblot in FIG. 11 show that BPV1 E2 protein expression is stable as the protein is detectable in all hTF cell lines.

Thus, BPV1 E2 protein expression is stable in protein of interest producing cell lines generated from #504 C6. It is possible, that the transactivation properties of E2 that lead to upregulation of gene expression from promoters close to E2BSs could also occur in stable cell lines generated by RMCE.

REFERENCES

Bebbington, C. R., Renner, G., Thomson, S., King, D., Abrams, D., and Yarranton, G. T. (1992). High-level expression of a recombinant antibody from myeloma cells using a glutamine synthetase gene as an amplifiable selectable marker. Biotechnol. Nat. Publ. Co. 10, 169-175.

Frye, C., Deshpande, R., Estes, S., Francissen, K., Joly, J., Lubiniecki, A., Munro, T., Russell, R., Wang, T., and Anderson, K. (2016). Industry view on the relative importance of "clonality" of biopharmaceutical-producing cell lines. Biol. J. Int. Assoc. Biol. Stand. 44, 117-122.

Inniss, M. C., Bandara, K., Jusiak, B., Lu, T. K., Weiss, R., Wroblewska, L., and Zhang, L. (2017). A novel Bxb1 integrase RMCE system for high fidelity site-specific integration of mAb expression cassette in CHO Cells. Biotechnol. Bioeng. 114, 1837-1846.

Kaufman, R. J., and Sharp, P. A. (1982). Amplification and expression of sequences cotransfected with a modular dihydrofolate reductase complementary dna gene. J. Mol. Biol. 159, 601-621.

Kim, M. S., and Lee, G. M. (2008). Use of Flp-mediated cassette exchange in the development of a CHO cell line stably producing erythropoietin. J. Microbiol. Biotechnol. 18, 1342-1351.

Liu, P.-Q., Chan, E. M., Cost, G. J., Zhang, L., Wang, J., Miller, J. C., Guschin, D. Y., Reik, A., Holmes, M. C., Mott, J. E., et al. (2010). Generation of a triple-gene knockout mammalian cell line using engineered zinc-finger nucleases. Biotechnol. Bioeng. 106, 97-105.

Urlaub, G., and Chasin, L. A. (1980). Isolation of Chinese hamster cell mutants deficient in dihydrofolate reductase activity. Proc. Natl. Acad. Sci. U.S.A. 77, 4216-4220.

Wigler, M., Perucho, M., Kurtz, D., Dana, S., Pellicer, A., Axel, R., and Silverstein, S. (1980). Transformation of mammalian cells with an amplifiable dominant-acting gene. Proc. Natl. Acad. Sci. U.S.A. 77, 3567-3570.

Zhang, L., Inniss, M. C., Han, S., Moffat, M., Jones, H., Zhang, B., Cox, W. L., Rance, J. R, and Young, R. J. (2015). Recombinase-mediated cassette exchange (RMCE) for monoclonal antibody expression in the commercially relevant CHOK1SV cell line. Biotechnol. Prog. 31, 1645-1656.

Zhu, J. (2012). Mammalian cell protein expression for biopharmaceutical production. Biotechnol. Adv. 30, 1158-1170.

What is claimed is:

1. A landing pad construct comprising recognition sites of site-specific recombinases, wherein the recognition sites are at the 5' and 3' ends of the landing pad construct, and between the recognition sites the landing pad construct further comprises a reporter gene comprising the nucleotide sequence of SEQ ID NO: 11 encoding a detectable reporter protein 4F3 scFV, a nucleotide sequence encoding a selection marker, and binding sites of a bovine papillomavirus (BPV1) E2 protein.

2. The landing pad construct of claim 1, wherein the recognition sites of site-specific recombinases are wild-type recombination sites of Cre recombinase wherein the wild-type recombination sites of the Cre recombinase comprise the nucleotide sequence of SEQ ID NO: 5.

3. The landing pad construct of claim 1, wherein the recognition sites of site-specific recombinases are incompatible Cre recombinase sites.

4. The landing pad construct of claim 1, wherein at least one nucleotide sequence encoding a selection marker and at least one reporter gene are linked with a nucleotide sequence encoding a Foot and Mouth Disease Virus (FMDV) 2A peptide.

5. The landing pad construct of claim 1, wherein the landing pad construct comprises the nucleotide sequence of SEQ ID NO: 2.

6. An isolated cell line comprising the landing pad construct of claim 1.

7. An isolated cell line comprising the landing pad construct of claim 1, and an expression plasmid comprising a nucleotide sequence encoding a BPV1 E2 protein.

8. The cell line of claim 6, wherein the cell line is a mammalian cell line.

9. The cell line of claim 8, wherein the cell line is a Chinese Hamster Ovary (CHO) cell line.

10. A method to develop parental cell lines, said method comprising the steps of:
a) providing the landing pad construct of claim 1;
b) providing an expression plasmid comprising a nucleotide sequence encoding a BPV1 E2 protein;
c) co-transfecting a cell with the landing pad construct and the expression plasmid;
d) allowing expression from the landing pad construct and the expression plasmid; and
e) selecting parental cell lines that express the reporter gene.

11. A method for expression of a gene of interest, said method comprising the steps of:
a) developing a parental cell line according to the method of claim 10;
b) providing a gene of interest construct comprising the same recognition sites of site-specific recombinases as the landing pad construct;
c) replacing the landing pad construct with the gene of interest construct by co-transfecting the parental cell line with the gene of interest construct and an expression construct or mRNA for site-specific recombinases recognized by the recognition site; and
d) cultivating the cell line in an environment suitable for expression of the gene of interest.

12. The method of claim 10, wherein the cell line is a mammalian cell line.

13. The method of claim 12, wherein the cell line is a CHO cell line.

14. A kit for developing cell lines for production of at least one protein of interest, the kit comprising:
the landing pad construct of claim 1;
an expression plasmid comprising a nucleotide sequence encoding a BPV1 E2 protein;
a gene of interest construct comprising coding sequences for the at least one protein of interest and the same recognition sites of site-specific recombinases as the landing pad construct; and
a suitable cell line for co-transfection.

15. The landing pad construct of claim 3, wherein the incompatible Cre recombinase sites are a LoxP site and a Lox2272 site, having the nucleotide sequences of SEQ ID NO: 5 and SEQ ID NO: 6, respectively.

* * * * *